US00RE42704E

(19) United States
(12) Reissued Patent
Prunkard et al.

(10) Patent Number: US RE42,704 E
(45) Date of Reissued Patent: Sep. 13, 2011

(54) PRODUCTION OF FIBRINOGEN IN TRANSGENIC ANIMALS

(75) Inventors: Donna E. Prunkard, Seattle, WA (US); Donald C. Foster, Lake Forest Park, WA (US)

(73) Assignee: Pharming Intellectual Property B.V., Al Leiden (NL)

(21) Appl. No.: 09/232,488

(22) Filed: Jan. 15, 1999

Related U.S. Patent Documents

Reissue of:
(64) Patent No.: 5,639,940
Issued: Jun. 17, 1997
Appl. No.: 08/206,176
Filed: Mar. 3, 1994

(51) Int. Cl.
*C12P 21/00* (2006.01)
*A01K 67/00* (2006.01)
*C12N 15/00* (2006.01)

(52) U.S. Cl. ..... 800/7; 800/14; 800/15; 800/16; 800/17; 800/18; 800/25; 435/320.1

(58) Field of Classification Search ..... 800/7, 14–18, 800/25; 435/320.1
See application file for complete search history.

(56) References Cited

U.S. PATENT DOCUMENTS

| | | | |
|---|---|---|---|
| 4,873,316 | A | 10/1989 | Meade et al. |
| 5,304,489 | A | 4/1994 | Rosen |
| 5,366,894 | A | 11/1994 | Clark et al. |

FOREIGN PATENT DOCUMENTS

| | | |
|---|---|---|
| WO | WO88/00239 | 1/1988 |
| WO | WO 90/05188 | 5/1990 |
| WO | WO91/03216 | 6/1991 |
| WO | WO91/08216 | 6/1991 |
| WO | WO92/11358 | 7/1992 |
| WO | WO92/11757 | 7/1992 |

OTHER PUBLICATIONS

Garner's Preliminary Motion No. 1, Aug. 16, 2001.
Declaration of Alan Colman, Aug. 16, 2001.
Declaration of David Toman, Aug. 16, 2001.
Declaration of Lothar Hennighausen, Aug. 16, 2001.
Declaration of Jeffrey Rosen, Aug. 16, 2001.
Yarus et al, *Genetic Engineering,* 18: 57-81 (1996).
Reddy et al., *Animal Biotechnology* 2: 15-29 (1991).
Tojo et al., *J. Reprod. Develop.* 39: 145-155 (1993).
Farrell et al., *Biochemistry,* 30: 9414-9420 (1991).
Velander's Preliminary Motion No. 1, Aug. 16, 2001.
Garner's Opposition to Velander's Preliminary Motion No. 1, Aug. 16, 2001.
Prunkard et al., *Nature Biotechnology,* 14:867-871, 870 (1996).
Hurtley et al., *Annu. Rev. Cell Biol.* 5: 277-307 (1989).
Prunkard et al., (Abstract) *J. Cell Biochem., Suppl. 17C* (1993).
Drohan et al., *Transgenic Research,* 3: 355-364 (1994).
Velander et al., *PNAS* (*USA*), 89: 12003-12007 (1992).
Pittius et al., *PNAS USA,* 85: 5874 (1988).
Simons et al., *Biotechnology,* 6:179 (1988).
Clark et al., *Biotechnology,* 7:487 (1989).
Garner's Motion to Correct Inventorship, Aug. 16, 2001.
Garner's Preliminary Motion No. 2, Aug. 16, 2001.
Hennighausen, *Protein Expression and Publication* 1: 3-8 (1990).
Garner Exhibit No. 28—Typed Notes, Aug. 16, 2001.
Masoud et al., *Ann. Zootech.* 45: -9 (1996).
Garner's Reply in Support of Garner's Preliminary Motion 1, Aug. 16, 2001.
Second Declaration of Alan Colman, Aug. 16, 2001.
Declaration of Richard F. Lathe, Aug. 16, 2001.
Behringer et al., "Synthesis Of Functional Human Hemoglobin In Transgenic Mice," *Science*, 245:971-973 (1989).
Binnie et al, "Characterization Of Purified Recombinant Fibrinogen: Partial Phosphorylation Of Fibrinopeptide A," *Biochemistry*, 32:107-113 (1993).
Bolyard, M.G., et al., "Expression In *Escherichia Coli* Of The Human Fibrinogen Bβ Chains And Its Cleavage By Thrombin," *Blood*, 73:1202-1206, 1989.
Burdon et al., "Expression Of A Whey Acidic Protein Transgene During Mammary Development," *The Journal of Biological Chemistry*, 266(11):6909-6914 (1991).
Chung, Dominic W., et al., "Characterization Of A Complementary Deoxyribonucleic Acid and Genomic Deoxyribonucleic Acid For The β Chain Of Human Fibrinogen," *Biochemistry*, 22:3244-3250.
Chung et al., "Characterization Of A Complementary Deoxyribonucleic Acid Coding For The γ Chain Of Human Fibrinogen," *Biochemistry*, 22(13):3250-3256 (1983).
Chung et al., "Nucleotide Sequences Of The Three Genes Coding For Human Fibrinogen," *Adv. Exp. Med.*, 201:39-48 (1990).
Clark et al., "Pharmaceuticals From Transgenic Livestock," *Tibtech*, 5:20-24 (1987).
Clark et al., "Expression of human anti-hemophilic factor IX in the milk of transgenic sheep," *Bio/Technology*, 7:487-492 (1989).
Clark et al., "Rescuing Transgene Expression By Co-Integration," *Bio/Technology*, 10:1450-1454.
Danishefsky, K., et al., "Intracellular Fate Of Fibrinogen Bβ Chain Expressed in COS Cells," *Biochem, Biophys. Acta*, 1048:202-208 (1990).
James Darnell, *Molecular Cell Biology* abstract "The Organization Of DNA Differs Greatly In Prokaryotic and Eukaryotic Cells," p. 137 (Scientific American Books, 1986).
DiTullio et al., "Production Of Cystic Fibrosis Transmembrane Conductance Regulator In The Milk of Transgenic Mice," *Bio/Technology*, 10:74-77 (1992).
Dobrovolsky et al, "Human γ-Interferon Expression In The Mammary Gland Of Transgenic Mice," *FEBS Letters*, 319:181-184 (1993).

(Continued)

*Primary Examiner* — Deborah Crouch
(74) *Attorney, Agent, or Firm* — Alston and Bird LLP

(57) ABSTRACT

Materials and methods for producing fibrinogen in transgenic non-human mammals are disclosed. DNA segments encoding Aα, Bβ and γ chains of fibrinogen are introduced into the germ line of a non-human mammal, and the mammal or its female progeny produces milk containing fibrinogen expressed from the introduced DNA segments. Non-human mammalian embryos and transgenic non-human mammals carrying DNA segments encoding heterologous fibrinogen polypeptide chains are also disclosed.

17 Claims, 5 Drawing Sheets

OTHER PUBLICATIONS

Drohan et al., "Inefficient Processing Of Human Protein C In The Mouse Mammary Gland," *Transgenic Research*, 3:355-364 (1994).
Farrell, D.H. et al., "Binding Of Recombinant Fibrinogen Mutants To Platelets," *J. Biol. Chem.*, 269:226-231 (1994).
Farrell et al., "Recombinant Human Fibrinogen And Sulfation Of The 65 ' Chain," *Biochemistry*, 30(39):9414-9420 (1991).
Greenberg et al., "Expression Of Biologically Active Heterodimeric Bovine Follicle-Stimulating Hormone In Milk Of Transgenic Mice," *Biochemistry*, 88:8327-8331 (1991).
Grosschedl, R., et al., "Introduction Of A μ Immunoglobulin Gene Into The Mouse Germ Line; Specific Expression In Lymphoid Cells And Synthesis Of Functional Antibody," *Cell*, 38:647-658 (1984).
Hartwig, R. et al., "Studies On The Assembly And Secretion Of Fibrinogen," *J. Biol. Chem.*, 266:6578-6585 (1991).
Hennighausen, Lothar, "The Mammary Gland As A Bioreactor: Production Of Foreign Proteins In Milk," *Protein Expression And Purification*, 1:3-8 (1990).
Hurtley et al., "Protein Obligomerization In The Endoplasmic Reticulum," *Annu. Rev. Cell Biol*, 5: 277-307 (1989).
Lee, S.H., et al., "Production Of Biomedical Proteins In The Milk Of Transgenic Dairy Cows; The State Of The Art," *J. Controlled Release*, 29:213-221 (1994).
Lord, Susan T., "Expression Of A Cloned Human Fibrinogen cDNA In *Escherichia Coli*: Synthesis Of An A Alpha Polypeptide," *DNA*, 4:33-38 (1980).
Lord, Susan T., et al., "Expression Of A Fibrinogen Fusion Peptide In *Escherichia Coli*: A Model Thrombin Substrate For Structure/Function Analysis," *Blood*, 73:166-171 (1989).
Massoud et al., "The Deleterious Effects Of Human Erythropoietin Gene Driven By The Rabbit Whey Acidic Protein Gene Promoter In Transgenic Rabbits," *Ann Zootech*, 45:1-9 (1996).
McClenaghan et al., "Secretory Proteins Compete For Production In The Mammary Gland Of Transgenic Mice," *Biochemical Journal*, 310:637-641 (1995).
Mishina et al., "Molecular Distinction Between Fetal And Adult Forms Of Muscle Acetylcholine Receptor," *Nature*, 321:406-411 (1986).
Morocöl et al., "The Porcine Mammary Gland As A Bioreactor For Complex Proteins," *Recombinant DNA Technology II*, 721:21-233 (1994).
Nicoll et al., "Estimates Of Parenchymal, Stromal, And Lymph Node Deoxyribonucleic Acid In Mammary Glands Of C311/Crgl/2 MICE," *Life Sciences*, 4(9):993-1001 (1965).
Palmiter, Richard D., et al., "Transgenic Mice," *Cell*, 41:343-345 (1985).
Pittius et al., "A Milk Protein Gene Promoter Directs The Expression Of Human Tissue Plasminogen Activator cDNA To The Mammary Gland In Transgenic Mice," *Biochemistry*, 85:5874-5878 (1988).
Prunkard et al. UCLA Symposia On Molecular And Cellular Biology (Feb. 8-14, 1993, Taos, New Mexico), "High Level Secretion Of Recombinant Human Fibrinogen In BHK Cells Is Limited By A Post-Transcriptional Process," *Journal of Ceilular Biochemistry*, vol. 17C, Abstract H123 (1993).
Prunkard et al., "High-Level Expression Of Recombinant Human Fibrinogen In The Milk Of Transgenic Mice," *Nature Biotechnology*, 14:867-871 (1996).
Reddy et al., "Expression Of Human Growth Hormone In The Milk Of Transgenic Mice," *Animal Biotechnology*, 2(1):15-29. (1991).
Redman, C., et al., "Recombinant Production, Secretion, And Clotting Behavior Of Fibrinogen And Cell Line Used Therein," *Chemical Abstracts*, 115: 526 (1991).
Rixon, M.W., et al., "Nucleotide Sequence Of The Gene For The γ Chain Of Human Fibrinogen," *Biochemistry*, 24:2077-2086 (1985).
Rixon et al., "Characterization Of A Complementary Deoxyribonucleic Acid Coding For The α Chain Of Human Fibrinogen," *Biochemistry*, 22(13):3237-3244 (1983).
Roy et al., "Assembly And Secretion Of Recombinant Human Fibrinogen," *The Journal of Biological Chemistry*, 266(8):4758-4763 (1991).
Shani et al., "Expression Of Human Serum Albumin In The Milk Of Transgenic Mice," *Transgenic Research*, 1(5):195-208 (1992).
Simons et al., "Gene Transfer Into Sheep," *Bio/Technology*, 6:179-183 (1988).
Sinai Yarus et al., "Engineering Transgenes For Use In The Mammary Gland," *Genetic Engineering*, 18:57-81 (1996).
Storb et ai., "Transgenic Mice With μ And ∢ Genes Encoding Antiphosphorylcholine Antibodies," *The Journal of Experimental Medicine*, 164:627-641 (1986).
Tojo et al., "Production And Characterization Of Transgenic Mice Expressing A hGH Fusion Gene Driven By The Promoter Of Mouse Whey Acidic Protein (mWAP) Putatively Specific To Mammary Gland," *Journal of Reproduction and Development*, 39(2):145-155 (1993).
Turner et ai., "Proteins Are Secreted By Both Constitutive And Regulated Secretory Pathways In Lactating Mouse Mammary Epithelial Cells," *The Journal of Cell Biology*, 117:269-278 (1992).
Velander et al., "High-Level Expression Of A Heterologous Protein In The Milk Of Transgenic Swine USing The cDNA Encoding Human Protein C," *Applied Biological Sciences*, 89:12003-12007 (1992).
Whitelaw et al., "Position-Independent Expression Of The Ovine β-Lactoglobulin Gene In Transgenic Mice," *Biochemical Journal*, 286:31-39 (1992).
Wilkins et al., "Isolation Of Recombinant Proteins From Milk," *Journal of Cellular Biochemistry*, 49:333-338 (1992).
Yu et al., "Fibrinogen Precursors," *The Journal of Biological Chemistry*, 259(16)10574-10581 (1984).
Yu et al., "Functional Human CD4 Protein Produced In Milk Of Transgenic Mice," *Mol. Biol. Med.*, 6:255-261 (1989).
Bolyard et al., *Gene* 66: 183-192, 1988.
Wall, 1996, Themogeneology 45:57-68.
Houdebine, 1994, Journal of Biotechnology 34:269-287.
*Genes,* Lewin, ed., John Wiley and Sons, N.Y. pp. 87-96.
D.F. Hosher, "Disorders of Blood Coagulation" in *Cecil Textbook of Medicine,* 18$^{th}$ Ed., Wyngaarden et al., eds., W.B. Saunders Co., Philadelphia, 1988. pp. 1060-1065.

PRODUCTION OF FIBRINOGEN IN TRANSGENIC ANIMALS

Matter enclosed in heavy brackets [ ] appears in the original patent but forms no part of this reissue specification; matter printed in italics indicates the additions made by reissue.

BACKGROUND OF THE INVENTION

The final step in the blood coagulation cascade is the thrombin-catalyzed conversion of the soluble plasma protein fibrinogen to insoluble fibrin. Thrombin cleaves a small peptide (fibrinopeptide A) from one of the three component chains (the Aα-chain) of fibrinogen. Fibrin monomers subsequently polymerize and are cross-linked by activated factor XIII to form a stable clot.

Fibrinogen is a key component of biological tissue glues (see, e.g., U.S. Pat. Nos. 4,377,572 and 4,442,655), which mimic the formation of natural blood clots to promote hemostasis and repair damaged tissue. Tissue glues provide an adjunct or alternative to sutures, staples and other mechanical means for wound closure. However, the principal ingredients of these products (fibrinogen, factor XIII and thrombin) are prepared from pooled human plasma by cryoprecipitation (e.g. U.S. Pat. Nos. 4,377,572; 4,362,567; 4,909,251) or ethanol precipitation (e.g. U.S. Pat. No. 4,442,655) or from single donor plasma (e.g. U.S. Pat. No. 4,627,879; Spotnitz et al., Am. Surg. 55: 166-168, 1989). The resultant fibrinogen/factor XIII preparation is mixed with bovine thrombin immediately before use to convert the fibrinogen to fibrin and activate the factor XIII, thus initiating coagulation of the adhesive.

Commercially available adhesives are of pooled plasma origin. Because blood-derived products have been associated with the transmission of human immunodeficiency virus (HIV), hepatitis virus and other etiologic agents, the acceptance and availability of such adhesives is limited. At present they are not approved for use in the United States.

While the use of autologous plasma reduces the risk of disease transmission, autologous adhesives can only be used in elective surgery when the patient is able to donate the necessary blood in advance.

As noted above, fibrinogen consists of three polypeptide chains, each of which is present in two copies in the assembled molecule. These chains, designated the Aα, Bβ and γ-chains, are coordinately expressed, assembled and secreted by the liver. While it might be expected that recombinant DNA technology could provide an alternative to the isolation of fibrinogen from plasma, this goal has proven to be elusive. The three fibrinogen chains have been individually expressed in E. coli (Lord, DNA 4: 33-38, 1985; Bolyard and Lord, Gene 66: 183-192, 1988; Bolyard and Lord, Blood 73: 1202-1206), but functional fibrinogen has not been produced in a prokaryotic system. Expression of biologically competent fibrinogen in yeast has not been reported. Cultured transfected mammalian cells have been used to express biologically active fibrinogen (Farrell et al., Blood 74: 55a, 1989; Hartwig and Danishefsky, J. Biol. Chem. 266: 6578-6585, 1991; Farrell et al., Biochemistry 30: 9414-9420, 1991), but expression levels have been so low that production of recombinant fibrinogen in commercial quantities is not feasible. Experimental evidence suggests that lower transcription rates in cultured cells as compared to liver may be a factor in the low expression rates achieved to date, but increasing the amount of fibrinogen chain mRNA in transfected BHK cells did not produce corresponding increases in fibrinogen protein secretion (Prunkard and Foster, XIV Congress of the International Society on Thrombosis and Haemostasis, 1993). These latter results suggest that proper assembly and processing of fibrinogen involves tissue-specific mechanisms not present in common laboratory cell lines.

There remains a need in the art for methods of producing large quantities of high quality fibrinogen for use in tissue adhesives and other applications. There is a further need for fibrinogen that is free of blood-borne pathogens. The present invention fulfills these needs and provides other, related advantages.

SUMMARY OF THE INVENTION

It is an object of the present invention to provide commercially useful quantities of recombinant fibrinogen, particularly recombinant human fibrinogen. It is a further object of the invention to provide materials and methods for expressing fibrinogen in the mammary tissue of transgenic animals, particularly livestock animals such as cattle, sheep, pigs and goats.

Within one aspect, the present invention provides a method for producing fibrinogen comprising (a) providing a first DNA segment encoding a secretion signal operably linked to a fibrinogen Aα chain, a second DNA segment encoding a secretion signal operably linked to a fibrinogen Bβ chain, and a third DNA segment encoding a secretion signal operably linked to a fibrinogen γ chain, wherein each of the first, second and third segments is operably linked to additional DNA segments required for its expression in the mammary gland of a host female mammal; (b) introducing the DNA segments into a fertilized egg of a non-human mammalian species; (c) inserting the egg into an oviduct or uterus of a female of the species to obtain offspring carrying the DNA constructs; (d) breeding the offspring to produce female progeny that express the first, second and third DNA segments and produce milk containing biocompetent fibrinogen encoded by the segments; (e) collecting milk from the female progeny; and (f) recovering the fibrinogen from the milk. Within one embodiment, the egg containing the introduced segments is cultured for a period of time prior to insertion.

Within another aspect, the invention provides a method of producing fibrinogen comprising the steps of (a) incorporating a first DNA segment encoding a secretion signal operably linked to an Aα chain of fibrinogen into a β-lactoglobulin gene to produce a first gene fusion; (b) incorporating a second DNA segment encoding a secretion signal operably linked to a Bβ chain of fibrinogen into a β-lactoglobulin gene to produce a second gene fusion; (c) incorporating a third DNA segment encoding a secretion signal operably linked to a γ chain of fibrinogen into a β-lactoglobulin gene to produce a third gene fusion; (d) introducing the first, second and third gene fusions into the germ line of a non-human mammal so that the DNA segments are expressed in a mammary gland of the mammal or its female progeny and biocompetent fibrinogen is secreted into milk of the mammal or its female progeny; (e) obtaining milk from the mammal or its female progeny; and (f) recovering the fibrinogen from the milk. Within preferred embodiments, the mammal is a sheep, pig, goat or bovine.

Within another aspect, the invention provides a method for producing fibrinogen comprising the steps of (a) providing a transgenic female non-human mammal carrying in its germline heterologous DNA segments encoding Aα, Bβ and γ chains of fibrinogen, wherein the DNA segments are expressed in a mammary gland of the mammal and fibrinogen encoded by the DNA segments is secreted into milk of the mammal; (b) collecting milk from the mammal; and (c) recovering the fibrinogen from the milk.

Within another aspect, the invention provides a non-human mammalian embryo containing in its nucleus heterologous DNA segments encoding Aα, Bβ and γ chains of fibrinogen. Within a related aspect, the invention provides a transgenic non-human female mammal that produces recoverable amounts of human fibrinogen in its milk.

Within another aspect, the invention provides a method for producing a transgenic offspring of a mammal comprising the steps of (a) providing a first DNA segment encoding a fibrinogen Aα chain, a second DNA segment encoding a fibrinogen Bβ chain, and a third DNA segment encoding a fibrinogen γ chain, wherein each of said first, second and third segments is operably linked to additional DNA segments required for its expression in a mammary gland of a host female mammal and secretion into milk of the host female mammal; (b) introducing the DNA segments into a fertilized egg of a mammal of a non-human species; (c) inserting the egg into an oviduct or uterus of a female of the non-human species to obtain an offspring carrying the first, second and third DNA segments. In a related aspect, the invention provides non-human mammals produced according to this process.

Within an additional aspect, the invention provides a non-human mammal carrying its germline DNA segments encoding heterologous Aα, Bβ and γ chains of fibrinogen, wherein female progeny of the mammal express the DNA segments in a mammary gland to produce biocompetent fibrinogen.

These and other aspects of the invention will become evident to the skilled practitioner upon reference to the following detailed description and the attached drawings.

DETAILED DESCRIPTION OF THE INVENTION

Figure 1:
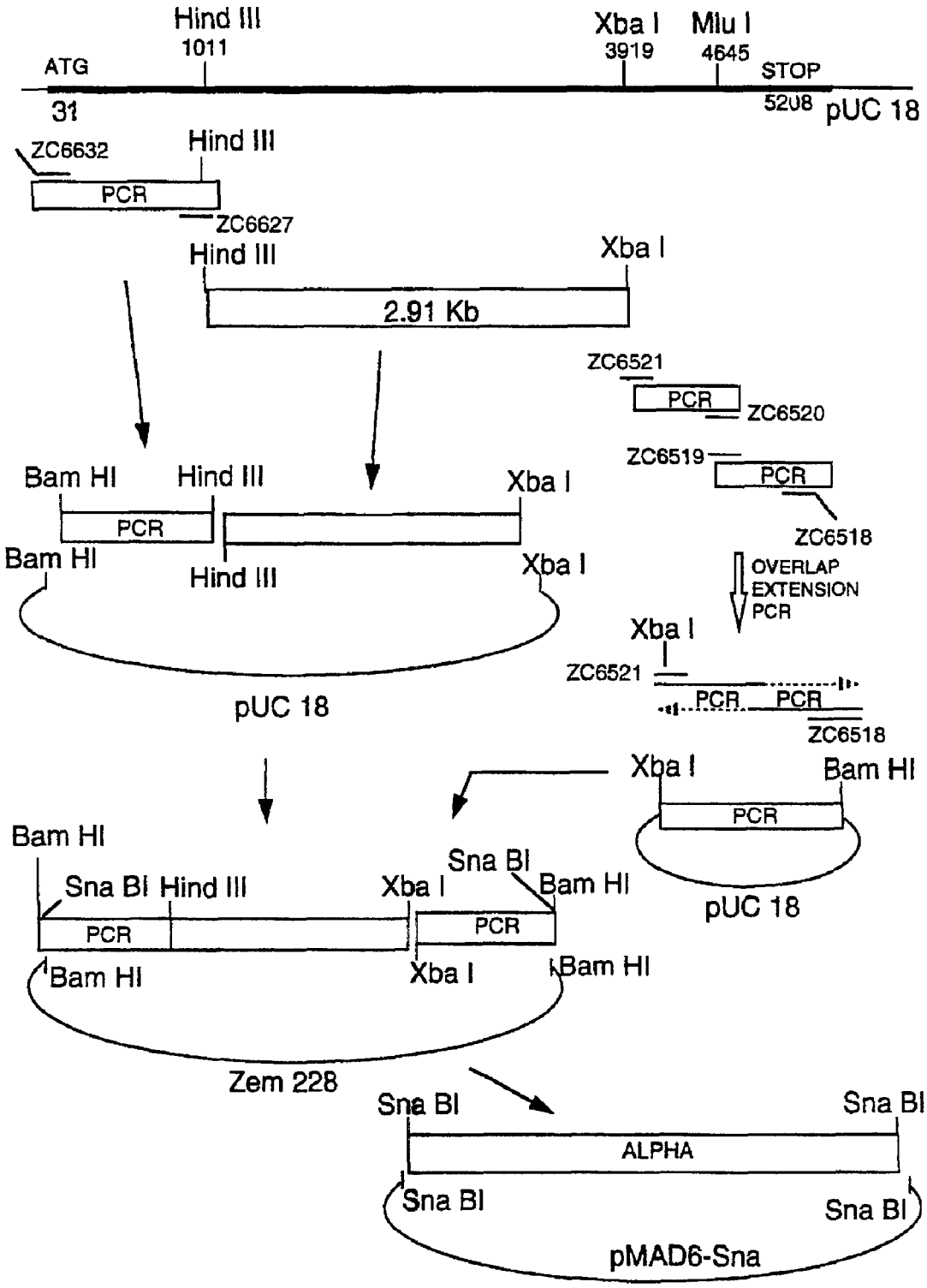
FIG. 1 illustrates the subcloning of a human fibrinogen Aα chain DNA sequence.

Prior to setting forth the invention in detail, it will be helpful to define certain terms used herein:

As used herein, the term "biocompetent fibrinogen" is used to denote fibrinogen that polymerizes when treated with thrombin to form insoluble fibrin.

The term "egg" is used to denote an unfertilized ovum, a fertilized ovum prior to fusion of the pronuclei or an early stage embryo (fertilized ovum with fused pronuclei).

A "female mammal that produces milk containing biocompetent fibrinogen" is one that, following pregnancy and delivery, produces, during the lactation period, milk containing recoverable amounts of biocompetent fibrinogen. Those skilled in the art will recognized that such animals will produce milk and therefore the fibrinogen, discontinuously.

The term "progeny" is used in its usual sense to include children and descendants.

The term "heterologous" is used to denote genetic material originating from a different species than that into which it has been introduced, or a protein produced from such genetic material.

Within the present invention, transgenic animal technology is employed to produce fibrinogen within the mammary glands of a host female mammal. Expression in the mammary gland and subsequent secretion of the protein of interest into the milk overcomes many difficulties encountered in isolating proteins from other sources. Milk is readily collected, available in large quantities, and well characterized biochemically. Furthermore, the major milk proteins are present in milk at high concentrations (from about 1 to 15 g/l).

From a commercial point of view, it is clearly preferable to use as the host a species that has a large milk yield. While smaller animals such as mice and rats can be used (and are preferred at the proof-of-concept stage), within the present invention it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk. See WO 88/00239 for a comparison of factors influencing the choice of host species. It is generally desirable to select a breed of host animal that has been bred for dairy use, such as East Friesland sheep, or to introduce dairy stock by breeding of the transgenic line at a later date. In any event, animals of known, good health status should be used.

Fibrinogen produced according to the present invention may be human fibrinogen or fibrinogen of a non-human animal. For medical uses, it is preferred to employ proteins native to the patient. The present invention thus provides fibrinogen for use in both human and veterinary medicine. Cloned DNA molecules encoding the component chains of human fibrinogen are disclosed by Rixon et al. (Biochem. 22: 3237, 1983), Chung et al. (Biochem. 22: 3244, 1983), Chung et al. (Biochem. 22: 3250, 1983), Chung et al. (Adv. Exp. Med. Biol. 281: 39-48, 1990) and Chung et al. (Ann. NY Acad. Sci. 408: 449-456, 1983). Bovine fibrinogen clones are disclosed by Brown et al. (Nuc. Acids Res. 17: 6397, 1989) and Chung et al. (Proc. Natl. Acad. Sci. USA 78: 1466-1470, 1981). Other mammalian fibrinogen clones are disclosed by Murakawa et al. (Thromb. Haemost. 69: 351-360, 1993). Representative sequences of human Aα, Bβ and γ chain genes are shown in SEQ ID NOS: 1, 3 and 5, respectively. Those skilled in the art will recognize that allelic variants of these sequences will exist; that additional variants can be generated by amino acid substitution, deletion, or insertion; and that such variants are useful within the present invention. In general, it is preferred that any engineered variants comprise only a limited number of amino acid substitutions, deletions, or insertions, and that any substitutions are conservative. Thus, it is preferred to produce fibrinogen chain polypeptides that are at least 90%, preferably at least 95, and more preferably 99% or more identical in sequence to the corresponding native chains. The term "γ chain" is meant to include the alternatively spliced γ' chain of fibrinogen (Chung et al., Biochem. 23: 4232-4236, 1984). A human γ' chain amino acid sequence is shown in SEQ ID NO: 6. The shorter γ chain is produced by alternative splicing at nucleotides 9511 and 10054 of SEQ ID NO: 5, resulting in translation terminating after nucleotide 10065 of SEQ ID NO: 5.

To obtain expression in the mammary gland, a transcription promoter from a milk protein gene is used. Milk protein genes include those genes encoding caseins, beta-lactoglobulin (BLG), α-lactalbumin, and whey acidic protein. The beta-lactoglobulin promoter is preferred. In the case of the ovine beta-lactoglobulin gene, a region of at least the proximal 406 bp of 5' flanking sequence of the ovine BLG gene (contained within nucleotides 3844 to 4257 of SEQ ID NO:7) will generally be used. Larger portions at the 5' flanking sequence, up to about 5 kbp, are preferred. A larger DNA segment encompassing the 5' flanking promoter region and the legion encoding the 5' non-coding portion of the beta-lactoglobulin gene (contained within nucleotides 1 to 4257 of SEQ ID NO:7) is particularly preferred. See Whitelaw et al., Biochem J. 28: 31-39, 1992. Similar fragments of promoter DNA from other species are also suitable.

Other regions of the beta-lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., Proc. Natl. Acad. Sci. USA 85: 836-840, 1988; Palmiter et al., Proc. Natl. Acad. Sci. USA 88: 478-482, 1991; Whitelaw et al., Transgenic Res. 1: 3-13, 1991; WO 89/01343; WO 91/02318). In this regard, it is generally preferred, where possible, to use genomic sequences containing all or some of the native introns of a gene encoding the protein or polypeptide of interest. Within certain embodiments of the invention, the further inclusion of at least some introns from the beta-lactoglobulin gene is preferred. One such region is a DNA segment which provides for intron splicing and RNA polyadenylatiom from the 3' non-coding region of the ovine beta-lactoglobulin gene. When substituted for the natural 3' non-coding sequences of a gene, this ovine beta-lactoglobulin segment can both enhance and stabilize expression levels of the protein or polypeptide of interest. Within other embodiments, the region surrounding the initiation ATG of one or more of the fibrinogen sequences is replaced with corresponding sequences from a milk specific protein gene. Such replacement provides a putative tissue-specific initiation environment to enhance expression. It is convenient to replace the entire fibrinogen chain pre-pro and 5' non-coding sequences with those of, for example, the BLG gene, although smaller regions may be replaced.

For expression of fibrinogen, DNA segments encoding each of the three component polypeptide chains of fibrinogen are operably linked to additional DNA segments required for their expression to produce expression units. Such additional segments include the above-mentioned milk protein gene promoter, as well as sequences which provide for termination of transcription and polyadenylation of mRNA. The expression units will further include a DNA segment encoding a secretion signal operably linked to the segment encoding the fibrinogen polypeptide chain. The secretion signal may be a native fibrinogen secretion signal or may be that of another protein, such as a milk protein. The term "secretion signal" is used herein to denote that portion of a protein that directs it through the secretory pathway of a cell to the outside. Secretion signals are most commonly found at the amino-termini of proteins. See, for example, von Heinje, Nuc. Acids Res. 14: 4683-4690, 1986; and Meade et al., U.S. Pat. No. 4,873,316, which are incorporated herein by reference.

Construction of expression units is conveniently carried out by inserting a fibrinogen chain sequence into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of a fibrinogen chain (including a secretion signal), thereby creating a gene fusion that includes the expression control sequences of the milk protein gene. In any event, cloning of the expression units in plasmids or other vectors facilitates the amplification of the fibrinogen sequences. Amplification is conveniently carried out in bacterial (e.g. E. coli) host cells, thus the vectors will typically include an origin of replication and a selectable marker functional in bacterial host cells.

In view of the size of the fibrinogen chain genes it is most practical to prepare three separate expression units, mix them, and introduce the mixture into the host. However, those skilled in the art will recognize that other protocols may be followed. For example, expression units for the three chains can be introduced individually into different embryos to be combined later by breeding. In a third approach, the three expression units can be linked in a single suitable vector, such as a yeast artificial chromosome or phage P1 clone. Coding sequences for two or three chains can be combined in polycistronic expression units (see, e.g., Levinson et al., U.S. Pat. No. 4,713,339).

The expression unit(s) is(are) then introduced into fertilized eggs (including early-stage embryos) of the chosen host species. Introduction of heterologous DNA can be accomplished by one of several routes, including microinjection (e.g. U.S. Pat. No 4,873,191), retroviral infection (Jaenisch, Science 240: 1468-1474, 1988) or site-directed integration using embryonic stem (ES) cells (reviewed by Bradley et al., Bio/Technology 10: 534-539, 1992). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds. General procedures for producing transgenic animals are known in the art. See, for example, Hogan et al., Manipulating the Mouse Embryo: A Laboratory Manual, Cold Spring Harbor Laboratory, 1986; Simons et al., Bio/Technology 6: 179-183, 1988; Wall et al., Biol. Reprod. 32: 645-651, 1985; Buhler et al., Bio/Technology: 140-143, 1990; Ebert et al., Bio/Technology: 835-838, 1991; Krimpenfort et al., Bio/Technology 9: 844-847, 1991; Wall et al. J. Cell. Biochem. 49: 113-120, 1992; and WIPO publications WO 88/00239, WO 90/05188, WO 92/11757; and GB 87/00458, which are incorporated herein by reference. Techniques for introducing foreign DNA sequences into mammals and their germ cells were originally developed in the mouse. See, e.g., Gordon et al., Proc. Natl. Acad. Sci. USA 77: 7380-7384, 1980; Gordon and Ruddle, Science 214: 1244-1246, 1981; Palmiter and Brinster, Cell 41: 343-345, 1985; Brinster et al., Proc. Natl. Acad. Sci. USA 82: 4438-1442, 1985; and Hogan et al. (ibid.). These techniques were subsequently adapted for use with larger animals, including livestock species (see e.g., WIPO publications WO 88/00239, WO 90/05188, and WO 92/11757; and Simons et al., Bio/Technology 6: 179-183, 1988). To summarize, in the most efficient route used to date in the generation of transgenic mice or livestock, several hundred linear molecules of the DNA of interest are injected into one of the pro-nuclei of a fertilized egg. Injection of DNA into the cytoplasm of a zygote can also be employed.

It is preferred to obtain a balanced expression of each fibrinogen chain to allow for efficient formation of the mature protein. Ideally, the three expression units should be on the same DNA molecule for introduction into eggs. This approach, however, may generate technical problems at, for example, the injection and manipulation stages. For example, the size of fibrinogen expression units may necessitate the use of yeast artificial chromosomes (YACs) or phage P1 to amplify and manipulate the DNA prior to injection. If this approach is followed, segments of DNA to be injected, containing all three expression units, would be very large, thus requiring modification of the injection procedure using, for example, larger bore needles. In a more simple approach, a mixture of each individual expression unit is used. It is preferred to combine equimolar amounts of the three expression units, although those skilled in the art will recognize that this ratio may be varied to compensate for the characteristics of a given expression unit. Some expression, generally a reduced level, will be obtained when lesser molar amounts of one or two chains are used, and expression efficiencies can generally be expected to decline in approximate proportion to the divergence from the preferred equimolar ratio. In any event, it is preferred to use a mixture having a ratio of Aα:Bβ:γ expression units in the range of 0.5-1:0.5-1:0.5-1. When the ratio is varied from equimolar, it is preferred to employ relatively more of the Bβ expression unit. Alternatively, one or a mixture of two of the expression units is introduced into individual eggs. However, animals derived by this approach will express only one or two fibrinogen chains. To generate an intact fibrinogen molecule by this approach requires a subsequent breeding program designed to combine all three expression units in individuals of a group of animals.

In general, female animals are superovulated by treatment with follicle stimulating hormone, then mated. Fertilized eggs are collected, and the heterologous DNA is injected into the eggs using known methods. See, for example, U.S. Pat No. 4,873,191; Gordon et al, Proc. Natl. Acad. Sci. USA 77: 7380-7384, 1980; Gordon and Ruddle, Science 214: 1244-1246, 1981; Palmiter and Brinster, Cell. 41: 343-345, 1985; Brinster et al., Proc. Natl. Acad. Sci. USA 82: 4438-4442, 1985; Hogan et al., Manipulating the Mouse Embryo: A Laboratory Manual, Cold Spring Harbor Laboratory, 1986; Simons et al. Bio/Technology 6:179-183, 1988; Wall et al., Biol. Reprod. 32: 645-651, 1985; Buhler et al., Bio/Technology 8: 140-143, 1990; Ebert et al., Bio/Technology 9: 835-838, 1991; Krimpenfort et al., Bio/Technology 9: 844-847, 1991; Wall et al., J. Cell. Biochem. 49: 113-120, 1992; WIPO publications WO 88/00239, WO 90/05118, and WO 92/11757; and GB 87/00458, which are incorporated herein by reference.

For injection into fertilized eggs, the expression units are removed from their respective vectors by digestion with appropriate restriction enzymes. For convenience, it is preferred to design the vectors to that the expression units are removed by cleavage with enzymes that do not cut either within the expression units or elsewhere in the vectors. The expression units are recovered by conventional methods, such as electro-elution followed by phenol extraction and ethanol precipitation, sucrose density gradient centrifugation, or combinations of these approaches.

DNA is injected into eggs essentially as described in Hogan et al., ibid. In a typical injection, eggs in a dish of an embryo culture medium are located using a stereo room microscope (×50 or ×63 magnification preferred). Suitable media include Hepes (N-2-hydroxyethylpiperazine-N'-2-ethanesulphonic acid) or bicarbonate buffered media such as M2 or M16 (available from Sigma Chemical Co., St Louis, USA) or synthetic oviduct medium (disclosed below). The eggs are secured and transferred to the center of a glass slide on an injection rig using, for example, a drummond pipette complete with capillary tube. Viewing at lower (e.g. ×4) magnification is used at this stage. Using the holding pipette of the injection rig, the eggs are positioned centrally on the slide. Individual eggs are sequentially secured to the holding pipette for injection. For each injection process, the holding pipette/egg is positioned in the center of the viewing field. The injection needle is then positioned directly below the egg. Preferably using ×40 Nomarski objectives, both manipulator heights are adjusted to focus both the egg and the needle. The pronuclei are located by rotating the egg and adjusting the holding pipette assembly as necessary. Once the pronucleus has been located, the height of the manipulator is altered to focus the pronuclear membrane. The injection needle is positioned below the egg such that the needle tip is in a position below the center of the pronucleus. The position of the needle is then altered using the injection manipulator assembly to bring the needle and the pronucleus into the same focal plane. The needle is moved, via the joy stick on the injection manipulator assembly, to a position to the right of the egg. With a short, continuous jabbing movement, the pronuclear membrane is pierced to leave the needle tip inside the pronucleus. Pressure is applied to the injection needle via the glass syringe until the pronucleus swells to approximately twice its volume. At this point, the needle is slowly removed. Reverting to lower (e.g. ×4) magnification, the injected egg is moved to a different area of the slide, and the process is repeated with another egg.

After the DNA is injected, the eggs may be cultured to allow the pronuclei to fuse, producing one-cell or later stage embryos. In general, the eggs are cultured at approximately the body temperature of the species used in a buffered medium containing balanced salts and serum. Surviving embryos are then transferred to pseudopregnant recipient females, typically by inserting them into the oviduct or uterus, and allowed to develop to term. During embryogenesis, the injected DNA integrates in a random fashion in the genomes of a small number of the developing embryos.

Potential transgenic offspring are screened via blood samples and/or tissue biopsies. DNA is prepared from these samples and examined for the presence of the injected construct by techniques such as polymerase chain reaction (PCR; see Mullis, U.S. Pat. No. 4,683,202) and Southern blotting (Southern, J. Mol. Biol. 98:503, 1975; Maniatis et al., Molecular Cloning: A Laboratory Manual, Cold Spring Harbor Laboratory, 1982). Founder transgenic animals, or G0s, may be wholly transgenic, having transgenes in all of their cells, or mosaic, having transgenes in only a subset of cells (see, for example, Wilkie et al., Develop. Biol. 118: 9-18, 1986). In the latter case, groups of germ cells may be wholly or partially transgenic. In the latter case, the number of transgenic progeny from a founder animal will be less than the expected 50% predicted from Mendelian principles. Founder G0 animals are grown to sexual maturity and mated to obtain offspring, or G1s. The G1s are also examined for the presence of the transgene to demonstrate transmission from founder G0 animals. In the case of male G0s, these may be mated with several non-transgenic females to generate many offspring. This increases the chances of observing transgene transmission. Female G0 founders may be mated naturally, artificially inseminated or superovulated to obtain many eggs which are transferred to surrogate mothers. The latter course gives the best chance of observing transmission in animals having a limited number of young. The above-described breeding procedures are used to obtain animals that can pass the DNA on to subsequent generations of offspring in the normal, Mendelian fashion, allowing the development of, for example, colonies (mice), flocks (sheep), or herds (pigs, goats and cattle) of transgenic animals.

The milk from lactating G0 and G1 females is examined for the expression of the heterologous protein using immunological techniques such as ELISA (see Harlow and Lane, Antibodies, A Laboratory Manual, Cold Spring Harbor Laboratory, 1988) and Western blotting (Towbin et al., Proc. Natl. Acad. Sci. USA 76: 4350-4354, 1979). For a variety of reasons known in the art, expression levels of the heterologous protein will be expected to differ between individuals.

A satisfactory family of animals should satisfy three criteria: they should be derived from the same founder G0 animal; they should exhibit stable transmission of the transgene; and they should exhibit stable expression levels from generation to generation and from lactation to lactation of individual animals. These principles have been demonstrated and discussed (Carver et al., Bio/Technology 11: 1263-1270, 1993). Animals from such a suitable family are referred to as a "line." Initially, male animals, G0 or G1, are used to derive a flock or herd of producer animals by natural or artificial insemination. In this way, many female animals containing the same transgene integration event can be quickly generated from which a supply of milk can be obtained.

The fibrinogen is recovered from milk using standard practices such as skimming, precipitation, filtration and protein chromatography techniques.

Fibrinogen produced according to the present invention is useful within human and veterinary medicine, such as in the formulation of surgical adhesives. Adhesives of this type are known in the art. See, for example, U.S. Pat. Nos. 4,377,572; 4,442,655; 4,462,567; and 4,627,879, which are incorporated herein by reference. In general, fibrinogen and factor XIII are combined to form a first component that is mixed just prior to use with a second component containing thrombin. The thrombin converts the fibrinogen to fibrin, causing the mixture to gel, and activates the factor XIII. The activated factor XIII cross links the fibrin to strengthen and stabilize the adhesive matrix. Such adhesives typically contain from about 30 mg/ml to about 100 mg/ml fibrinogen and from about 50 μg/ml to about 500 μg/ml factor XIII. They may also contain additional ingredients, such as aprotinin, albumin, fibronectin, bulking agents, and solubilizers. Methods for producing factor XIII are known in the art. See, for example, U.S. Pat No. 5,204,447. The fibrinogen is also useful for coating surfaces of polymeric articles, e.g. synthetic vascular grafts, as disclosed in U.S. Pat. No. 5,272,074 (incorporated herein by reference).

The invention is further illustrated by the following non-limiting examples.

EXAMPLES

Example I

The multiple cloning site of the vector pUC18 (Yanisch-Perron et al., Gene 33:103-119, 1985) was removed and replaced with a synthetic double stranded oligonucleotide (the strands of which are shown in SEQ ID NO: 8 and SEQ ID NO: 27) containing the restriction sites Pvu I/Mlu I/Eco RV/Xba I/Pvu I/Mlu I, and flanked by 5' overhangs compatible with the restriction sites Eco RI and Hind III. pUC18 was cleaved with both Eco RI and Hind III, the 5' terminal phosphate groups were removed with calf intestinal phosphatase, and the oligonucleotide was ligated into the vector backbone. The DNA sequence across the junction was confirmed by sequencing, and the new plasmid was called pUCPM.

The β-lactoglobulin (BLG) gene sequences from pSS1tgXS (disclosed in WIPO publication WO 88/00239) were excised as a Sal I-Xba I fragment and recloned into the vector pUCPM that had been cut with Sal I and Xba I to construct vector pUCXS. pUCXS is thus a pUC18 derivative containing the entire BLG gene from the Sal I site to the Xba I site of phage SS1 (Ali and Clark, J. Mol. Biol. 199: 415-426, 1988).

The plasmid pSS1tgSE (disclosed in WIPO publication WO 88/00239) contains a 1290 bp BLG fragment flanked by Sph I and EcoR I restriction sites, a region spanning a unique Not I site and a single Pvu II site which lies in the 5' untranslated leader of the BLG mRNA. Into this Pvu II site was ligated a double stranded, 8 bp DNA linker (5'-GGATATCC-3') encoding the recognition site for the enzyme Eco RV. This plasmid was called pSS1tgSE/RV. DNA sequences bounded by Sph I and Not I restriction sites in pSS1tgSE/RV were excised by enzymatic digestion and used to replace the equivalent fragment in pUCXS. The resulting plasmid was called pUCXSRV. The sequence of the BLG insert in pUCSXRV is shown in SEQ ID NO: 7, with the unique Eco RV site at nucleotide 4245 in the 5' untranslated leader region of the BLG gene. This site allows insertion of any additional DNA sequences under the control of the BLG promoter 3' to the transcription initiation site.

Using the primers BLGAMP3 (5'-TGG ATC CCC TGC CGG TGC CTC TGG-3'; SEQ ID NO: 9) and BLGAMP4 (5'-AAC GCG TCA TCC TCT GTG AGC CAG-3'; SEQ ID NO: 10) a PCR fragment of approximately 650 bp was produced from sequences immediately 3' to the stop codon of the BLG gene in pUCXSRV. The PCR fragment was engineered to have a BamH I site at its 5' end and an Mlu I site at its 3' end and was cloned as such into BamH I and Mlu I cut pGEM7zf (+) (Promega) to give pDAM200(+).

pUCXSRV was digested with Kpn I, and the largest, vector containing band was gel purified. This band contained the entire pUC plasmid sequences and some 3' non-coding sequences from the BLG gene. Into this backbone was ligated the small Kpn I fragment from pDAM200(+) which, in the correct orientation, effectively engineered a BamH I site at the extreme 5' end of the 2.6 Kbp of the BLG 3' flanking region. This plasmid was called pBLAC200. A 2.6 Kbp Cla I-Xba I fragment from pBLAC200 was ligated into Cla I-Xba I cut pSP72 vector (Promega), thus placing an EcoR V site immediately upstream of the BLG sequences. This plasmid was called pBLAC210.

The 2.6 Kbp Eco RV-Xba I fragment from pBLAC210 was ligated into Eco RV-Xba I cut pUCXSRV to form pMAD6. This, in effect, excised all coding and intron sequences from pUCXSRV, forming a BLG minigene consisting of 4.3 Kbp of 5' promoter and 2.6 Kbp of 3' downstream sequences flanking a unique EcoR V site. An oligonucleotide linker (ZC6839: ACTACGTAGT; SEQ ID NO: 11) was inserted into the Eco RV site of pMAD6. This modification destroyed the Eco RV site and created a Sna BI site to be used for cloning purposes. The vector was designated pMAD6-Sna. Messenger RNA initiates upstream of the Sna BI site and terminates downstream of the Sna BI site. The precursor transcript will encode a single BLG-derived intron, intron 6, which is entirely within the 3' untranslated region of the gene.

Example II

Clones encoding the individual fibrinogen chains were obtained from the laboratory of Dr. Earl W. Davie, University of Washington, Seattle. A genomic fibrinogen Aα-chain clone (Chung et al., 1990, ibid.) was obtained from the plasmid BS4. This plasmid contains the Aα clone inserted into the Sal I and Bam HI sites of the vector pUC18, but lacks the coding sequence for the first four amino acids of the Aα chain. A genomic Bβ-chain DNA (Chung et al., ibid.) was isolated from a lambda Charon 4A phage clone (designated βλ4) as two EcoRI fragments of ca. 5.6 Kbp each. The two fragments were cloned separately into pUC19 that had been digested with Eco RI and treated with calf intestinal phosphatase. The resulting clones were screened by digestion with the restriction enzyme Pvu II to distinguish plasmids with the 5' and 3' Bp inserts (designated Beta5'RI/puc and Beta3'RI/puc, respectively). Genomic γ-chain clones were isolated as described by Rixon et al. (Biochemistry 24: 2077-2086, 1985). Clone pγ12A9 comprises 5' non-coding sequences and approximately 4535 bp of γ-chain coding sequence. Clone pγ12F3 comprises the remaining coding sequence and 3' non-coding nucleotides. Both are pBR322-based plasmids with the fibrinogen sequences inserted at the EcoRI site. These plasmids were used as templates for the respective PCR reactions.

The fibrinogen chain coding sequences were tailored for insertion into expression vectors using the polymerase chain reaction (PCR) as generally described by Mullis (U.S. Pat. No. 4,683,202). This procedure removed native 5' and 3' untranslated sequences, added a 9 base sequence (CCT GCA GCC) upstream of the first ATG of each coding sequence, supplied the first four codons for the Aα-chain sequence, removed an internal Mlu I site in the Aα sequence and added restriction sites to facilitate subsequent cloning steps.

Referring to FIG. 1, the 5' end of the Aα coding sequence was tailored in a PCR reaction containing 20 pmole for each of primers ZC6632 (SEQ ID NO: 12) and ZC6627 (SEQ ID NO: 13), approximately 10 ng of plasmid BS4 template DNA, 10 μl of a mix containing 2.5 mM each dNTP, 7.5 μl 10× Pyrococcus furiosus (Pfu) DNA polymerase buffer #1 (200 mM Tris-HCl, pH 8.2, 100 mM KCl, 60 mM $(NH_4)_2SO_4$, 20 mM $MgCl_2$, 1% Triton X-100, 100 μg/ml nuclease free bovine serum albumin)(Stratagene, La Jolla, Calif.), and water to 75 μl. The mixture was heated to 94° C. in a DNA thermal cycler (Perkin-Elmer Corp., Norwalk, Conn.). To the heated mixture was added 25 μl of a mixture containing 2.5 μl 10×Pfu buffer #1, 22 μl $H_2O$ and 1 μl 2.5 units/μl Pfu DNA polymerase (Stratagem). The reactions were run in a DNA thermal cycler (Perkin-Elmer) for five cycles of 94°, 45 seconds; 40°, 90 seconds; 72°, 120 seconds; 20 cycles of 94°, 45 seconds; 45°, 90 seconds; 72°, 120 seconds; then incubated at 72° for 7 minutes. The 5' PCR-generated fragment was digested with Bam HI and Hind III, and the Bam HI-Hind III fragment was then ligated to an internal 2.91 Kbp Hind III-Xba I fragment and Bam HI, Xba I-digested pUC18. PCR-generated exon sequences were sequenced.

Referring again to FIG. 1, the 3' end of the Aα coding sequence was tailored in a series of steps in which the Mlu I site 563 bases upstream from the stop codon of the Aα sequence was mutated using an overlap extension PCR reaction (Ho et al., Gene 77: 51-59, 1989). In the first reaction 40 pmole of each of primers ZC6521 (SEQ ID NO: 14) and ZC6520 (SEQ ID NO: 15) were combined with approximately 10 ng of plasmid BS4 template DNA in a reaction mixture as described above. The reaction was run for 5 cycles of 94°, 45 seconds; 40°, 60 seconds; 72°, 120 seconds; 15 cycles of 94°, 45 seconds; 45°, 60 seconds; 72°, 120 seconds; then incubated at 72° for 7 minutes. A second reaction was carried out in the same manner using 40 pmole of each of primers ZC6519 (SEQ ID NO: 16) and ZC6518 (SEQ ID NO: 17) and BS4 as template. The PCR-generated DNA fragments from the first and second reactions were isolated by gel electrophoresis and elution from the gel. Approximately 1/10 of each recovered reaction product was combined with 40 pmole of each of primers ZC6521 (SEQ ID NO: 14) and ZC6518 (SEQ ID NO: 17) in a PCR reaction in which the complementary 3' ends of each fragment (containing the single base change) annealed and served as a primer for the 3' extension of the complementary strand. PCR was carried out using the same reaction conditions as in the first and second 3' PCR steps. The reaction product was then digested with Xba I and Bam HI, and the Xba I-Bam HI fragment was cloned into Xba I, Bam HI-digested pUC18. PCR-generated exons were sequenced.

Figure 2:
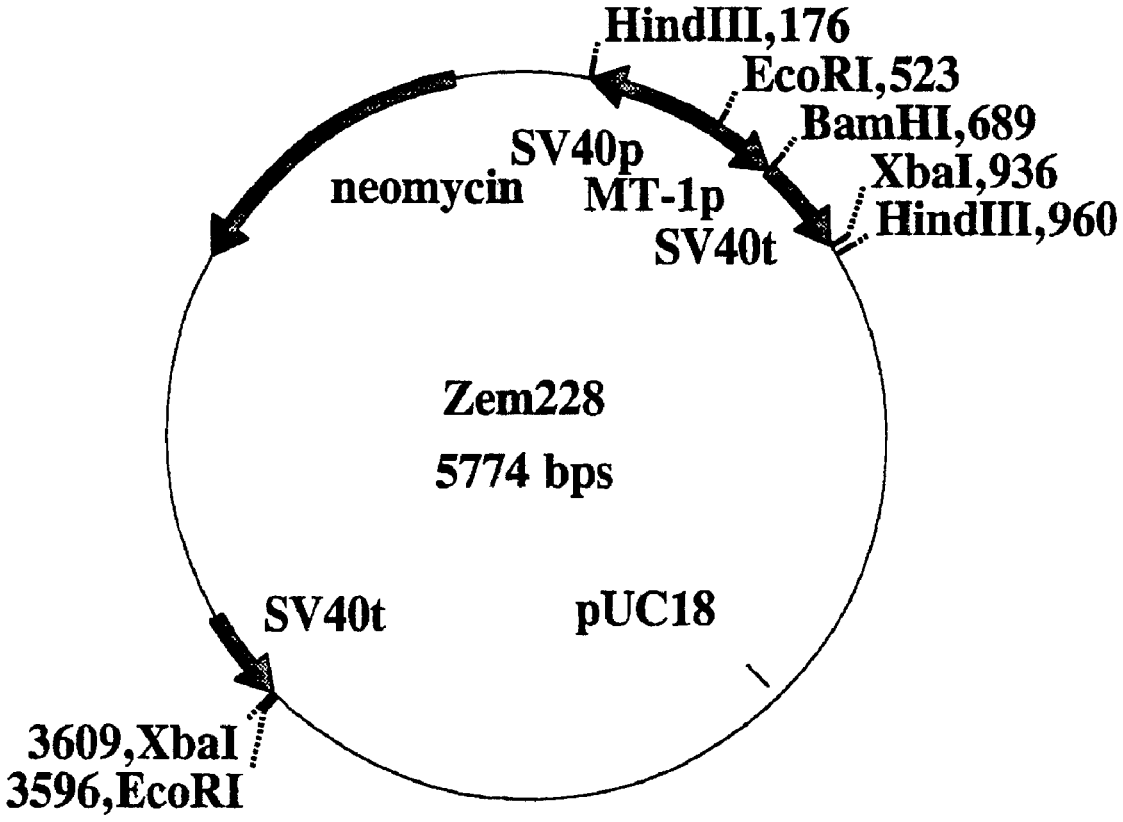
FIG. 2 is a partial restriction map of the vector Zem228. Symbols used are MT-1p, mouse metallothionein promoter; SV40t, SV40 terminator; and SV40p, SV40 promoter.

As shown in FIG. 1, the 5' Bam HI-Xba I fragment (3.9 Kbp) and the 3' Xba I-Bam HI fragment (1.3 Kbp) were inserted into the Bam HI site of the vector Zem228. Zem228 is a pUC18 derivative comprising a Bam HI cloning site between a mouse MT-1 promoter and SV40 terminator, and a neomycin resistance marker flanked by SV40 promoter and terminator sequences. See European Patent Office Publication EP 319,944 and FIG. 2. The entire Aα coding sequence was isolated from the Zem228 vector as an Sna BI fragment, which was inserted into the Sna BI site of the plasmid pMAD6-Sna.

Figure 3:
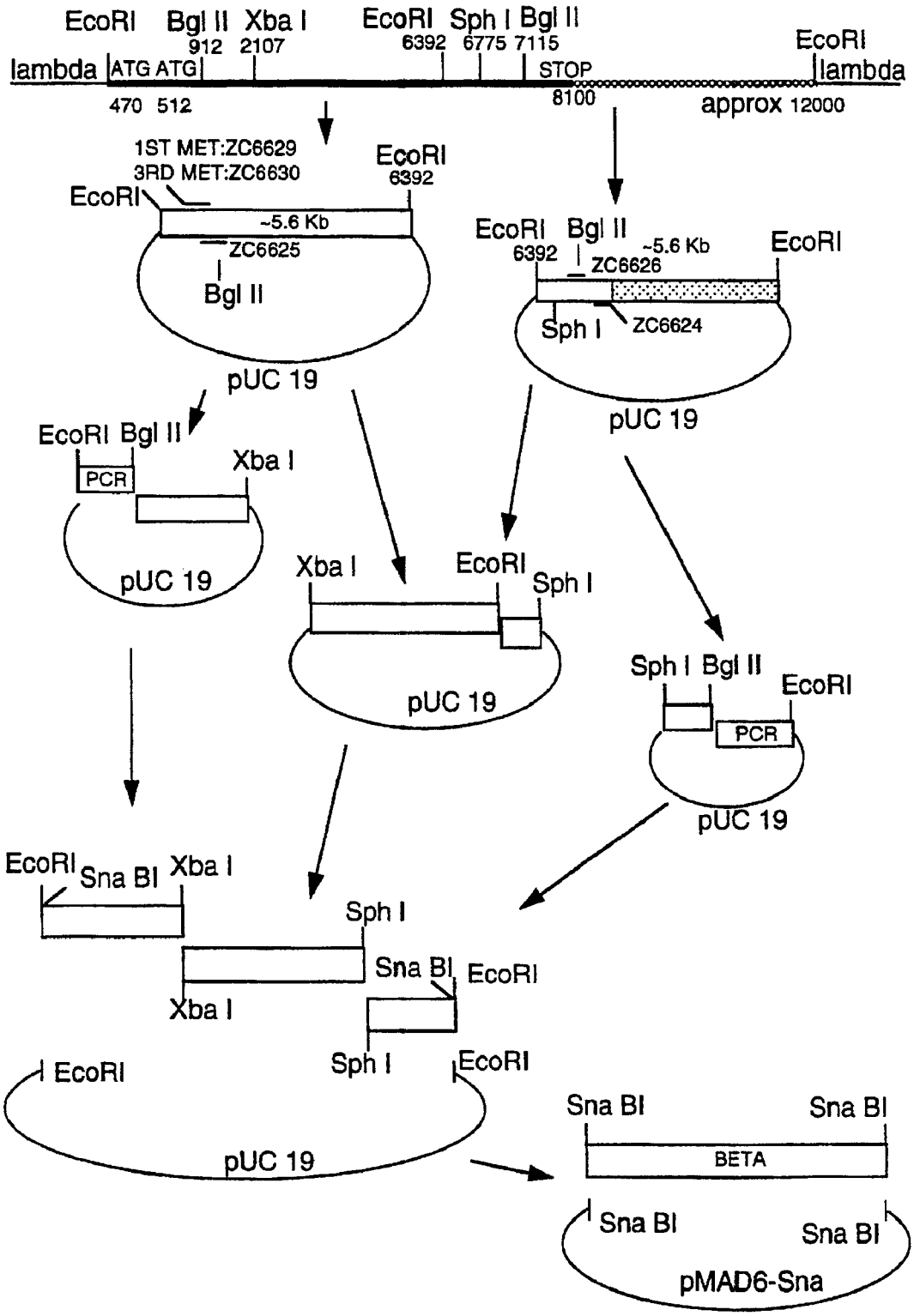
FIG. 3 illustrates the subcloning of a human fibrinogen Bβ chain DNA sequence.

Referring to FIG. 3, the 5' end of the Bβ-chain was tailored by PCR using the oligonucleotides ZC6629 (SEQ ID NO: 18), ZC6630 (SEQ ID NO: 19) and ZC6625 (SEQ ID NO: 20). These primers were used in pairwise combinations (ZC6629+ZC6625 or ZC6630+ZC6625) to generate Bβ coding sequences beginning at the first ATG codon (position 470 in SEQ ID NO: 3)(designated N1-Beta) or the third ATG codon (position 512 in SEQ ID NO: 3)(designated N3-Beta). Approximately 5 ng of Beta5'RI/puc template DNA was combined with 20 pmole of each of the primers (N1-Beta: ZC6629, SEQ ID NO: 18+ZC6625, SEQ ID NO: 20; or N3-Beta:ZC6630, SEQ ID NO: 19+ZC6625, SEQ ID NO: 20) in a reaction mixture as described above. The mixtures were incubated for 5 cycles of 94°, 45 seconds; 40°, 120 seconds; (N1-Beta) or 90 seconds (N3-Beta); 72°, 120 seconds; 20 cycles of 94°, 45 seconds; 45°, 120 seconds; (N1-Beta) or 90 seconds (N3-Beta); 72°, 120 seconds; then incubated at 72° for 7 minutes. The two reaction products N1, 555 bp or N3, 510 bp) were each digested with Eco RI and Bgl II, and the fragments were ligated to the internal Bgl II-Xba I fragment and Eco RI+Xba I-digested pUC19. The 3' end of the Bβ sequence was tailored in a reaction mixture as described above using the oligonucleotide primers ZC6626 (SEQ ID NO: 21) and ZC6624 (SEQ ID NO: 22) and approximately 5 ng of Beta3'RI/puc template. The mixtures were incubated for 5 cycles of 94°, 45 seconds; 40°, 90 seconds; 72°, 120 seconds; 15 cycles of 94°, 45 seconds; 45°, 90 seconds; 72°, 120 seconds; then incubated at 72° for 7 minutes. A 990 bp Bgl II-Eco RI fragment was isolated. This 3' fragment was ligated to the adjacent coding fragment (340 bp, SphI-Bgl II) and Sph I+Eco RI-digested pUC19. The 3' and 5' PCR-generated exons were sequenced. A third intermediate vector was constructed by combining two internal fragments (4285 bp Xba I-Eco RI and 383 kb Eco RI-Sph I) in Xba I+Sph I-digested pUC19. The entire Bβ coding sequence (two forms) was then assembled by ligating one of the 5' Eco RI-Xba I fragments, the internal Xba I-Sph I fragment, the 3' Sph I-Eco RI fragment and Eco RI-digested vector pUC19. The Bβ sequence was then isolated as a 7.6 Kbp Sna BI fragment and inserted into the Sna BI site of pMAD6-Sna.

Figure 4:
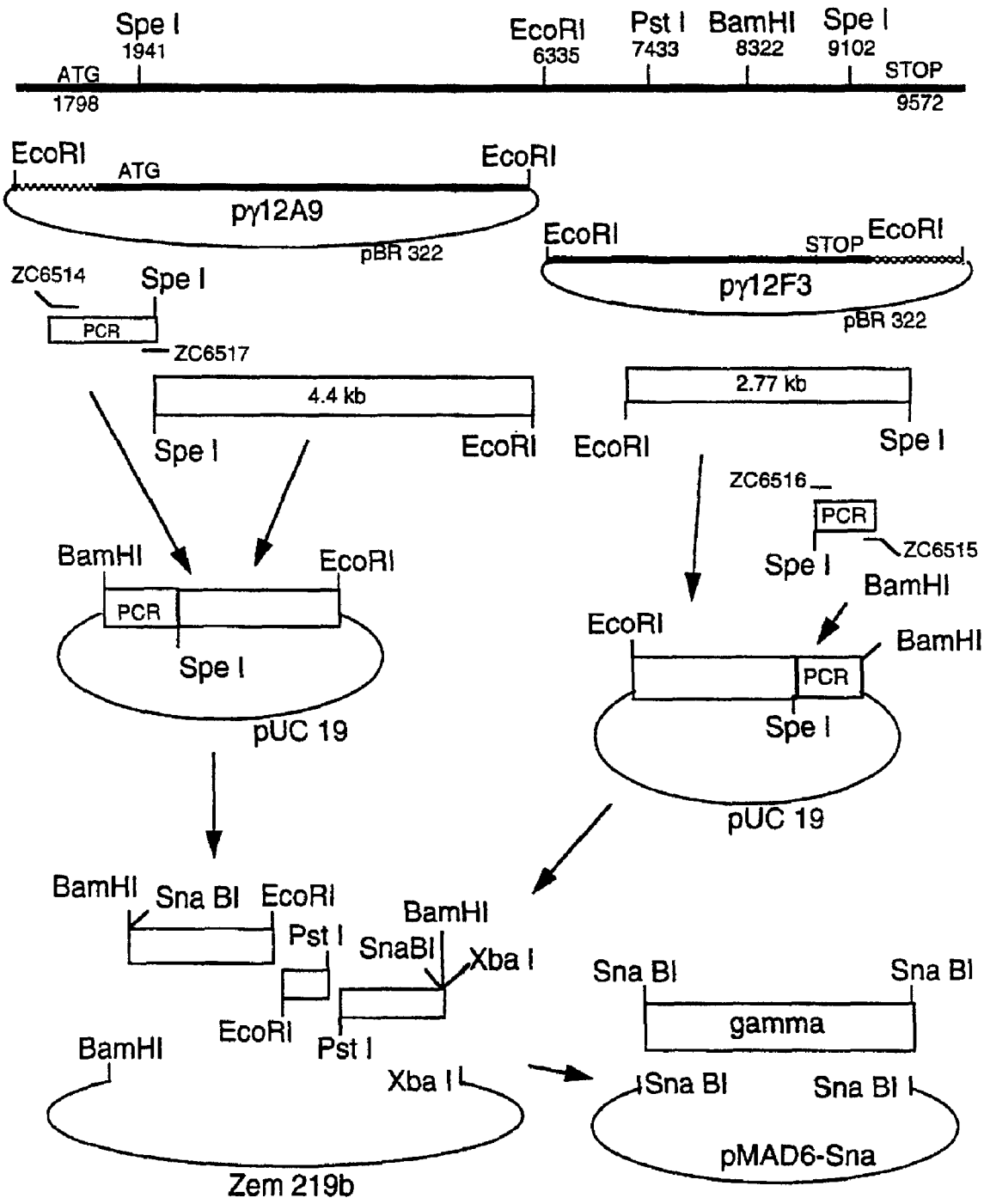
FIG. 4 illustrates the subcloning of a human fibrinogen γ chain DNA sequence.

Referring to FIG. 4, the 5' end of the gamma chain sequence was tailored by PCR using the oligonucleotide primers ZC6514 (SEQ ID NO: 23) and ZC6517 (SEQ ID NO: 24) and approximately 50 ng of pγ12A9 as template. The PCR reaction was run as described above using 40 pM of each primer. The reaction was run for 5 cycles of 94°, 45 seconds; 40°, 60 seconds, 72°, 120 seconds, followed by 15 cycles of 94°, 45 seconds; 45°, 60 seconds; 72°, 120 seconds. The resulting 213 by fragment was digested with Bam HI and Spe I, and the resulting restriction fragment was ligated with the adjacent downstream 4.4 kb Spe I-Eco RI fragment and Bam HI+Eco RI digested pUC19. The 3' end of the gamma chain sequence was tailored using oligonucleotide primers ZC6516 (SEQ ID NO: 25) and ZC6515 (SEQ ID NO: 26) using 40 pM of each primer, approximately 50 ng of pγ12F3 template and the same thermal cycling schedule as used for the 5' fragment.

Figure 5:
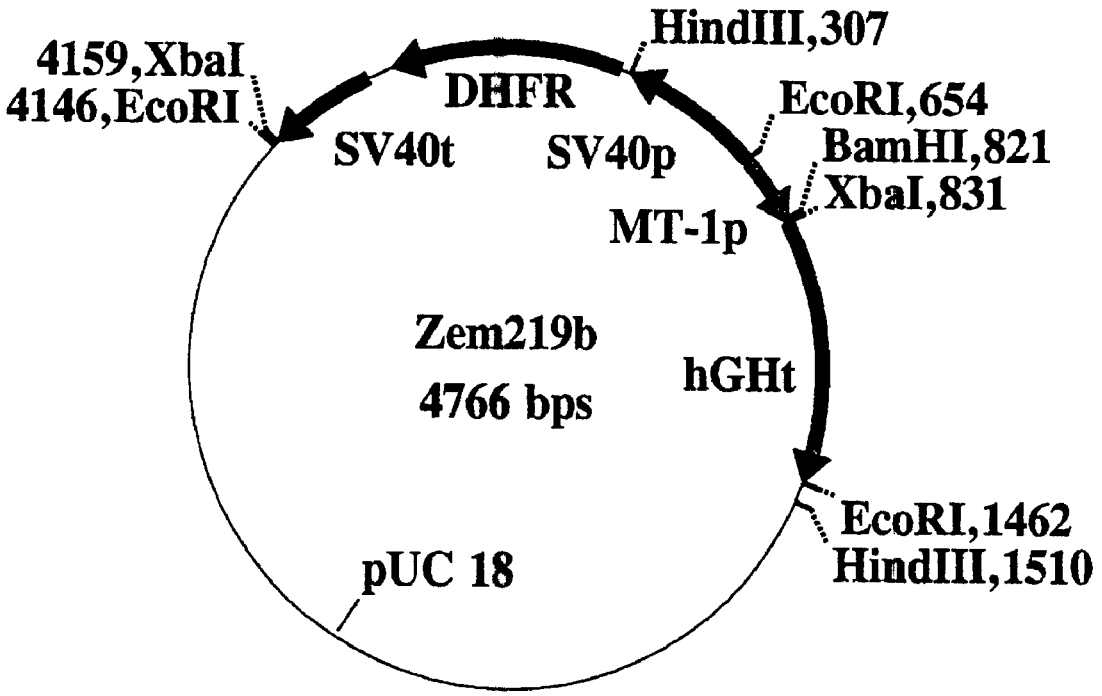
FIG. 5 is a partial restriction map of the vector Zem219b. Symbols used are MT-1p, mouse metallothionein promoter; hGHt, human growth hormone terminator; SV40p, SV40 promoter; DHFR, dihydrofolate reductase gene; and SV40t, SV40 terminator.

The resulting 500 bp fragment was digested with Spe I and Bam HI, and the resulting restriction fragment was ligated with the upstream 2.77 kb Eco RI-Spe I fragment and Eco RI+Bam HI-digested pUC19. All PCR-generated exons were sequenced. The entire γ'-chain coding sequence was then assembled by ligating a 4.5 Kbp Bam HI-Eco RI 5' fragment, a 1.1 Kbp Eco RI-Pst I internal fragment and a 2.14 Kbp Pst I-Xba I 3' fragment in Bam HI+Xba I-digested Zem219b. Zem219b is a pUC18-derived vector containing a mouse metallothionein promoter and a DHFR selectable marker operably linked to an SV40 promoter (FIG. 5). Plasmid Zem219b has been deposited with American Type Culture Collection as an E. coli XL1-blue transformant under Accession No. 68979. The entire γ-chain coding sequence was then isolated as a 7.8 Kbp Sna B1 fragment and inserted into the Sna BI site of pMAD6-Sna.

Example III

Mice for initial breeding stocks (C57BL6J, CBACA) were obtained from Harlan Olac Ltd. (Bicester, UK). These were mated in pairs to produce F1 hybrid cross (B6CBAF1) for recipient female, superovulated females, stud males and vasectomized males. All animals were kept on a 14 hour light/10 hour dark cycle and fed water and food (Special Diet Services RM3, Edinburgh, Scotland) ad libitum.

Transgenic mice were generated essentially as described in Hogan et al., Manipulating the Mouse Embryo: A Laboratory Manual, Cold Spring Harbor Laboratory, 1986, which is incorporated herein by reference in its entirety. Female B6CBAF1 animals were superovulated at 4-5 weeks of age by an i.p. injection of pregnant mares' serum gonadotrophin (FOLLIGON, Vet-Drug, Falkirk, Scotland) (5 iu) followed by an i.p. injection of human chorionic gonadotrophin (CHORULON, Vet-Drug, Falkirk, Scotland) (5 iu) 45 hours later. They were then mated with a stud male overnight. Such females were next examined for copulation plugs. Those that had mated were sacrificed, and their eggs were collected for microinjection.

DNA was injected into the fertilized eggs as described in Hogan et al. (ibid.) Briefly, each of the vectors containing the Aα, Bβ and γ expression units was digested with Mlu I, and the expression units were isolated by sucrose gradient centrifugation. All chemicals used were reagent grade (Sigma Chemical Co., St. Louis, Mo., U.S.A.), and all solutions were sterile and nuclease-free. Solutions of 20% and 40% sucrose in 1M NaCl, 20 mM Tris pH 8.0, 5 mM EDTA were prepared using UHP water and filter sterilized. A 30% sucrose solution was prepared by mixing equal volumes of the 20% and 40% solutions. A gradient was prepared by layering 0.5 ml steps of the 40%, 30% and 20% sucrose solutions into a 2 ml polyallomer tube and allowed to stand for one hour. 100 μl of DNA solution (max. 8 μg DNA) was loaded onto the top of the gradient, and the gradient was centrifuged for 17-20 hours at 26,000 rpm, 15° C. in a Beckman TL100 ultracentrifuge using a TLS-55 rotor (Beckman Instruments, Fullerton, Calif., USA). Gradients were fractionated by puncturing the tube bottom with a 20 ga. needle and collecting drops in a 96 well microliter plate. 3 μl aliquots were analyzed on a 1% agarose mini-gel. Fractions containing the desired DNA fragment were pooled and ethanol precipitated overnight at −20° C. in 0.3M sodium acetate. DNA pellets were resuspended in 50-100 μl UHP water and quantitated by fluorimetry. The expression units were diluted in Dulbecco's phosphate buffered saline without calcium and magnesium (containing, per liter, 0.2 g KCl, 0.2 g $KH_2PO_4$, 8.0 g NaCl, 1.15 g $Na_2HPO_4$), mixed (using either the N1-Beta or N3-Beta expression unit) in a 1:1:1 molar ratio, concentration adjusted to about 6 μg/ml, and injected into the eggs (~2 pl total DNA solution per egg).

Recipient females of 6-8 weeks of age are prepared by mating B6CBAF1 females in natural estrus with vasectomized males. Females possessing copulation plugs are then kept for transfer of microinjected eggs.

Following birth of potential transgenic animals, tail biopsies are taken, under anesthesia, at four weeks of age. Tissue samples are placed in 2 ml of tail buffer (0.3M Na acetate, 50 mM HCl, 1.5 mM $MgCl_2$, 10 mM Tris-HCl, pH 8.5, 0.5% NP40, 0.5% Tween 20) containing 200 μg/ml proteinase K (Boehringer Mannheim, Mannheim, Germany) and vortexed. The samples are shaken (250 rpm) at 55°-60° for 3 hours to overnight. DNA prepared from biopsy samples is examined for the presence of the injected constructs by PCR and Southern blotting. The digested tissue is vigorously vortexed, and 5 μl aliquots are placed in 0.5 ml microcentrifuge tubes. Positive and negative tail samples are included as controls. Forty μl of silicone oil (BDH, Poole, UK) is added to each tube, and the tubes are briefly centrifuged. The tubes are incubated in the heating block of a thermal cycler (e.g. Omni-gene, Hybaid, Teddington, UK) to 95° C. for 10 minutes. Following this, each tube has a 45 μl aliquot of PCR mix added such that the final composition of each reaction mix is: 50 mM KCl; 2 mM $MgCl_2$; 10 mM Tris-HCl (pH 8.3); 0.01% gelatin; 0.1% NP40, 10% DMSO; 500 nM each primer, 200 μM dNTPs; 0.02 U/μl Taq polymerase (Boehringer Mannheim, Mannheim, Germany). The tubes are then cycled through 30 repeated temperature changes as required by the particular primers used. The primers may be varied but in all cases must target the BLG promoter region. This is specific for the injected DNA fragments because the mouse does not have a BLG gene. Twelve μl of 5× loading buffer containing Orange G marker dye (0.25% Orange G [Sigma] 15% Ficoll type 400 [Pharmacia Biosystems Ltd., Milton Keynes, UK]) is then added to each tube, and the reaction mixtures are electrophoresed on a 1.6% agarose gel containing ethidium bromide (Sigma) until the marker dye has migrated ⅔ of the length of the gel. The gel is visualized with a UV light source emitting a wavelength of 254 nm. Transgenic mice having one or more of the injected DNA fragments are identified by this approach.

Positive tail samples are processed to obtain pure DNA. The DNA samples are screened by Southern blotting using a BLG promoter probe (nucleotides 2523-4253 of SEQ ID NO: 7). Specific cleavages with appropriate restriction enzymes (e.g. Eco RI) allow the distinction of the three constructs containing the Aα, Bβ and γ sequences.

Southern blot analysis of transgenic mice prepared essentially as described above demonstrated that more than 50% of progeny contained all three fibrinogen sequences. Examination of milk from positive animals by reducing SDS polyacrylamide gel electrophoresis demonstrated the presence of all three protein chains at concentrations up to 1 mg/ml. The amount of fully assembled fibrinogen was related to the ratios of individual subunits present in the milk. No apparent phenotype was associated with high concentrations of human fibrinogen in mouse milk.

Example IV

Donor ewes are treated with an intravaginal progesterone-impregnated sponge (CHRONOGEST Goat Sponge, Intervet, Cambridge, UK) on day 0. Sponges are left in situ for ten or twelve days.

Superovulation is induced by treatment of donor ewes with a total of one unit of ovine follicle stimulating hormone (OFSH) (OVAGEN, Horizon Animal Reproduction Technology Pty. Ltd., New Zealand) administered in eight intramuscular injections of 0.125 units per injection starting at 5:00 pm on day −4 and ending at 8:00 am on day 0. Donors are injected intramuscularly with 0.5 ml of a luteolytic agent (ESTRU- MATE, Vet-Drug) on day −4 to cause regression of the corpus luteum, to allow return to estrus and ovulation. To synchronize ovulation, the donor animals are injected intramuscularly with 2 ml of a synthetic releasing hormone analog (RECEPTAL, Vet-Drug) at 5:00 pm on day 0.

Donors are starved of food and water for at least 12 hours before artificial insemination (A.I.). The animals are artificially inseminated by intrauterine laparoscopy under sedation and local anesthesia on day 1. Either xylazine (ROMPUN, Vet-Drug) at a dose rate of 0.05-0.1 ml per 10 kg bodyweight or ACP injection 10 mg/ml (Vet-Drug) at a dose rate of 0.1 ml per 10 kg bodyweight is injected intramuscularly approximately fifteen minutes before A.I. to provide sedation. A.I. is carried out using freshly collected semen from a Poll Dorset ram. Semen is diluted with equal parts of filtered phosphate buffered saline, and 0.2 ml of the diluted semen is injected per uterine horn. Immediately pre- or post-A.I., donors are given an intramuscular injection of AMOXYPEN (Vet-Drug).

Fertilized eggs are recovered on day 2 following starvation of donors of food and water from 5:00 pm on day 1. Recovery is carried out under general anesthesia induced by an intravenous injection of 5% thiopentone sodium (INTRAVAL SODIUM, Vet-Drug) at a dose rate of 3 ml per 10 kg bodyweight. Anesthesia is maintained by inhalation of 1-2% Halothane/$O_2$/$N_2O$ after intubation. To recover the fertilized eggs, a laparotomy incision is made, and the uterus is exteriorized. The eggs are recovered by retrograde flushing of the oviducts with Ovum Culture Medium (Advanced Protein Products, Brierly Hill, West Midlands, UK) supplemented with bovine serum albumin of New Zealand origin. After flushing, the uterus is returned to the abdomen, and the incision is closed. Donors are allowed to recover post-operatively or are euthanized. Donors that are allowed to recover are given an intramuscular injection of Amoxypen L.A. at the manufacturer's recommended dose rate immediately pre- or post-operatively.

Plasmids containing the three fibrinogen chain expression units are digested with Mlu I, and the expression unit fragments are recovered and purified on sucrose density gradients. The fragment concentrations are determined by fluorimetry and diluted in Dulbecco's phosphate buffered saline without calcium and magnesium as described above. The concentration is adjusted to 6 μg/ml and approximately 2 pl of the mixture is microinjected into one pronucleus of each fertilized eggs with visible pronuclei.

All fertilized eggs surviving pronuclear microinjection are cultured in vitro at 38.5° C. in an atmosphere of 5% $CO_2$:5% $O_2$:90% $N_2$ and about ~100% humidity in a bicarbonate buffered synthetic oviduct medium (see Table) supplemented with 20% v/v vasectomized ram serum. The serum may be heat inactivated at 56° C. for 30 minutes and stored frozen at −20° C. prior to use. The fertilized eggs are cultured for a suitable period of time to allow early embryo mortality (caused by the manipulation techniques) to occur. These dead or arrested embryos are discarded. Embryos having developed to 5 or 6 cell divisions are transferred to synchronized recipient ewes.

TABLE

| Synthetic Oviduct Medium | |
|---|---|
| Stock A (Lasts 3 Months) | |
| NaCl | 6.29 g |
| KCl | 0.534 g |
| $KH_2SO_4$ | 0.162 g |
| $MgSO_4$:$7H_2O$ | 0.182 g |
| Penicillin | 0.06 g |
| Sodium Lactate 60% syrup | 0.6 mls |
| Super $H_2O$ | 99.4 mls |

TABLE-continued

| Synthetic Oviduct Medium | |
|---|---|
| Stock B (Lasts 2 weeks) | |
| $NaHCO_3$ | 0.21 g |
| Phenol red | 0.001 g |
| Super $H_2O$ | 10 mls |
| Stock C (Lasts 2 weeks) | |
| Sodium Pyruvate | 0.051 g |
| Super $H_2O$ | 10 mls |
| Stock D (Lasts 3 months) | |
| $CaCl_2$•$2H_2O$ | 0.262 g |
| Super $H_2O$ | 10 mls |
| Stock E (Lasts 3 months) | |
| Hepes | 0.651 g |
| Phenol red | 0.001 g |
| Super $H_2O$ | 10 mls |
| To make up 10 mls of Bicarbonate Buffered Medium | |
| STOCK A | 1 ml |
| STOCK B | 1 ml |
| STOCK C | 0.07 ml |
| STOCK D | 0.1 ml |
| Super $H_2O$ | 7.83 ml |
| Osmolarity should be 265-285 mOsm. Add 2.5 ml of heat inactivated sheep serum and filter sterilize. | |
| To make up 10 mls HEPES Buffered Medium | |
| STOCK A | 1 ml |
| STOCK B | 0.2 ml |
| STOCK C | 0.07 ml |
| STOCK D | 0.1 ml |
| STOCK E | 0.8 ml |
| Super $H_2O$ | 7.83 ml |
| Osmolarity should be 265-285 mOsm. Add 2.5 ml of heat inactivated sheep serum and filter sterilize. | |

Recipient ewes are treated with an intravaginal progesterone-impregnated sponge (Chronogest Ewe Sponge or Chronogest Ewe-Lamb Sponge, Intervet) left in situ for 10 or 12 days. The ewes are injected intramuscularly with 1.5 ml (300 iu) of a follicle stimulating hormone substitute (P.M.S.G., Intervet) and with 0.5 ml of a luteolytic agent (Estrumate, Coopers Pitman-Moore) at sponge removal on day −1. The ewes are tested for estrus with a vasectomized ram between 8:00 am and 5:00 pm on days 0 and 1.

Embryos surviving in vitro culture are returned to recipients (starved from 5:00 pm on day 5 or 6) on day 6 or 7. Embryo transfer is carried out under general anesthesia as described above. The uterus is exteriorized via a laparotomy incision with or without laparoscopy. Embryos are returned to one or both uterine horns only in ewes with at least one suitable corpora lutea. After replacement of the uterus, the abdomen is closed, and the recipients are allowed to recover. The animals are given an intramuscular injection of Amoxypen L.A. at the manufacturer's recommended dose rate immediately pre- or post-operatively.

Lambs are identified by ear tags and left with their dams for rearing. Ewes and lambs are either housed and fed complete diet concentrates and other supplements and or ad lib. hay, or are let out to grass.

Within the first week of life (or as soon thereafter as possible without prejudicing health), each lamb is tested for the presence of the heterologous DNA by two sampling procedures. A 10 ml blood sample is taken from the jugular vein into an EDTA vacutainer. If fit enough, the lambs also have a second 10 ml blood sample taken within one week of the first.

Tissue samples are taken by tail biopsy as soon as possible after the tail has become desensitized after the application of a rubber elastrator ring to its proximal third (usually within 200 minutes after "tailing"). The tissue is placed immediately in a solution of tail buffer. Tail samples are kept at room temperature and analyzed on the day of collection. All lambs are given an intramuscular injection of Amoxypen L.A. at the manufacturer's recommended dose rate immediately post-biopsy, and the cut end of the tail is sprayed with an antibiotic spray.

DNA is extracted from sheep blood by first separating white blood cells. A 10 ml sample of blood is diluted in 20 ml of Hank's buffered saline (HBS; obtained from Sigma Chemical Co.). Ten ml of the diluted blood is layered over 5 ml of Histopaque (Sigma) in each of two 15 ml screw-capped tubes. The tubes are centrifuged at 3000 rpm (2000×g max.), low brake for 15 minutes at room temperature. White cell interfaces are removed to a clean 15 ml tube and diluted to 15 ml in HBS. The diluted cells are spun at 3000 rpm for 10 minutes at room temperature, and the cell pellet is recovered and resuspended in 2-5 ml of tail buffer.

To extract DNA from the white cells, 10% SDS is added to the resuspended cells to a final concentration of 1%, and the tube is inverted to mix the solution. One mg of fresh proteinase K solution is added, and the mixture is incubated overnight at 45° C. DNA is extracted using an equal volume of phenol/chloroform (×3) and chloroform/isoamyl alcohol (×1). The DNA is then precipitated by adding 0.1 volume of 3M NaOAc and 2 volumes of ethanol, and the tube is inverted to mix. The precipitated DNA is spooled out using a clean glass rod with a sealed end. The spool is washed in 70% ethanol, and the DNA is allowed to partially dry, then is redissolved in TE (10 mM Tris-HCl, 1 mM EDTA, pH 7.4).

DNA samples from blood and tail are analyzed by Southern blotting using probes for the BLG promoter region and the fibrinogen chain coding regions.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

SEQUENCE LISTING

```
(1) GENERAL INFORMATION:

   (iii) NUMBER OF SEQUENCES: 27


(2) INFORMATION FOR SEQ ID NO: 1:

     (i) SEQUENCE CHARACTERISTICS:
          (A) LENGTH: 5943 base pairs
          (B) TYPE: nucleic acid
          (C) STRANDEDNESS: double
          (D) TOPOLOGY: linear

    (ii) MOLECULE TYPE: DNA (genomic)

   (vii) IMMEDIATE SOURCE:
          (B) CLONE: Human Fibrinogen A-alpha chain

    (ix) FEATURE:
          (A) NAME/KEY: CDS
          (B) LOCATION: join(31..84, 1154..1279, 1739..1922, 3055..3200,
               3786..5210)

    (xi) SEQUENCE DESCRIPTION: SEQ ID NO: 1:

GTCTAGGAGC CAGCCCCACC CTTAGAAAAG ATG TTT TCC ATG AGG ATC GTC TGC      54
                                 Met Phe Ser Met Arg Ile Val Cys
                                   1               5

CTA GTT CTA AGT GTG GTG GGC ACA GCA TGG GTATGGCCCT TTTCATTTTT        104
Leu Val Leu Ser Val Val Gly Thr Ala Trp
     10                  15

TCTTCTTGCT TTCTCTCTGG TGTTTATTCC ACAAAGAGCC TGGAGGTCAG AGTCTACCTG    164

CTCTATGTCC TGACACACTC TTAGCTTTAT GACCCCAGGC CTGGGAGGAA ATTTCCTGGG    224

TGGGCTTGAC ACCTCAAGAA TACAGGGTAA TATGACACCA AGAGGAAGAT CTTAGATGGA    284

TGAGAGTGTA CAACTACAAG GGAAACTTTA GCATCTGTCA TTCAGTCTTA CCACATTTTG    344

TTTTGTTTTG TTTTAAAAAG GGCAAGAATT ATTTGCCATC CTTGTACCTA TAAAGCCTTG    404

GTGCATTATA ATGCTAGTTA ATGGAATAAA ACATTTTATG GTAAGATTTG TTTTCTTTAG    464

TTATTAATTT CTTGCTACTT GTCCATAATA AGCAGAACTT TTAGTGTTAG TACAGTTTTG    524

CTGAAAGGTT ATTGTTGTGT TTGTCAAGAC AGAAGAAAAA GCAAACGAAT TATCTTTGGA    584

AATATCTTTG CAGTATCAGA AGAGATTAGT TAGTAAGGCA ATACGCTTTT CCGCAGTAAT    644
```

-continued

```
GGTATTCTTT TAAATTATGA ATCCATCTCT AAAGGTTACA TAGAAACTTG AAGGAGAGAG    704

GAACATTCAG TTAAGATAGT CTAGGTTTTT CTACTGAAGC AGCAATTACA GGAGAAAGAG    764

CTCTACAGTA GTTTTCAACT TTCTGTCTGC AGTCATTAGT AAAAATGAAA AGGTAAAATT    824

TAACTGATTT TATAGATTCA AATAATTTTC CTTTTAGGAT GGATTCTTTA AAACTCCTAA    884

TATTTATCAA ATGCTTATTT AAGTGTCACA CACAGTTAAG AAATTTGTAC ACCTTGTCTC    944

CTTTAATTCT CATAACAACT CCATAAAATG GGTCCTAGGA TTTCCATTTG AAGATAAGAA   1004

ACCTGAAGCT TGCCGAAGCC CTGTGTCTGC TCTCCTTAAT CTCTGTGAGA GTGCCATCTC   1064

TTCCTGGGGA CTTGTAGGCA TGCCACTGTC TCCTCTTCTG GCTAACATTG CTGTTGCTCT   1124

CTTTTGTGTA TGTGAATGAA TCTTTAAAG ACT GCA GAT AGT GGT GAA GGT GAC     1177
                                Thr Ala Asp Ser Gly Glu Gly Asp
                                     20                  25

TTT CTA GCT GAA GGA GGA GGC GTG CGT GGC CCA AGG GTT GTG GAA AGA     1225
Phe Leu Ala Glu Gly Gly Gly Val Arg Gly Pro Arg Val Val Glu Arg
            30                  35                  40

CAT CAA TCT GCC TGC AAA GAT TCA GAC TGG CCC TTC TGC TCT GAT GAA     1273
His Gln Ser Ala Cys Lys Asp Ser Asp Trp Pro Phe Cys Ser Asp Glu
        45                  50                  55

GAC TGG GTAAGCAGTC AGCGGGGGAA GCAGGAGATT CCTTCCCTCT GATGCTAGAG      1329
Asp Trp
    60

GGGCTCACAG GCTGACCTGA TTGGTCCCAG AAACTTTTTT AAATAGAAAA TAATTGAATA   1389

GTTACCTACA TAGCAAATAA AGAAAAGGAA CCTACTCCCA AGAGCACTGT TTATTTACCT   1449

CCCCAACTCT GGATCATTAG TGGGTGAACA GACAGGATTT CAGTTGCATG CTCAGGCAAA   1509

ACCAGGCTCC TGAGTATTGT GGCCTCAATT TCCTGGCACC TATTTATGGC TAAGTGGACC   1569

CTCATTCCAG AGTTTCTCTG CGACCTCTAA CTAGTCCTCT TACCTACTTT TAAGCCAACT   1629

TATCTGGAAG AGAAAGGGTA GGAAGAAATG GGGGCTGCAT GGAAACATGC AAAATTATTC   1689

TGAATCTGAG AGATAGATCC TTACTGTAAT TTTCTCCCTT CACTTTCAG AAC TAC       1744
                                                      Asn Tyr

AAA TGC CCT TCT GGC TGC AGG ATG AAA GGG TTG ATT GAT GAA GTC AAT     1792
Lys Cys Pro Ser Gly Cys Arg Met Lys Gly Leu Ile Asp Glu Val Asn
        65                  70                  75

CAA GAT TTT ACA AAC AGA ATA AAT AAG CTC AAA AAT TCA CTA TTT GAA     1840
Gln Asp Phe Thr Asn Arg Ile Asn Lys Leu Lys Asn Ser Leu Phe Glu
    80                  85                  90

TAT CAG AAG AAC AAT AAG GAT TCT CAT TCG TTG ACC ACT AAT ATA ATG     1888
Tyr Gln Lys Asn Asn Lys Asp Ser His Ser Leu Thr Thr Asn Ile Met
95                  100                 105                 110

GAA ATT TTG AGA GGC GAT TTT TCC TCA GCC AAT  A GTAAGTATTA           1932
Glu Ile Leu Arg Gly Asp Phe Ser Ser Ala Asn
                115                 120

CATATTTACT TCTTTGACTT TATAACAGAA ACAACAAAAA TCCTAAATAA ATATGATATC   1992

CGCTTATATC TATGACAATT TCATCCCAAA GTACTTAGTG TAGAAACACA TACCTTCATA   2052

ATATCCCTGA AAATTTTAAG AGGGAGCTTT TGTTTTCGTT ATTTTTTCAA AGTAAAAGAT   2112

GTTAACTGAG ATTGTTTAAG GTCACAAAAT AAGTCAGAAT TTTGGATTAA AACAAGAATT   2172

TAAATGTGTT CTTTTCAACA GTATATACTG AAAGTAGGAT GGGTCAGACT CTTTGAGTTG   2232

ATATTTTTGT TTCTGCTTTG TAAAGGTGAA AACTGAGAGG TCAAGGAACT TGTTCAAAGA   2292

CACAGAGCTG GGAATTCAAC TCCCAGACTC CACTGAGCTG ATTAGGTAGA TTTTTAAATT   2352

TAAAATATAG GGTCAAGCTA CGTCATTCTC ACAGTCTACT CATTAGGGTT AGGAAACATT   2412

GCATTCACTC TGGGCATGGA CAGCGAGTCT AGGGAGTCCT CAGTTTCTCA AGTTTTGCTT   2472
```

```
TGCCTTTTTA CACCTTCACA AACACTTGAC ATTTAAAATC AGTGATGCCA ACACTAGCTG   2532

GCAAGTGAGT GATCCTGTTG ACCCAAAACA GCTTAGGAAC CATTTCAAAT CTATAGAGTT   2592

AAAAAGAAAA GCTCATCAGT AAGAAAATCC AATATGTTCA AGTCCCTTGA TTAAGGATGT   2652

TATAAAATAA TTGAAATGCA ATCAAACCAA CTATTTTAAC TCCAAATTAC ACCTTTAAAA   2712

TTCCAAAGAA AGTTCTTCTT CTATATTTCT TTGGGATTAC TAATTGCTAT TAGGACATCT   2772

TAACTGGCAT TCATGGAAGG CTGCAGGGCA TAACATTATC CAAAAGTCAA ATGCCCCATA   2832

GGTTTTGAAC TCACAGATTA AACTGTAACC AAAATAAAAT TAGGCATATT TACAAGCTAG   2892

TTTCTTTCTT TCTTTTTTCT CTTTCTTTCT TTCTTTCTTT CTTTCTTTCT TTCTTTCTTT   2952

CTTTCTTTCT TTCTCCTTCC TTCCTTTCTT CCTTTCTTTT TTGCTGGCAA TTACAGACAA   3012

ATCACTCAGC AGCTACTTCA ATAACCATAT TTTCGATTTC AG  AC CGT GAT AAT      3065
                                               Asn Arg Asp Asn
                                                           125

ACC TAC AAC CGA GTG TCA GAG GAT CTG AGA AGC AGA ATT GAA GTC CTG     3113
Thr Tyr Asn Arg Val Ser Glu Asp Leu Arg Ser Arg Ile Glu Val Leu
                130                 135                 140

AAG CGC AAA GTC ATA GAA AAA GTA CAG CAT ATC CAG CTT CTG CAG AAA     3161
Lys Arg Lys Val Ile Glu Lys Val Gln His Ile Gln Leu Leu Gln Lys
            145                 150                 155

AAT GTT AGA GCT CAG TTG GTT GAT ATG AAA CGA CTG GAG GTAAGTATGT      3210
Asn Val Arg Ala Gln Leu Val Asp Met Lys Arg Leu Glu
        160                 165                 170

GGCTGTGGTC CCGAGTGTCC TTGTTTTTGA GTAGAGGGAA AAGGAAGGCG ATAGTTATGC   3270

ACTGAGTGTC TACTATATGC AGAGAAAAGT GTTATATCCA TCATCTACCT AAAAGTAGGT   3330

ATTATTTTCC TCACTCCACA GTTGAAGAAA AAAAAATTCA GAGATATTAA GTAAATTTTC   3390

CAACGTACAT AGATAGTAAT TCAAAGCAAT GTTCAGTCCC TGTCTATTCC AAGCCATTAC   3450

ATCACCACAC CTCTGAGCCC TCAGCCTGAG TTCACCAAGG ATCATTTAAT TAGCGTTTCC   3510

TTTGAGAGGG AATAGCACCT TACTCTTGAT CCATTCTGAG GCTAAGATGA ATTAAACAGC   3570

ATCCATTGCT TATCCTGGCT AGCCCTGCAA TACCCAACAT CTCTTCCACT GAGGGTGCTC   3630

GATAGGCAGA AAACAGAGAA TATTAAGTGG TAGGTCTCCG AGTCAAAAAA AATGAAACCA   3690

GTTTCCAGAA GGAAAATTAA CTACCAGGAA CTCAATAGAC GTAGTTTATG TATTTGTATC   3750

TACATTTTCT CTTTATTTTT CTCCCCTCTC TCTAG GTG GAC ATT GAT ATT AAG      3803
                                       Val Asp Ile Asp Ile Lys
                                                           175

ATC CGA TCT TGT CGA GGG TCA TGC AGT AGG GCT TTA GCT CGT GAA GTA     3851
Ile Arg Ser Cys Arg Gly Ser Cys Ser Arg Ala Leu Ala Arg Glu Val
            180                 185                 190

GAT CTG AAG GAC TAT GAA GAT CAG CAG AAG CAA CTT GAA CAG GTC ATT     3899
Asp Leu Lys Asp Tyr Glu Asp Gln Gln Lys Gln Leu Glu Gln Val Ile
        195                 200                 205

GCC AAA GAC TTA CTT CCC TCT AGA GAT AGG CAA CAC TTA CCA CTG ATA     3947
Ala Lys Asp Leu Leu Pro Ser Arg Asp Arg Gln His Leu Pro Leu Ile
    210                 215                 220

AAA ATG AAA CCA GTT CCA GAC TTG GTT CCC GGA AAT TTT AAG AGC CAG     3995
Lys Met Lys Pro Val Pro Asp Leu Val Pro Gly Asn Phe Lys Ser Gln
225                 230                 235                 240

CTT CAG AAG GTA CCC CCA GAG TGG AAG GCA TTA ACA GAC ATG CCG CAG     4043
Leu Gln Lys Val Pro Pro Glu Trp Lys Ala Leu Thr Asp Met Pro Gln
                245                 250                 255

ATG AGA ATG GAG TTA GAG AGA CCT GGT GGA AAT GAG ATT ACT CGA GGA     4091
Met Arg Met Glu Leu Glu Arg Pro Gly Gly Asn Glu Ile Thr Arg Gly
            260                 265                 270
```

```
GGC TCC ACC TCT TAT GGA ACC GGA TCA GAG ACG GAA AGC CCC AGG AAC     4139
Gly Ser Thr Ser Tyr Gly Thr Gly Ser Glu Thr Glu Ser Pro Arg Asn
        275                 280                 285

CCT AGC AGT GCT GGA AGC TGG AAC TCT GGG AGC TCT GGA CCT GGA AGT     4187
Pro Ser Ser Ala Gly Ser Trp Asn Ser Gly Ser Ser Gly Pro Gly Ser
    290                 295                 300

ACT GGA AAC CGA AAC CCT GGG AGC TCT GGG ACT GGA GGG ACT GCA ACC     4235
Thr Gly Asn Arg Asn Pro Gly Ser Ser Gly Thr Gly Gly Thr Ala Thr
305                 310                 315                 320

TGG AAA CCT GGG AGC TCT GGA CCT GGA AGT GCT GGA AGC TGG AAC TCT     4283
Trp Lys Pro Gly Ser Ser Gly Pro Gly Ser Ala Gly Ser Trp Asn Ser
                325                 330                 335

GGG AGC TCT GGA ACT GGA AGT ACT GGA AAC CAA AAC CCT GGG AGC CCT     4331
Gly Ser Ser Gly Thr Gly Ser Thr Gly Asn Gln Asn Pro Gly Ser Pro
            340                 345                 350

AGA CCT GGT AGT ACC GGA ACC TGG AAT CCT GGC AGC TCT GAA CGC GGA     4379
Arg Pro Gly Ser Thr Gly Thr Trp Asn Pro Gly Ser Ser Glu Arg Gly
        355                 360                 365

AGT GCT GGG CAC TGG ACC TCT GAG AGC TCT GTA TCT GGT AGT ACT GGA     4427
Ser Ala Gly His Trp Thr Ser Glu Ser Ser Val Ser Gly Ser Thr Gly
    370                 375                 380

CAA TGG CAC TCT GAA TCT GGA AGT TTT AGG CCA GAT AGC CCA GGC TCT     4475
Gln Trp His Ser Glu Ser Gly Ser Phe Arg Pro Asp Ser Pro Gly Ser
385                 390                 395                 400

GGG AAC GCG AGG CCT AAC AAC CCA GAC TGG GGC ACA TTT GAA GAG GTG     4523
Gly Asn Ala Arg Pro Asn Asn Pro Asp Trp Gly Thr Phe Glu Glu Val
                405                 410                 415

TCA GGA AAT GTA AGT CCA GGG ACA AGG AGA GAG TAC CAC ACA GAA AAA     4571
Ser Gly Asn Val Ser Pro Gly Thr Arg Arg Glu Tyr His Thr Glu Lys
            420                 425                 430

CTG GTC ACT TCT AAA GGA GAT AAA GAG CTC AGG ACT GGT AAA GAG AAG     4619
Leu Val Thr Ser Lys Gly Asp Lys Glu Leu Arg Thr Gly Lys Glu Lys
        435                 440                 445

GTC ACC TCT GGT AGC ACA ACC ACC ACG CGT CGT TCA TGC TCT AAA ACC     4667
Val Thr Ser Gly Ser Thr Thr Thr Thr Arg Arg Ser Cys Ser Lys Thr
    450                 455                 460

GTT ACT AAG ACT GTT ATT GGT CCT GAT GGT CAC AAA GAA GTT ACC AAA     4715
Val Thr Lys Thr Val Ile Gly Pro Asp Gly His Lys Glu Val Thr Lys
465                 470                 475                 480

GAA GTG GTG ACC TCC GAA GAT GGT TCT GAC TGT CCC GAG GCA ATG GAT     4763
Glu Val Val Thr Ser Glu Asp Gly Ser Asp Cys Pro Glu Ala Met Asp
                485                 490                 495

TTA GGC ACA TTG TCT GGC ATA GGT ACT CTG GAT GGG TTC CGC CAT AGG     4811
Leu Gly Thr Leu Ser Gly Ile Gly Thr Leu Asp Gly Phe Arg His Arg
            500                 505                 510

CAC CCT GAT GAA GCT GCC TTC TTC GAC ACT GCC TCA ACT GGA AAA ACA     4859
His Pro Asp Glu Ala Ala Phe Phe Asp Thr Ala Ser Thr Gly Lys Thr
        515                 520                 525

TTC CCA GGT TTC TTC TCA CCT ATG TTA GGA GAG TTT GTC AGT GAG ACT     4907
Phe Pro Gly Phe Phe Ser Pro Met Leu Gly Glu Phe Val Ser Glu Thr
    530                 535                 540

GAG TCT AGG GGC TCA GAA TCT GGC ATC TTC ACA AAT ACA AAG GAA TCC     4955
Glu Ser Arg Gly Ser Glu Ser Gly Ile Phe Thr Asn Thr Lys Glu Ser
545                 550                 555                 560

AGT TCT CAT CAC CCT GGG ATA GCT GAA TTC CCT TCC CGT GGT AAA TCT     5003
Ser Ser His His Pro Gly Ile Ala Glu Phe Pro Ser Arg Gly Lys Ser
                565                 570                 575

TCA AGT TAC AGC AAA CAA TTT ACT AGT AGC ACG AGT TAC AAC AGA GGA     5051
Ser Ser Tyr Ser Lys Gln Phe Thr Ser Ser Thr Ser Tyr Asn Arg Gly
            580                 585                 590
```

```
GAC TCC ACA TTT GAA AGC AAG AGC TAT AAA ATG GCA GAT GAG GCC GGA     5099
Asp Ser Thr Phe Glu Ser Lys Ser Tyr Lys Met Ala Asp Glu Ala Gly
        595                 600                 605

AGT GAA GCC GAT CAT GAA GGA ACA CAT AGC ACC AAG AGA GGC CAT GCT     5147
Ser Glu Ala Asp His Glu Gly Thr His Ser Thr Lys Arg Gly His Ala
    610                 615                 620

AAA TCT CGC CCT GTC AGA GGT ATC CAC ACT TCT CCT TTG GGG AAG CCT     5195
Lys Ser Arg Pro Val Arg Gly Ile His Thr Ser Pro Leu Gly Lys Pro
625                 630                 635                 640

TCC CTG TCC CCC TAGACTAAGT TAAATATTTC TGCACAGTGT TCCCATGGCC         5247
Ser Leu Ser Pro

CCTTGCATTT CCTTCTTAAC TCTCTGTTAC ACGTCATTGA AACTACACTT TTTTGGTCTG   5307

TTTTTGTGCT AGACTGTAAG TTCCTTGGGG GCAGGGCCTT TGTCTGTCTC ATCTCTGTAT   5367

TCCCAAATGC CTAACAGTAC AGAGCCATGA CTCAATAAAT ACATGTTAAA TGGATGAATG   5427

AATTCCTCTG AAACTCTATT TGAGCTTATT TAGTCAAATT CTTTCACTAT TCAAAGTGTG   5487

TGCTATTAGA ATTGTCACCC AACTGATTAA TCACATTTTT AGTATGTGTC TCAGTTGACA   5547

TTTAGGTCAG GCTAAATACA AGTTGTGTTA GTATTAAGTG AGCTTAGCTA CCTGTACTGG   5607

TTACTTGCTA TTAGTTTGTG CAAGTAAAAT TCCAAATACA TTTGAGGAAA ATCCCCTTTG   5667

CAATTTGTAG GTATAAATAA CCGCTTATTT GCATAAGTTC TATCCCACTG TAAGTGCATC   5727

CTTTCCCTAT GGAGGGAAGG AAAGGAGGAA GAAAGAAAGG AAGGGAAAGA AACAGTATTT   5787

GCCTTATTTA ATCTGAGCCG TGCCTATCTT TGTAAAGTTA AATGAGAATA ACTTCTTCCA   5847

ACCAGCTTAA TTTTTTTTTT AGACTGTGAT GATGTCCTCC AAACACATCC TTCAGGTACC   5907

CAAAGTGGCA TTTTCAATAT CAAGCTATCC GGATCC                             5943
```

(2) INFORMATION FOR SEQ ID NO: 2:

(i) SEQUENCE CHARACTERISTICS:
(A) LENGTH: 644 amino acids
(B) TYPE: amino acid
(D) TOPOLOGY: linear (ii) MOLECULE TYPE: protein (xi) SEQUENCE DESCRIPTION: SEQ ID NO: 2:

```
Met Phe Ser Met Arg Ile Val Cys Leu Val Leu Ser Val Val Gly Thr
  1               5                  10                  15

Ala Trp Thr Ala Asp Ser Gly Glu Gly Asp Phe Leu Ala Glu Gly Gly
             20                  25                  30

Gly Val Arg Gly Pro Arg Val Val Glu Arg His Gln Ser Ala Cys Lys
         35                  40                  45

Asp Ser Asp Trp Pro Phe Cys Ser Asp Glu Asp Trp Asn Tyr Lys Cys
     50                  55                  60

Pro Ser Gly Cys Arg Met Lys Gly Leu Ile Asp Glu Val Asn Gln Asp
 65                  70                  75                  80

Phe Thr Asn Arg Ile Asn Lys Leu Lys Asn Ser Leu Phe Glu Tyr Gln
                 85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
    130                 135                 140

Val Ile Glu Lys Val Gln His Ile Gln Leu Leu Gln Lys Asn Val Arg
145                 150                 155                 160
```

```
Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205

Ala Lys Asp Leu Leu Pro Ser Arg Asp Arg Gln His Leu Pro Leu Ile
    210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
        275                 280                 285

Pro Ser Ser Ala Gly Ser Trp Asn Ser Gly Ser Ser Gly Pro Gly Ser
    290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Ala Gly Ser Trp Asn Ser
                325                 330                 335

Gly Ser Ser Gly Thr Gly Ser Thr Gly Asn Gln Asn Pro Gly Ser Pro
            340                 345                 350

Arg Pro Gly Ser Thr Gly Thr Trp Asn Pro Gly Ser Ser Glu Arg Gly
        355                 360                 365

Ser Ala Gly His Trp Thr Ser Glu Ser Ser Val Ser Gly Ser Thr Gly
    370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415

Ser Gly Asn Val Ser Pro Gly Thr Arg Arg Glu Tyr His Thr Glu Lys
            420                 425                 430

Leu Val Thr Ser Lys Gly Asp Lys Glu Leu Arg Thr Gly Lys Glu Lys
        435                 440                 445

Val Thr Ser Gly Ser Thr Thr Thr Thr Arg Arg Ser Cys Ser Lys Thr
    450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
            500                 505                 510

His Pro Asp Glu Ala Ala Phe Phe Asp Thr Ala Ser Thr Gly Lys Thr
        515                 520                 525

Phe Pro Gly Phe Phe Ser Pro Met Leu Gly Glu Phe Val Ser Glu Thr
    530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
            580                 585                 590
```

```
Asp Ser Thr Phe Glu Ser Lys Ser Tyr Lys Met Ala Asp Glu Ala Gly
        595                 600                 605

Ser Glu Ala Asp His Glu Gly Thr His Ser Thr Lys Arg Gly His Ala
    610                 615                 620

Lys Ser Arg Pro Val Arg Gly Ile His Thr Ser Pro Leu Gly Lys Pro
625                 630                 635                 640

Ser Leu Ser Pro
```

(2) INFORMATION FOR SEQ ID NO: 3:

(i) SEQUENCE CHARACTERISTICS:
(A) LENGTH: 8878 base pairs
(B) TYPE: nucleic acid
(C) STRANDEDNESS: double
(D) TOPOLOGY: linear (ii) MOLECULE TYPE: DNA (genomic)

(vii) IMMEDIATE SOURCE:
(B) CLONE: human fibrinogen B-beta chain (ix) FEATURE:
(A) NAME/KEY: misc_RNA
(B) LOCATION: 1..469

(ix) FEATURE:
(A) NAME/KEY: exon
(B) LOCATION: 470..583

(ix) FEATURE:
(A) NAME/KEY: intron
(B) LOCATION: 584..3257

(ix) FEATURE:
(A) NAME/KEY: exon
(B) LOCATION: 3258..3449

(ix) FEATURE:
(A) NAME/KEY: intron
(B) LOCATION: 3450..3938

(ix) FEATURE:
(A) NAME/KEY: exon
(B) LOCATION: 3939..4122

(ix) FEATURE:
(A) NAME/KEY: intron
(B) LOCATION: 4123..5042

(ix) FEATURE:
(A) NAME/KEY: exon
(B) LOCATION: 5043..5270

(ix) FEATURE:
(A) NAME/KEY: intron
(B) LOCATION: 5271..5830

(ix) FEATURE:
(A) NAME/KEY: exon
(B) LOCATION: 5831..5944

(ix) FEATURE:
(A) NAME/KEY: intron
(B) LOCATION: 5945..6632

(ix) FEATURE:
(A) NAME/KEY: exon
(B) LOCATION: 6633..6758

(ix) FEATURE:
(A) NAME/KEY: intron
(B) LOCATION: 6759..6966

(ix) FEATURE:
(A) NAME/KEY: exon
(B) LOCATION: 6967..7252

```
    (ix) FEATURE:
          (A) NAME/KEY: intron
          (B) LOCATION: 7253..7870

    (ix) FEATURE:
          (A) NAME/KEY: exon
          (B) LOCATION: 7871..8102

    (ix) FEATURE:
          (A) NAME/KEY: 3'UTR
          (B) LOCATION: 8103..8537

    (ix) FEATURE:
          (A) NAME/KEY: misc_RNA
          (B) LOCATION: 8538..8878

    (ix) FEATURE:
          (A) NAME/KEY: CDS
          (B) LOCATION: join(470..583, 3258..3449, 3939..4122,
               5831..5944, 6633..6758, 6967..7252, 7871..8102)

    (xi) SEQUENCE DESCRIPTION: SEQ ID NO: 3:

GAATTCATGC CCCTTTTGAA ATAGACTTAT GTCATTGTCA GAAAACATAA GCATTTATGG     60

TATATCATTA ATGAGTCACG ATTTTAGTGG TTGCCTTGTG AGTAGGTCAA ATTTACTAAG    120

CTTAGATTTG TTTTCTCACA TATTCTTTCG GAGCTTGTGT AGTTTCCACA TTAATTTACC    180

AGAAACAAGA TACACACTCT CTTTGAGGAG TGCCCTAACT TCCCATCATT TTGTCCAATT    240

AAATGAATTG AAGAAATTTA ATGTTTCTAA ACTAGACCAA CAAAGAATAA TAGTTGTATG    300

ACAAGTAAAT AAGCTTTGCT GGGAAGATGT TGCTTAAATG ATAAAATGGT TCAGCCAACA    360

AGTGAACCAA AAATTAAATA TTAACTAAGG AAAGGTAACC ATTTCTGAAG TCATTCCTAG    420

CAGAGGACTC AGATATATAT AGGATTGAAG ATCTCTCAGT TAAGTCTAC ATG AAA        475
                                                      Met Lys
                                                        1

AGG ATG GTT TCT TGG AGC TTC CAC AAA CTT AAA ACC ATG AAA CAT CTA      523
Arg Met Val Ser Trp Ser Phe His Lys Leu Lys Thr Met Lys His Leu
          5                  10                  15

TTA TTG CTA CTA TTG TGT GTT TTT CTA GTT AAG TCC CAA GGT GTC AAC      571
Leu Leu Leu Leu Leu Cys Val Phe Leu Val Lys Ser Gln Gly Val Asn
     20                  25                  30

GAC AAT GAG GAG GTGAATTTTT TAAAGCATTA TTATATTATT AGTAGTATTA          623
Asp Asn Glu Glu
 35

TTAATATAAG ATGTAACATA ATCATATTAT GTGCTTATTT TAATGAAATT AGCATTGCTT    683

ATAGTTATGA AATGGAATTG TTAACCTCTG ACTTATTGTA TTTAAAGAAT GTTTCATAGT    743

ATTTCTTATA TAAAAACAAA GTAATTTCTT GTTTTCTAGT TTATCACCTT TGTTTTCTTA    803

AGATGAGGAT GGCTTAGCTA ATGTAAGATG TGTTTTTCTC ACTTGCTATT CTGAGTACTG    863

TGATTTTCAT TTACTTCTAG CAATACAGGA TTACAATTAA GAGGACAAGA TCTGAAAATC    923

TCACAAACTA TAAAATAATA AAAGAGCAGA ATTTTAAGAT AAAAGAAACT GGTGGTAGGT    983

AGATTGTTCT TTGGTGAAGG AAGGTAATAT ATATTGTTAC TGAGATTACT ATTTATAAAA   1043

ATTATAACTA AGCCTAAAAG CAAAATACAT CAAGTGTAAT GATAGAAAAT GAAATATTGC   1103

TTTTTTCAGA TGAAAAGTTC AAATTAGAGT TAGTGTGTAT TGTTATTATT AATAGTTATG   1163

AAACACGGTT CAGTCTAATT TATTTATTTG TAGAACAGTT TGTCCTCAAC TATTATTTTT   1223

GCTGACTTAT TGCTGTTAAT TTGCAGTTAC TAAAAATACA GAAATGCATT TAGGACAATG   1283

GATATTTAAG AAATTTAAAT TTTATCATCA AACGTATCAT GGCCAAATTT CTTACATATA   1343

GCATAGTATC ATTAAACTAG AAATAAGAAT ACACAATAAT ATTTAAATGA AGTGATTCAT   1403

TTCGGATCAT TATTGAGTTT CAAGGGAACT TGAGTGTTGT ACTTATCAGA CTCTACATGT   1463
```

```
AAGAACATAT AGTTAATCTG GTTGTGTGTG TAAAAACATA TGGTTAATCT GGTTAAGTCT   1523

GGTTAATCAT ATTAGGTAAG AAAAATGTAA AGAATGTGTA AGACGAAATT TTTGTAAAGT   1583

ACTCTGCAAA GCACTTTCAC ATTTCTGCTT ATCAACTAAA CCTCACAGAG ATAGTTTAAT   1643

AGTTTAGGCT TTAAAATGGA TTTTGATTAT TCAACAAGTG GCCTTCATAA TTTCTTTAAG   1703

TGTTTTTCTT TAAGTATATA CTTTCTTTAA ATATTTTTTA AAATTTCCTT TTCTCTAGTA   1763

AAGCCAGACC ATCCATGCTA CCTCTCTAGT GGCACTCTGA AATAAAAAGA AAATAGTTTT   1823

CTCTGTTATA ATTGTATTTG TAATAAGCAG ATGAATCACA TTTCTTAAAA TTTGTTTTAG   1883

AGAGGGTAAG CTCTGACTAG GACCATGACT TCAATGTGAA ATATGTATAT ATCCTCCGAA   1943

TCTTTACATA TTAAGAATGT ATATAGTCAA CTGGTTAAAC AGGAAAATCT GGAACAGCCT   2003

GGCTGGGTTT TAATCTTAGC ACCATCCTAC TAAATGTTAA ATAATATTAT AATCTAATGA   2063

ATAAATGACA ATGCAATTCC AAATAGAGTT CATCTGATGA CTTCTAGACT CACAAAATTG   2123

CAAGAGAGCT CAGTTGTTGC TCAGTTGTTC CAAATCATGT CGTTTGTTAA TTTGTAATTA   2183

AGCTCCAAAG GATGTATAGC TACTGACAAA AAAAAAAATG AGAATGTAGT TAATCCAAAT   2243

CAAAACTTTC CTATTGCAAT GCGTATTTTC TGCTTCATTA TCCTTTAATA TAATATTTTA   2303

AGTTAGCAAG TAATTTTAAT TACAATGCAC AAGCCTTGAG AATTATTTTA AATATAAGAA   2363

AATCATAATG TTTGATAAAG AAATCATGTA AGAAATTTCA AGATAATGGT TTAACAAATA   2423

ATTTTGTTGA TAGAAGATAA GACTAAAAGT GAAATTCGAA GTGGAGAGGA CACTTAAACT   2483

GTAGTACTTG TTATGTGTGA TTCCAGTAAA AATAGTAATG AGCACTTATT ATTGCCAAGT   2543

ACTGTTCTGA GGGTACCATA TGCAATAAGT TATTTAATCC TTACAATAAT CTTGTAAGGC   2603

AGATTCAAAC TATCATTACA CTTATTTTAC AGATGAGAAA ACTGGGGCAC AGATAAAGCA   2663

ACTTGCCCAA GGTCTCATAG CTGTAAGTCA ACCCTACGGT CAAGACCTAC AAGTAGCCGA   2723

GCTCCAGAGT ACATTATGAG GGTCAAAGAT TGTCTTATTA CAAATAAATT CCAAGTAGAA   2783

TCAACCTTTA ATAAGTCTTT AATGTCTCTT AAATATGTTT ATATAGGAGT CTAATCACCA   2843

ATTCACAAAA ATGAAAGTAG GGAAATGATT AACAATAATC ATAGGAATCT AACAATCCAA   2903

GTGGCTTGAG AATATTCATT CTTCTTGACA GTATAGATTC TTTACAATTT CGTAAGTTCC   2963

AATGTATGTT TTAGGAATAT GAGGTCATTA CTATTCATAA TCTGATACAG CTTTATCCTA   3023

AGGCCTCTCT TTAAAAACTA CACTGCATCA TAGCTTTTTT GTGCAGTTGG TCTTTCTACT   3083

GTTACTGAAC AGTAAGCAAC CTACAGATTC ACTATCACCA ACCAGCCAGT TGATGGATCT   3143

TAAGCAAATT ATCAAGCTTG TGATAACCTA AATTATAAAA TGAGGGTGTT GGAATAGTTA   3203

CATTCCAAAT CTTCTATAAC ACTCTGTATT ATATTTCTGC CTCATTCCTT GTAG GGT     3260
                                                            Gly

TTC TTC AGT GCC CGT GGT CAT CGA CCC CTT GAC AAG AAG AGA GAA GAG     3308
Phe Phe Ser Ala Arg Gly His Arg Pro Leu Asp Lys Lys Arg Glu Glu
 40                  45                  50                  55

GCT CCC AGC CTG AGG CCT GCC CCA CCG CCC ATC AGT GGA GGT GGC TAT     3356
Ala Pro Ser Leu Arg Pro Ala Pro Pro Pro Ile Ser Gly Gly Gly Tyr
                 60                  65                  70

CGG GCT CGT CCA GCC AAA GCA GCT GCC ACT CAA AAG AAA GTA GAA AGA     3404
Arg Ala Arg Pro Ala Lys Ala Ala Ala Thr Gln Lys Lys Val Glu Arg
             75                  80                  85

AAA GCC CCT GAT GCT GGA GGC TGT CTT CAC GCT GAC CCA GAC CTG         3449
Lys Ala Pro Asp Ala Gly Gly Cys Leu His Ala Asp Pro Asp Leu
         90                  95                 100

GTGGGTGCAC TGATGTTTCT TGCAGTGGTG GCTCTCTCAT GCAGAGAAAG CCTGTAGTCA   3509

TGGCAGTCTG CTAATGTTTC ACTGACCCAC ATTACCATCA CTGTTATTTT GTTTGTTTAT   3569
```

```
TTTGGAAATA AAATTCAAAA CATAAACATA TTGGGCCTTT GGTTTAGGCT TTCTTTCTTG   3629

TTTTCTTTGG TCTGGGCCCA AAATTTCAAA TTAGGATATG TGGGTGCCAC CTTTCCATTT   3689

GTATTTTGCC ACTGCCTTTG TTTAGTTGGT AAAATTTTCA TAGCCCAATT ATATTTTTTC   3749

TGGGGTAAGT AATATTTTAA ATCTCTATGA GAGTATGATG ATGACTTTCG AATTTCTGGT   3809

CTTACAGAAA ACCAAATAAT AAATTTTTAT GTTGGCTAAT CGTATCGCTG AATTTTCCTA   3869

TGTGCTATTT TAACAAATGT CCATGACCCA AATCCTTCAT CTAATGCCTG CTATTTTCTT   3929

TGTTTTTAG GGG GTG TTG TGT CCT ACA GGA TGT CAG TTG CAA GAG GCT       3977
          Gly Val Leu Cys Pro Thr Gly Cys Gln Leu Gln Glu Ala
                  105                 110                 115

TTG CTA CAA CAG GAA AGG CCA ATC AGA AAT AGT GTT GAT GAG TTA AAT     4025
Leu Leu Gln Gln Glu Arg Pro Ile Arg Asn Ser Val Asp Glu Leu Asn
                120                 125                 130

AAC AAT GTG GAA GCT GTT TCC CAG ACC TCC TCT TCT TCC TTT CAG TAC     4073
Asn Asn Val Glu Ala Val Ser Gln Thr Ser Ser Ser Ser Phe Gln Tyr
            135                 140                 145

ATG TAT TTG CTG AAA GAC CTG TGG CAA AAG AGG CAG AAG CAA GTA AAA  G  4122
Met Tyr Leu Leu Lys Asp Leu Trp Gln Lys Arg Gln Lys Gln Val Lys
        150                 155                 160

GTAGATATCC TTGTGCTTTC CATTCGATTT TCAGCTATAA AATTGGAACC GTTAGACTGC   4182

CACGAGAATG CATGGTTGTG AGAAGATTAA CATTTCTGGG TTAGTGAATA GCATTCATAC   4242

GCTTTTGGGC ACCTTCCCCT GCAACTTGCC AGATAAGCAC TATTCAGCTC TTATTCCCAG   4302

TCTGACATCA GCAAGTGTGA TTTTCTATGA AAAATTCTAC TATGACTCCT TATTTTAAGT   4362

ATACAAGAAA CTTGTGACTC AGAAGATAAT ATTTACAGAG TGGAAAAAAA CCCCTAGCAT   4422

TTATAGTTTT AACATTTGAG GTTTTGAATG AGAGAGTTAT CCATAATATA TTCAATTGTG   4482

TTGTGGATAA TGACACCTAA CCTGTGAATC TTGAGGTCAG AATGTTGAGT GCTGTTGACT   4542

TGGTGGTCAG GAAACAGCTA GTGCGTGAGC CTGGCACAGG CATCTCAGTG AGTAGCATAC   4602

CCACAGTTGG AAATTTTTCA AAGAAATCAA AGGAATCATG ACATCTTATA AATTTCAAGG   4662

TTCTGCTATA CTTATGTGAA ATGGATAAAT AAATCAAGCA TATCCACTCT GTAAGATTGA   4722

ACTTCTCAGA TGGAAGACCC CAATACTGCT TTCTCCTCTT TTCCCTCACC AAAGAAATAA   4782

ACAACCTATT TCATTTATTA CTGGACACAA TCTTTAGCGT ATACCTATGG TAAATTACTA   4842

GTATGGTGGT TAGGATTTAT GTTAATTTGT ATATGTCATG CGCCAAATCA TTTCCACTAA   4902

ATATGACTAT ATATCATAAC TGCTTGGTGA TAGCTCAGTG TTTAATAGTT TATTCTCAGA   4962

AAATCAAAAT TGTATAGTTA AATACATTAG TTTTATGAGG CAAAAATGCT AACTATTTCT   5022

ACATAATTTC ATTTTTCCAG  AT AAT GAA AAT GTA GTC AAT GAG TAC TCC       5071
                      Asp Asn Glu Asn Val Val Asn Glu Tyr Ser
                          165                 170

TCA GAA CTG GAA AAG CAC CAA TTA TAT ATA GAT GAG ACT GTG AAT AGC     5119
Ser Glu Leu Glu Lys His Gln Leu Tyr Ile Asp Glu Thr Val Asn Ser
    175                 180                 185

AAT ATC CCA ACT AAC CTT CGT GTG CTT CGT TCA ATC CTG GAA AAC CTG     5167
Asn Ile Pro Thr Asn Leu Arg Val Leu Arg Ser Ile Leu Glu Asn Leu
190                 195                 200                 205

AGA AGC AAA ATA CAA AAG TTA GAA TCT GAT GTC TCA GCT CAA ATG GAA     5215
Arg Ser Lys Ile Gln Lys Leu Glu Ser Asp Val Ser Ala Gln Met Glu
                210                 215                 220

TAT TGT CGC ACC CCA TGC ACT GTC AGT TGC AAT ATT CCT GTG GTG TCT     5263
Tyr Cys Arg Thr Pro Cys Thr Val Ser Cys Asn Ile Pro Val Val Ser
            225                 230                 235
```

```
GGC AAA  G GTAACTGATT CATAAACATA TTTTTAGAGA GTTCCAGAAG AACTCACACA   5320
Gly Lys

CCAAAAATAA GAGAACAACA ACAACAACAA AAATGCTAAG TGGATTTTCC CAACAGATCA   5380

TAATGACATT ACAGTACATC ATAAAAATAT CCTTAGCCAG TTGTGTTTTG GACTGGCCTG   5440

GTGCATTTGC TGGTTTTGAT GAGCAGGATG GGGCACAGGT AGTCCCAGGG GTGGCTGATG   5500

TGTGCATCTG CGTACTGGCT TGAACAGATG GCAGAACCAC AGATAGATGT AGAAGTTTCT   5560

CCATTTTGTG TGTTCTGGGA GCTCATGGAT ATTCCAGGAC ACAAAAGGTG GAGAAGAGCT   5620

TTGTTCATCC TCTTAGCAGA TAAACGTCCT CAAAACTGGG TTGGACTTAC TAAAGTAAAA   5680

TGAAAATCTA ATATTTGTTA TATTATTTTC AAAGGTCTAT AATAACACAC TCCTTAGTAA   5740

CTTATGTAAT GTTATTTTAA AGAATTGGTG ACTAAATACA AAGTAATTAT GTCATAAACC   5800

CCTGAACATA ATGTTGTCTT ACATTTGCAG  AA TGT GAG GAA ATT ATC AGG AAA    5853
                                 Glu Cys Glu Glu Ile Ile Arg Lys
                                 240                 245

GGA GGT GAA ACA TCT GAA ATG TAT CTC ATT CAA CCT GAC AGT TCT GTC     5901
Gly Gly Glu Thr Ser Glu Met Tyr Leu Ile Gln Pro Asp Ser Ser Val
        250                 255                 260

AAA CCG TAT AGA GTA TAC TGT GAC ATG AAT ACA GAA AAT GGA  G          5944
Lys Pro Tyr Arg Val Tyr Cys Asp Met Asn Thr Glu Asn Gly
    265                 270                 275

GTAAGCTTTC GACAGTTGTT GACCTGTTGA TCTGTAATTA TTTGGATACC GTAAAATGCC   6004

AGGAAACAAG GCCAGGTGTG GTGGCTCATA CCTGTAATTC CAGCACCTTG GGAGGCCAAA   6064

GTGGGCTGAT AGCTTGAGCC TAGGAGTTTG AAACTAGCCT GGGCAACATA ATGAGACCCT   6124

AACTCTACAA AAAAAAAAAA AATACCAAAA AAAAAAAAAA AATCAGCTGT GTTGGTAGTA   6184

TGTGCCTGTA GTCCCAGCTA TCCAGGAGGC TGAGATGGGA GATCACCTGA GCCCACAACC   6244

TGGAGTCTTG ATCATGCTAC TGAACTGTAG CCTGGGCAAC AGAGGATAGT GAGATCCTGT   6304

CTCAAAAAAA AAAATTAATT AAAAAGCCAG GAAACAAGAC TTAGCTCTAA CATCTAACAT   6364

AGCTGACAAA GGAGTAATTT GATGTGGAAT TCAACCTGAT ATTTAAAAGT TATAAAATAT   6424

CTATAATTCA CAATTTGGGG TAAGATAAAG CACTTGCAGT TTCCAAAGAT TTTACAAGTT   6484

TACCTCTCAT ATTTATTTCC TTATTGTGTC TATTTTAGAG CACCAAATAT ATACTAAATG   6544

GAATGGACAG GGGATTCAGA TATTATTTTC AAAGTGACAT TATTTGCTGT TGGTTAATAT   6604

ATGCTCTTTT TGTTTCTGTC AACCAAAG  GA TGG ACA GTG ATT CAG AAC CGT      6655
                               Gly Trp Thr Val Ile Gln Asn Arg
                                       280                 285

CAA GAC GGT AGT GTT GAC TTT GGC AGG AAA TGG GAT CCA TAT AAA CAG     6703
Gln Asp Gly Ser Val Asp Phe Gly Arg Lys Trp Asp Pro Tyr Lys Gln
                290                 295                 300

GGA TTT GGA AAT GTT GCA ACC AAC ACA GAT GGG AAG AAT TAC TGT GGC     6751
Gly Phe Gly Asn Val Ala Thr Asn Thr Asp Gly Lys Asn Tyr Cys Gly
            305                 310                 315

CTA CCA  G GTAACGAACA GGCATGCAAA ATAAAATCAT TCTATTTGAA ATGGGATTTT   6808
Leu Pro

TTTTAATTAA AAAACATTCA TTGTTGGAAG CCTGTTTTAG GCAGTTAAGA GGAGTTTCCT   6868

GACAAAAATG TGGAAGCTAA AGATAAGGGA AGAAAGGCAG TTTTTAGTTT CCCAAAATTT   6928

TATTTTTGGT GAGAGATTTT ATTTTGTTTT TCTTTTAG  GT GAA TAT TGG CTT       6980
                                          Gly Glu Tyr Trp Leu
                                          320

GGA AAT GAT AAA ATT AGC CAG CTT ACC AGG ATG GGA CCC ACA GAA CTT     7028
Gly Asn Asp Lys Ile Ser Gln Leu Thr Arg Met Gly Pro Thr Glu Leu
325                 330                 335                 340
```

-continued

```
TTG ATA GAA ATG GAG GAC TGG AAA GGA GAC AAA GTA AAG GCT CAC TAT     7076
Leu Ile Glu Met Glu Asp Trp Lys Gly Asp Lys Val Lys Ala His Tyr
                345                 350                 355

GGA GGA TTC ACT GTA CAG AAT GAA GCC AAC AAA TAC CAG ATC TCA GTG     7124
Gly Gly Phe Thr Val Gln Asn Glu Ala Asn Lys Tyr Gln Ile Ser Val
            360                 365                 370

AAC AAA TAC AGA GGA ACA GCC GGT AAT GCC CTC ATG GAT GGA GCA TCT     7172
Asn Lys Tyr Arg Gly Thr Ala Gly Asn Ala Leu Met Asp Gly Ala Ser
        375                 380                 385

CAG CTG ATG GGA GAA AAC AGG ACC ATG ACC ATT CAC AAC GGC ATG TTC     7220
Gln Leu Met Gly Glu Asn Arg Thr Met Thr Ile His Asn Gly Met Phe
    390                 395                 400

TTC AGC ACG TAT GAC AGA GAC AAT GAC GGC  TG  GTATGTGTGG             7262
Phe Ser Thr Tyr Asp Arg Asp Asn Asp Gly  Trp
405                 410                 415

CACTCTTTGC TCCTGCTTTA AAAATCACAC TAATATCATT ACTCAGAATC ATTAACAATA   7322

TTTTTAATAG CTACCACTTC CTGGGCACTT ACTGTCAGCC ACTGTCCTAA GCTCTTTATG   7382

CATCACTCGA AAGCATTTCA ACTATAAGGT AGACATTCTT ATTCTCATTT TACAGATGAG   7442

ATTTAGAGAG ATTACGTGAT TTGTCCAATG TCACACAACT ACCCAGAGAT AAAACTAGAA   7502

TTTGAGCACA GTTACTTTCT GAATAATGAG CATTTAGATA AATACCTATA TCTCTATATT   7562

CTAAAGTGTG TGTGAAAACT TTCATTTTCA TTTCCAGGGT TCTCTGATAC TAAGGGTTGT   7622

AAAAGCTATT ATTCCAGTAT AAAGTAACAA ACACAGTCCC TAGATGGATT GCCACAAAGG   7682

CCCAGTTATC TCTCTTTCTT GCTATAGGGC ACAGGAGGTC TTTGGTGTAT TAGTGTGACT   7742

CTATGTATAG CACCCAAAGG AAAGACTACT GTGCACACGA GTGTAGCAGT CTTTTATGGG   7802

TAATCTGCAA AACGTAACTT GACCACCGTA GTTCTGTTTC TAATAACGCC AAACACATTT   7862

TCTTTCAG G TTA ACA TCA GAT CCC AGA AAA CAG TGT TCT AAA GAA GAC      7910
           Leu Thr Ser Asp Pro Arg Lys Gln Cys Ser Lys Glu Asp
                           420                 425

GGT GGT GGA TGG TGG TAT AAT AGA TGT CAT GCA GCC AAT CCA AAC GGC     7958
Gly Gly Gly Trp Trp Tyr Asn Arg Cys His Ala Ala Asn Pro Asn Gly
    430                 435                 440

AGA TAC TAC TGG GGT GGA CAG TAC ACC TGG GAC ATG GCA AAG CAT GGC     8006
Arg Tyr Tyr Trp Gly Gly Gln Tyr Thr Trp Asp Met Ala Lys His Gly
445                 450                 455                 460

ACA GAT GAT GGT GTA GTA TGG ATG AAT TGG AAG GGG TCA TGG TAC TCA     8054
Thr Asp Asp Gly Val Val Trp Met Asn Trp Lys Gly Ser Trp Tyr Ser
                465                 470                 475

ATG AGG AAG ATG AGT ATG AAG ATC AGG CCC TTC TTC CCA CAG CAA         8099
Met Arg Lys Met Ser Met Lys Ile Arg Pro Phe Phe Pro Gln Gln
            480                 485                 490

TAGTCCCCAA TACGTAGATT TTTGCTCTTC TGTATGTGAC AACATTTTTG TACATTATGT   8159

TATTGGAATT TTCTTTCATA CATTATATTC CTCTAAAACT CTCAAGCAGA CGTGAGTGTG   8219

ACTTTTTGAA AAAAGTATAG GATAAATTAC ATTAAAATAG CACATGATTT TCTTTTGTTT   8279

TCTTCATTTC TCTTGCTCAC CCAAGAAGTA ACAAAAGTAT AGTTTTGACA GAGTTGGTGT   8339

TCATAATTTC AGTTCTAGTT GATTGCGAGA ATTTTCAAAT AAGGAAGAGG GGTCTTTTAT   8399

CCTTGTCGTA GGAAAACCAT GACGGAAAGG AAAAACTGAT GTTTAAAAGT CCACTTTTAA   8459

AACTATATTT ATTTATGTAG GATCTGTCAA AGAAAACTTC CAAAAAGATT TATTAATTAA   8519

ACCAGACTCT GTTGCAATAA GTTAATGTTT TCTTGTTTTG TAATCCACAC ATTCAATGAG   8579

TTAGGCTTTG CACTTGTAAG GAAGGAGAAG CGTTCACAAC CTCAAATAGC TAATAAACCG   8639

GTCTTGAATA TTTGAAGATT TAAAATCTGA CTCTAGGACG GGCACGGTGG CTCACGACTA   8699
```

```
TAATCCCAAC ACTTTGGGAG GCTGAGGCGG GCGGTCACAA GGTCAGGAGT TCAAGACCAG   8759

CCTGACCAAT ATGGTGAAAC CCCATCTCTA CTAAAAATAC AAAAATTAGC CAGGCGTGGT   8819

GGCAGGTGCC TGTAGGTCCC AGCTAGCCTG TGAGGTGGAG ATTGCATTGA GCCAAGATC    8878
```

(2) INFORMATION FOR SEQ ID NO: 4:

(i) SEQUENCE CHARACTERISTICS:
(A) LENGTH: 491 amino acids
(B) TYPE: amino acid
(D) TOPOLOGY: linear (ii) MOLECULE TYPE: protein (xi) SEQUENCE DESCRIPTION: SEQ ID NO: 4:

```
Met Lys Arg Met Val Ser Trp Ser Phe His Lys Leu Lys Thr Met Lys
  1               5                  10                  15

His Leu Leu Leu Leu Leu Leu Cys Val Phe Leu Val Lys Ser Gln Gly
             20                  25                  30

Val Asn Asp Asn Glu Glu Gly Phe Phe Ser Ala Arg Gly His Arg Pro
         35                  40                  45

Leu Asp Lys Lys Arg Glu Glu Ala Pro Ser Leu Arg Pro Ala Pro Pro
     50                  55                  60

Pro Ile Ser Gly Gly Gly Tyr Arg Ala Arg Pro Ala Lys Ala Ala Ala
 65                  70                  75                  80

Thr Gln Lys Lys Val Glu Arg Lys Ala Pro Asp Ala Gly Gly Cys Leu
                 85                  90                  95

His Ala Asp Pro Asp Leu Gly Val Leu Cys Pro Thr Gly Cys Gln Leu
            100                 105                 110

Gln Glu Ala Leu Leu Gln Gln Glu Arg Pro Ile Arg Asn Ser Val Asp
        115                 120                 125

Glu Leu Asn Asn Asn Val Glu Ala Val Ser Gln Thr Ser Ser Ser Ser
    130                 135                 140

Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
                165                 170                 175

Glu Lys His Gln Leu Tyr Ile Asp Glu Thr Val Asn Ser Asn Ile Pro
            180                 185                 190

Thr Asn Leu Arg Val Leu Arg Ser Ile Leu Glu Asn Leu Arg Ser Lys
        195                 200                 205

Ile Gln Lys Leu Glu Ser Asp Val Ser Ala Gln Met Glu Tyr Cys Arg
    210                 215                 220

Thr Pro Cys Thr Val Ser Cys Asn Ile Pro Val Val Ser Gly Lys Glu
225                 230                 235                 240

Cys Glu Glu Ile Ile Arg Lys Gly Gly Glu Thr Ser Glu Met Tyr Leu
                245                 250                 255

Ile Gln Pro Asp Ser Ser Val Lys Pro Tyr Arg Val Tyr Cys Asp Met
            260                 265                 270

Asn Thr Glu Asn Gly Gly Trp Thr Val Ile Gln Asn Arg Gln Asp Gly
        275                 280                 285

Ser Val Asp Phe Gly Arg Lys Trp Asp Pro Tyr Lys Gln Gly Phe Gly
    290                 295                 300

Asn Val Ala Thr Asn Thr Asp Gly Lys Asn Tyr Cys Gly Leu Pro Gly
305                 310                 315                 320

Glu Tyr Trp Leu Gly Asn Asp Lys Ile Ser Gln Leu Thr Arg Met Gly
                325                 330                 335
```

```
Pro Thr Glu Leu Leu Ile Glu Met Glu Asp Trp Lys Gly Asp Lys Val
            340                 345                 350

Lys Ala His Tyr Gly Gly Phe Thr Val Gln Asn Glu Ala Asn Lys Tyr
        355                 360                 365

Gln Ile Ser Val Asn Lys Tyr Arg Gly Thr Ala Gly Asn Ala Leu Met
    370                 375                 380

Asp Gly Ala Ser Gln Leu Met Gly Glu Asn Arg Thr Met Thr Ile His
385                 390                 395                 400

Asn Gly Met Phe Phe Ser Thr Tyr Asp Arg Asp Asn Asp Gly Trp Leu
                405                 410                 415

Thr Ser Asp Pro Arg Lys Gln Cys Ser Lys Glu Asp Gly Gly Gly Trp
            420                 425                 430

Trp Tyr Asn Arg Cys His Ala Ala Asn Pro Asn Gly Arg Tyr Tyr Trp
        435                 440                 445

Gly Gly Gln Tyr Thr Trp Asp Met Ala Lys His Gly Thr Asp Asp Gly
    450                 455                 460

Val Val Trp Met Asn Trp Lys Gly Ser Trp Tyr Ser Met Arg Lys Met
465                 470                 475                 480

Ser Met Lys Ile Arg Pro Phe Phe Pro Gln Gln
                485                 490


(2) INFORMATION FOR SEQ ID NO: 5:

     (i) SEQUENCE CHARACTERISTICS:
          (A) LENGTH: 10564 base pairs
          (B) TYPE: nucleic acid
          (C) STRANDEDNESS: double
          (D) TOPOLOGY: linear

    (ii) MOLECULE TYPE: DNA (genomic)

   (vii) IMMEDIATE SOURCE:
          (B) CLONE: human fibrinogen gamma chain

    (ix) FEATURE:
          (A) NAME/KEY: CDS
          (B) LOCATION: join(1799..1876, 1973..2017, 2207..2390, 2510
               ..2603, 4211..4341, 4645..4778, 5758..5942, 7426
               ..7703, 9342..9571)

    (xi) SEQUENCE DESCRIPTION: SEQ ID NO: 5:

CTACACACTT CTTGAAGGCA AAGGCAATGC TGAAGTCACC TTTCATGTTC AAATCATATT     60

AAAAAGTTAG CAAGATGTAA TTATCAGTGT ACTATGTAAA TCTTTGTGAA TGATCAATAA    120

TTACATATTT TCATTATATA TATTTTAGTA GATAATATTT ATATACATTC AACATTCTAA    180

ATATAGAAAG TTTACAGAGA AAAATAAAGC CTTTTTTTCC AATCCTGTCC TCCACCTCTG    240

CATCCCATTC TTCTTCACAG AGGCAACTGA TTCAAGTCAT TACATAGTTA TTGAGTGTTA    300

ACTACAACTA TGTTAAGTAC AGCTATATAT GTTAGATGCC GTAGCCACAG AAATCAGTTT    360

ACAATCTAAT GCAGTGGATA CAGCATGTAT ACATATAATA TAAGGTTGCT ACAAATGCTA    420

TCTGAGGTAG AGCTGTTTGA AAGAATACTA ATACTTAAAT GTTTAATTCA ACTGACTTGA    480

TTGACAACTG ATTAGCTGAG TGGAAAAGAT GGATGAGAAA GATTGTGAGA CTTAATTGGC    540

TGGTGGTATG GTGATATGAT TGACAATAAC TGCTAAGTCA GAGAGGGATA TATTAAGGAG    600

GAGAAGAAAA GCAACAAATC TGGTTTTGAT GTGTTCACTT TGTTATAATT ATTGATTATT    660

TACTGAATAT GAATATTTAT CTTTGTTTTT GAGTCAATAA ATATACCTTT GTAAAGACAG    720

AATTAAAGTA TTAGTATTTC TTTCAAACTG GAGGCATTTC TCCCACTAAC ATATTTCATC    780

AAAACTTATA ATAAGCTTGG TTCCAGAGGA AGAAATGAGG GATAACCAAA AATAGAGACA    840
```

-continued

```
TTAATAATAG TGTAACGCCC AGTGATAAAT CTCAATAGGC AGTGATGACA GACATGTTTT    900

CCCAAACACA AGGATGCTGT AAGGGCCAAA CAGAAATGAT GGCCCCTCCC CAGCACCTCA    960

TTTTGCCCCT TCCTTCAGCT ATGCCTCTAC TCTCCTTTAG ATACAAGGGA GGTGGATTTT   1020

TCTCTTCTCT GAGATAGCTT GATGGAACCA CAGGAACAAT GAAGTGGGCT CCTGGCTCTT   1080

TTCTCTGTGG CAGATGGGGT GCCATGCCCA CCTTCAGACA AAGGGAAGAT TGAGCTCAAA   1140

AGCTCCCTGA GAAGTGAGAG CCTATGAACA TGGTTGACAC AGAGGGACAG GAATGTATTT   1200

CCAGGGTCAT TCATTCCTGG GAATAGTGAA CTGGGACATG GGGGAAGTCA GTCTCCTCCT   1260

GCCACAGCCA CAGATTAAAA ATAATAATGT TAACTGATCC CTAGGCTAAA ATAATAGTGT   1320

TAACTGATCC CTAAGCTAAG AAAGTTCTTT TGGTAATTCA GGTGATGGCA GCAGGACCCA   1380

TCTTAAGGAT AGACTAGGTT TGCTTAGTTC GAGGTCATAT CTGTTTGCTC TCAGCCATGT   1440

ACTGGAAGAA GTTGCATCAC ACAGCCTCCA GGACTGCCCT CCTCCTCACA GCAATGGATA   1500

ATGCTTCACT AGCCTTTGCA GATAATTTTG GATCAGAGAA AAAACCTTGA GCTGGGCCAA   1560

AAAGGAGGAG CTTCAACCTG TGTGCAAAAT CTGGGAACCT GACAGTATAG GTTGGGGGCC   1620

AGGATGAGGA AAAAGGAACG GGAAAGACCT GCCCACCCTT CTGGTAAGGA GGCCCCGTGA   1680

TCAGCTCCAG CCATTTGCAG TCCTGGCTAT CCCAGGAGCT TACATAAAGG GACAATTGGA   1740

GCCTGAGAGG TGACAGTGCT GACACTACAA GGCTCGGAGC TCCGGGCACT CAGACATC     1798

ATG AGT TGG TCC TTG CAC CCC CGG AAT TTA ATT CTC TAC TTC TAT GCT     1846
Met Ser Trp Ser Leu His Pro Arg Asn Leu Ile Leu Tyr Phe Tyr Ala
  1               5                  10                  15

CTT TTA TTT CTC TCT TCA ACA TGT GTA GCA GTAAGTGTGC TCTTCACAAA       1896
Leu Leu Phe Leu Ser Ser Thr Cys Val Ala
             20                  25

ACGTTGTTTA AAATGGAAAG CTGGAAAATA AAACAGATAA TAAACTAGTG AAATTTTCGT   1956

ATTTTTTCTC TTTTAG TAT GTT GCT ACC AGA GAC AAC TGC TGC ATC TTA       2005
                  Tyr Val Ala Thr Arg Asp Asn Cys Cys Ile Leu
                              30                  35

GAT GAA AGA TTC GTAAGTAGTT TTTATGTTTC TCCCTTTGTG TGTGAACTGG         2057
Asp Glu Arg Phe
         40

AGAGGGGCAG AGGAATAGAA ATAATTCCCT CATAAATATC ATCTGGCACT TGTAACTTTT   2117

TAAAAACATA GTCTAGGTTT TACCTATTTT TCTTAATAGA TTTTAAGAGT AGCATCTGTC   2177

TACATTTTTA ATCACTGTTA TATTTTCAG GGT AGT TAT TGT CCA ACT ACC TGT     2230
                                Gly Ser Tyr Cys Pro Thr Thr Cys
                                            45

GGC ATT GCA GAT TTC CTG TCT ACT TAT CAA ACC AAA GTA GAC AAG GAT     2278
Gly Ile Ala Asp Phe Leu Ser Thr Tyr Gln Thr Lys Val Asp Lys Asp
 50                  55                  60                  65

CTA CAG TCT TTG GAA GAC ATC TTA CAT CAA GTT GAA AAC AAA ACA TCA     2326
Leu Gln Ser Leu Glu Asp Ile Leu His Gln Val Glu Asn Lys Thr Ser
                 70                  75                  80

GAA GTC AAA CAG CTG ATA AAA GCA ATC CAA CTC ACT TAT AAT CCT GAT     2374
Glu Val Lys Gln Leu Ile Lys Ala Ile Gln Leu Thr Tyr Asn Pro Asp
             85                  90                  95

GAA TCA TCA AAA CCA  A GTGAGAAAAT AAAGACTACT GACCAAAAAA             2420
Glu Ser Ser Lys Pro
        100

TAATAATAAT AATCTGTGAA GTTCTTTTGC TGTTGTTTTA GTTGTTCTAT TTGCTTAAGG   2480

ATTTTTATGT CTCTGATCCT ATATTACAG  AT ATG ATA GAC GCT GCT ACT TTG     2532
                                Asn Met Ile Asp Ala Ala Thr Leu
                                        105                 110
```

```
AAG TCC AGG ATA ATG TTA GAA GAA ATT ATG AAA TAT GAA GCA TCG ATT     2580
Lys Ser Arg Ile Met Leu Glu Glu Ile Met Lys Tyr Glu Ala Ser Ile
                115                 120                 125

TTA ACA CAT GAC TCA AGT ATT  CG  GTAAGGATTT TTGTTTTAAT TTGCTCTGCA   2633
Leu Thr His Asp Ser Ser Ile  Arg
            130

AGACTGATTT AGTTTTTATT TAATATTCTA TACTTGAGTG AAAGTAATTT TTAATGTGTT   2693

TTCCCCATTT ATAATATCCC AGTGACATTA TGCCTGATTA TGTTGAGCAT AGTAGAGATA   2753

GAAGTTTTTA GTGCAATATA AATTATACTG GGTTATAATT GCTTATTAAT AATCACATTG   2813

AAGAAAGATG TTCTAGATGT CTTCAAATGC TAGTTTGACC ATATTTATCA AAAATTTTTT   2873

CCCCATCCCC CATTTATCTT ACAACATAAA ATCAATCTCA TAGGAATTTG GGTGTTGAAA   2933

ATAAAATCCT CTTTATAAAA ATGCTGACAA ATTGGTGGTT AAAAAAATTA GCAAGCAGAG   2993

GCATAGTAAG GATTTTGGCT CCTAAAGTAA ATTATATTGA ATGTGGAGCA GGAAGAAACA   3053

TGTCTTGAGA GACTAAGTGT GGCAAATATT GCAAAGCTCA TATTGATCAT TGCAGAATGA   3113

ACCTGCATAG TCTCTTCCCT TCATTTGGAA GTGAATGTCT CTGTTAAAGC TTCTCAGGGA   3173

CTCATAAACT TTCTGAACAT AAGGTCTCAG ATACAGTTTT AATATTTTTC CCCAATTTTT   3233

TTTTCTGAAT TTTTCTCAAA GCAGCTTGAG AAATTGAGAT AAATAGTAGC TAGGGAGAAG   3293

TGGCCCAGGA AAGATTTCTC CTCTTTTTGC TATCAGAGGG CCCTTGTTAT TATTGTTATT   3353

ATTATTACTT GCATTATTAT TGTCCATCAT TGAAGTTGAA GGAGGTTATT GTACAGAAAT   3413

TGCCTAAGAC AAGGTAGAGG GAAAACGTGG ACAAATAGTT TGTCTACCCT TTTTTACTTC   3473

AAAGAAAGAA CGGTTTATGC ATTGTAGACA GTTTTCTATC ATTTTTGGAT ATTTGCAAGC   3533

CACCCTGTAA GTAACTACAA AAGGAGGGTT TTTACTTCCC CCAGTCCATT CCCAAAGCTA   3593

TGTAACCAGA AGCATTAAAG AAGAAAGGGG AAGTATCTGT TGTTTTATTT TACATACAAT   3653

AACGTTCCAG ATCATGTCCC TGTGTAAGTT ATATTTTAGA TTGAAGCTTA TATGTATAGC   3713

CTCAGTAGAT CCACAAGTGA AAGGTATACT CCTTCAGCAC ATGTGAATTA CTGAACTGAG   3773

CTTTTCCTGC TTCTAAAGCA TCAGGGGGTG TTCCTATTAA CCAGTCTCGC CACTCTTGCA   3833

GGTTGCTATC TGCTGTCCCT TATGCATAAA GTAAAAAGCA AAATGTCAAT GACATTTGCT   3893

TATTGACAAG GACTTTGTTA TTTGTGTTGG GAGTTGAGAC AATATGCCCC ATTCTAAGTA   3953

AAAAGATTCA GGTCCACATT GTATTCCTGT TTTAATTGAT TTTTTGATTT GTTTTTCTTT   4013

TTCAAAAAGT TTATAATTTT AATTCATGTT AATTTAGTAA TATAATTTTA CATTTTCCTC   4073

AAGAATGGAA TAATTTATCA GAAAGCACTT CTTAAGAAAA TACTTAGCAG TTTCCAAAGA   4133

AAATATAAAA TTACTCTTCT GAAAGGAATA CTTATTTTTG TCTTCTTATT TTTGTTATCT   4193

TATGTTTCTG TTTGTAG A TAT TTG CAG GAA ATA TAT AAT TCA AAT AAT CAA    4244
                     Tyr Leu Gln Glu Ile Tyr Asn Ser Asn Asn Gln
                     135                 140                 145

AAG ATT GTT AAC CTG AAA GAG AAG GTA GCC CAG CTT GAA GCA CAG TGC     4292
Lys Ile Val Asn Leu Lys Glu Lys Val Ala Gln Leu Glu Ala Gln Cys
                150                 155                 160

CAG GAA CCT TGC AAA GAC ACG GTG CAA ATC CAT GAT ATC ACT GGG AAA  G  4341
Gln Glu Pro Cys Lys Asp Thr Val Gln Ile His Asp Ile Thr Gly Lys
            165                 170                 175

GTAACTGATG AAGGTTATAT TGGGATTAGG TTCATCAAAG TAAGTAATGT AAAGGAGAAA   4401

GTATGTACTG GAAAGTATAG GAATAGTTTA GAAAGTGGCT ACCCATTAAG TCTAAGAATT   4461

TCAGTTGTCT AGACCTTTCT TGAATAGCTA AAAAAAACAG TTTAAAAGGA ATGCTGATGT   4521
```

```
GAAAAGTAAG AAAATTATTC TTGGAAAATG AATAGTTTAC TACATGTTAA AAGCTATTTT   4581

TCAAGGCTGG CACAGTCTTA CCTGCATTTC AAACCACAGT AAAAGTCGAT TCTCCTTCTC   4641

TAG  AT TGT CAA GAC ATT GCC AAT AAG GGA GCT AAA CAG AGC GGG CTT     4688
    Asp Cys Gln Asp Ile Ala Asn Lys Gly Ala Lys Gln Ser Gly Leu
            180                 185                 190

TAC TTT ATT AAA CCT CTG AAA GCT AAC CAG CAA TTC TTA GTC TAC TGT     4736
Tyr Phe Ile Lys Pro Leu Lys Ala Asn Gln Gln Phe Leu Val Tyr Cys
        195                 200                 205

GAA ATC GAT GGG TCT GGA AAT GGA TGG ACT GTG TTT CAG AAG             4778
Glu Ile Asp Gly Ser Gly Asn Gly Trp Thr Val Phe Gln Lys
    210                 215                 220

GTAATTTTTT CCCCACCATG TGTATTTAAT AAATTCCTAC ATTGTTTCTG CCATATGGCA   4838

GATACTTTTC TAAGCACCTT GTGAACCGTA GCTCATTTAA TCCTTGCAAT AGCCCTAAGA   4898

GGAAGGTACT TCTGTTACTC CTATTTACAG AAAAGGAAAC TGAGGCACAC AAGGTTAAAT   4958

AACTTGCCCA AGACCACATA ACTAATAAGC AACAGAGTCA GCATTTGAAC CTAGGCAGTA   5018

TAGTTTCAGA GTTTGTGACT TGACTCTATA TTGTACTGGC ACTGACTTTG TAGATTCATG   5078

GTGGCACATA ATCATAGTAC CACAGTGACA AATAAAAAGA AGGAAACTCT TTTGTCAGGT   5138

AGGTCAAGAC CTGAGGTTTC CCATCACAAG ATGAGGAAGC CCAACACCAC CCCCCACCAC   5198

CCCACCACCA TCACCACCCT TTCACACACC AGAGGATACA CTTGGGCTGC TCCAAGACAA   5258

GGAACCTGTG TTGCATCTGC CACTTGCTGA TACCCACTAG GAATCTTGGC TCCTTTACTT   5318

TCTGTTTACC TCCCACCACT GTTATAACTG TTTCTACAGG GGGCGCTCAG AGGGAATGAA   5378

TGGTGGAAGC ATTAGTTGCC AGACACCGAT TGAGCAATGG GTTCCATCAT AAGTGTAAGA   5438

ATCAGTAATA TCCAGCTAGA GTTCTGAAGT CGTCTAGGTG TCTTTTTAAT ATTACCACTC   5498

ATTTAGAATT TATGATGTGC CAGAAACCCT CTTAAGTATT TCTCTTATAT TCTCTCTCAT   5558

GATCCTTGCA GCAACCCTAA GAAGTAACCA TCATTTTTCC TATTTGATAC ATGAGGAAAC   5618

TGAGGTAGCT TGGCCAAGAT CACTTAGTTG GGAGTTGATA GAACCAGTGC TCTGTATTTT   5678

TGACAAAATG TTGACAGCAT TCTCTTTACA TGCATTGATA GTCTATTTTC TCCTTTTGCT   5738

CTTGCAAATG TGTAATTAG AGA CTT GAT GGC AGT GTA GAT TTC AAG AAA AAC    5790
                     Arg Leu Asp Gly Ser Val Asp Phe Lys Lys Asn
                             225                 230

TGG ATT CAA TAT AAA GAA GGA TTT GGA CAT CTG TCT CCT ACT GGC ACA     5838
Trp Ile Gln Tyr Lys Glu Gly Phe Gly His Leu Ser Pro Thr Gly Thr
    235                 240                 245

ACA GAA TTT TGG CTG GGA AAT GAG AAG ATT CAT TTG ATA AGC ACA CAG     5886
Thr Glu Phe Trp Leu Gly Asn Glu Lys Ile His Leu Ile Ser Thr Gln
250                 255                 260                 265

TCT GCC ATC CCA TAT GCA TTA AGA GTG GAA CTG GAA GAC TGG AAT GGC     5934
Ser Ala Ile Pro Tyr Ala Leu Arg Val Glu Leu Glu Asp Trp Asn Gly
                270                 275                 280

AGA ACC  AG  GTACTGTTTT GAAATGACTT CCAACTTTTT ATTGTAAAGA            5982
Arg Thr  Ser

TTGCCTGGAA TGTGCACTTT CCAACTATCA ATAGACAATG GCAAATGCAG CCTGACAAAT   6042

GCAAACAGCA CATCCAGCCA CCATTTTCTC CAGGAGTCTG TTTGGTTCTT GGGCAATCCA   6102

AAAAGGTAAA TTCTATTCAG GATGAATCTA AGTGTATTGG TACAATCTAA TTACCCTGGA   6162

ACCATTCAGA GTAATAGCTA ATTACTGAAC TTTTAATCAG TCCCAGGAAT TGAGCATAAA   6222

ATTATAATTT TATCTAGTCT AAATTACTAT TTCATGAAGC AGGTATTATT ATTAATCCCA   6282

TTTTATAGAT TAACTTGCTC AAAGTCACAT TGCTGATAAG TGGTAGAGGT AGAATTCAGA   6342

CTCAAGTAGT TTAACTTTAG AGCCTGTCCT CTTAACAACT ATCCTGGTTG AAAAGCAAAT   6402
```

-continued

```
ACAGCCTCTT CAGACTTCTC AGTGCCTTGA TGGCCATTTA TTCTGTCAAA TCATGAGCTA   6462

CCCTAAAAGT AAACCAGCTA GCTCTTTTGA TGATCTAGAG GCTTCTTTTT GCTTGAGATA   6522

TTTGAAGGTT TTAAGCATTG TTACCTAATT AAAATGCAGA AAAATATCCA ACCCTCTTGT   6582

TATGTTTAAG GAATAGTGAA ATATATTGTC TTCAAACACA TGGACTTTTT TTTATTGCTT   6642

GGTTGGTTTT TAATCCAGAA AGTGCTATAG TCAGTAGACC TTCTTCTAGG AAAGGACCTT   6702

CCATTTCCCA GCCACTGGAG ATTAGAAAAT AAGCTAAATA TTTTCTGGAA ATTTCTGTTC   6762

ATTCATTAAG GCCCATCCTT TCCCCCACTC TATAGAAGTG TTGTCCACTT GCACAATTTT   6822

TTCCAGGAAA GAATCTCTCT AACTCCTTCA GCTCACATGC TTTGGACCAC ACAGGGAAGA   6882

CTTTGATTGT GTAATGCCCT CAGAAGCTCT CCTTCTTGCC ACTACCACAC TGATTTGAGG   6942

AAGAAAATCC CTTTAGCACC TAACCCTTCA GGTGCTATGA GTGGCTAATG GAACTGTACC   7002

TCCTTCAAGT TTTGTGCAAT AATTAAGGGT CACTCACTGT CAGATACTTT CTGTGATCTA   7062

TGATAATGTG TGTGCAACAC ATAACATTTC AATAAAAGTA GAAAATATGA AATTAGAGTC   7122

ATCTACACAT CTGGATTTGA TCTTAGAATG AAACAAGCAA AAAAGCATCC AAGTGAGTGC   7182

AATTATTAGT TTTCAGAGAT GCTTCAAAGG CTTCTAGGCC CATCCCGGGA AGTGTTAATG   7242

AGCTGTGGAC TGGTTCACAT ATCTATTGCC TCTTGCCAGA TTTGCAAAAA ACTTCACTCA   7302

ATGAGCAAAT TTCAGCCTTA AGAAACAAAG TCAAAAATTC CAAGGAAGCA TCCTACGAAA   7362

GAGGGAACTT CTGAGATCCC TGAGGAGGGT CAGCATGTGA TGGTTGTATT TCCTTCTTCT   7422

CAG T ACT GCA GAC TAT GCC ATG TTC AAG GTG GGA CCT GAA GCT GAC       7468
      Thr Ala Asp Tyr Ala Met Phe Lys Val Gly Pro Glu Ala Asp
      285                 290                 295

AAG TAC CGC CTA ACA TAT GCC TAC TTC GCT GGT GGG GAT GCT GGA GAT     7516
Lys Tyr Arg Leu Thr Tyr Ala Tyr Phe Ala Gly Gly Asp Ala Gly Asp
    300                 305                 310

GCC TTT GAT GGC TTT GAT TTT GGC GAT GAT CCT AGT GAC AAG TTT TTC     7564
Ala Phe Asp Gly Phe Asp Phe Gly Asp Asp Pro Ser Asp Lys Phe Phe
315                 320                 325                 330

ACA TCC CAT AAT GGC ATG CAG TTC AGT ACC TGG GAC AAT GAC AAT GAT     7612
Thr Ser His Asn Gly Met Gln Phe Ser Thr Trp Asp Asn Asp Asn Asp
                335                 340                 345

AAG TTT GAA GGC AAC TGT GCT GAA CAG GAT GGA TCT GGT TGG TGG ATG     7660
Lys Phe Glu Gly Asn Cys Ala Glu Gln Asp Gly Ser Gly Trp Trp Met
            350                 355                 360

AAC AAG TGT CAC GCT GGC CAT CTC AAT GGA GTT TAT TAC CAA  G          7703
Asn Lys Cys His Ala Gly His Leu Asn Gly Val Tyr Tyr Gln
        365                 370                 375

GTATGTTTTC CTTTCTTAGA TTCCAAGTTA ATGTATAGTG TATACTATTT TCATAAAAAA   7763

TAATAAATAG ATATGAAGAA ATGAAGAATA ATTTATAAAG ATAGTAGGGA TTTTATCATG   7823

TTCTTTATTT CAACTAAGTT CTTTGAAACT GGAAGTGGAT AATACCAAGT TCATGCCTAA   7883

AATTAGCCCT TCTAAAGAAA TCCACCTGCT GCAAAATATC CAGTAGTTTG GCATTATATG   7943

TGAAACTATC ACCATCATAG CTGGCACTGT GGGTTGTGGG ATCTCCTTTA GACATACAAC   8003

ATAAATGATC TGGATGGATT AACATTACTA CATGGATGCT TGTTGACACA TTAACCTGGC   8063

TTCCCATGAG CTTTGTGTCA GATACACGCA GTGAACAGGT GTTTGGAGGA ACAGAATAAA   8123

GAGAAGGCAA GCACTGGTAA GGGCAGGGGT TTGTGAAAGC TTGAGAGAAG AGACCAGTCT   8183

GAGGACAGTA GACACTTATT TTAGGATGGG GGTTGGATGA GGAGGCTATA GTTTGCTATA   8243

AGCTTGGAAT GGTTTGGAAC ACTGGTTTCA CTCACCTACC CAGCAGTTAT GTGTGGGGAA   8303

GCCTTACCGA TGCTAAAGGA TCCATGTTAC AATAATGGCA TTATTTGGAA ATCCCAGTGG   8363
```

```
TATTCCATGA ATAAAACCAC TATGAAGATA ATCCCACTCA ACAGACTCTC CGTTGGAGAA   8423

GGACAGCAAC ACCACCCTGG GAAAGCCAAA CAGTCAGACC AGACCTGTTT AGCATCAGTA   8483

GGACTTCCCT ACCATATCTG CTGGGTAGAT GAGTGAAACC AGTGTTCCAA ACCACTCCGG   8543

GCTTGTAGCA AACCATAGTC TCCTCATCTA CCAAGATGAG CAACCTTACC TCCTGATGTC   8603

CTAGCCAATC ACCAACTAGG AAACTTTGCA CAGTTTATTT AAAGTAACAG TTTGATTTTC   8663

ACAATATTTT TAAATTGGAG AAACATAACT TATCTTTGCA CTCACAAACC ACATAATGAG   8723

AAGAAACTCT AAGGGAAAAT GCTTGATCTG TGTGACCCGG GGCGCCATGC CAGAGCTGTA   8783

GTTCATGCCA GTGTTGTGCT CTGACAAGCC TTTTACAGAA TTACATGAGA TCTGCTTCCC   8843

TAGGACAAGG AGAAGGCAAA TCAACAGAGG CTGCACTTTA AAATGGAGAC ATAAAATAAC   8903

ATGCCAGAAC CATTTCCTAA AGCTCCTCAA TCAACCAACA AAATTGTGCT TTCAAATAAC   8963

CTGAGTTGAC CTCATCAGGA ATTTTGTGGC TCCTTCTCTT CTAACCTGCC TGAAGAAAGA   9023

TGGTCCACAG CAGCTGAGTC CGGGATGGAT AAGCTTAGGG ACAGAGGCCA ATTAGGGAAC   9083

TTTGGGTTTC TAGCCCTACT AGTAGTGAAT AAATTTAAAG TGTGGATGTG ACTATGAGTC   9143

ACAGCACAGA TGTTGTTTAA TAATATGTTT ATTTTATAAA TTGATATTTT AGGAATCTTT   9203

GGAGATATTT TCAGTTAGCA GATAATACTA TAAATTTTAT GTAACTGGCA ATGCACTTCG   9263

TAATAGACAG CTCTTCATAG ACTTGCAGAG GTAAAAAGAT TCCAGAATAA TGATATGTAC   9323

ATCTACGACT TGTTTTAG  GT GGC ACT TAC TCA AAA GCA TCT ACT CCT AAT     9373
                    Gly Gly Thr Tyr Ser Lys Ala Ser Thr Pro Asn
                                380                 385

GGT TAT GAT AAT GGC ATT ATT TGG GCC ACT TGG AAA ACC CGG TGG TAT     9421
Gly Tyr Asp Asn Gly Ile Ile Trp Ala Thr Trp Lys Thr Arg Trp Tyr
        390                 395                 400

TCC ATG AAG AAA ACC ACT ATG AAG ATA ATC CCA TTC AAC AGA CTC ACA     9469
Ser Met Lys Lys Thr Thr Met Lys Ile Ile Pro Phe Asn Arg Leu Thr
    405                 410                 415

ATT GGA GAA GGA CAG CAA CAC CAC CTG GGG GGA GCC AAA CAG GTC AGA     9517
Ile Gly Glu Gly Gln Gln His His Leu Gly Gly Ala Lys Gln Val Arg
420                 425                 430                 435

CCA GAG CAC CCT GCG GAA ACA GAA TAT GAC TCA CTT TAC CCT GAG GAT     9565
Pro Glu His Pro Ala Glu Thr Glu Tyr Asp Ser Leu Tyr Pro Glu Asp
                440                 445                 450

GAT TTG TAGAAAATTA ACTGCTAACT TCTATTGACC CACAAAGTTT CAGAAATTCT      9621
Asp Leu

CTGAAAGTTT CTTCCTTTTT TCTCTTACTA TATTTATTGA TTTCAAGTCT TCTATTAAGG   9681

ACATTTAGCC TTCAATGGAA ATTAAAACTC ATTTAGGACT GTATTTCCAA ATTACTGATA   9741

TCAGAGTTAT TTAAAAATTG TTTATTTGAG GAGATAACAT TTCAACTTTG TTCCTAAATA   9801

TATAATAATA AAATGATTGA CTTTATTTGC ATTTTTATGA CCACTTGTCA TTTATTTTGT   9861

CTTCGTAAAT TATTTTCATT ATATCAAATA TTTTAGTATG TACTTAATAA AATAGGAGAA   9921

CATTTTAGAG TTTCAAATTC CCAGGTATTT TCCTTGTTTA TTACCCCTAA ATCATTCCTA   9981

TTTAATTCTT CTTTTTAAAT GGAGAAAATT ATGTCTTTTT AATATGGTTT TTGTTTTGTT  10041

ATATATTCAC AGGCTGGAGA CGTTTAAAAG ACCGTTTCAA AAGAGATTTA CTTTTTTAAA  10101

GGACTTTATC TGAACAGAGA GATATAATAT TTTTCCTATT GGACAATGGA CTTGCAAAGC  10161

TTCACTTCAT TTTAAGAGCA AAAGACCCCA TGTTGAAAAC TCCATAACAG TTTTATGCTG  10221

ATGATAATTT ATCTACATGC ATTTCAATAA ACCTTTTGTT TCCTAAGACT AGATACATGG  10281

TACCTTTATT GACCATTAAA AAACCACCAC TTTTTGCCAA TTTACCAATT ACAATTGGGC  10341

AACCATCAGT AGTAATTGAG TCCTCATTTT ATGCTAAATG TTATGCCTAA CTCTTTGGGA  10401
```

```
GTTACAAAGG AAATAGCAAT TATGGCTTTT GCCCTCTAGG AGATACAGGA CAAATACAGG  10461

AAAATACAGC AACCCAAACT GACAATACTC TATACAAGAA CATAATCACT AAGCAGGAGT  10521

CACAGCCACA CAACCAAGAT GCATAGTATC CAAAGTGCAG CTG                    10564
```

(2) INFORMATION FOR SEQ ID NO: 6:

(i) SEQUENCE CHARACTERISTICS:
(A) LENGTH: 453 amino acids
(B) TYPE: amino acid
(D) TOPOLOGY: linear (ii) MOLECULE TYPE: protein (xi) SEQUENCE DESCRIPTION: SEQ ID NO: 6:

```
Met Ser Trp Ser Leu His Pro Arg Asn Leu Ile Leu Tyr Phe Tyr Ala
  1               5                  10                  15

Leu Leu Phe Leu Ser Ser Thr Cys Val Ala Tyr Val Ala Thr Arg Asp
             20                  25                  30

Asn Cys Cys Ile Leu Asp Glu Arg Phe Gly Ser Tyr Cys Pro Thr Thr
         35                  40                  45

Cys Gly Ile Ala Asp Phe Leu Ser Thr Tyr Gln Thr Lys Val Asp Lys
     50                  55                  60

Asp Leu Gln Ser Leu Glu Asp Ile Leu His Gln Val Glu Asn Lys Thr
 65                  70                  75                  80

Ser Glu Val Lys Gln Leu Ile Lys Ala Ile Gln Leu Thr Tyr Asn Pro
                 85                  90                  95

Asp Glu Ser Ser Lys Pro Asn Met Ile Asp Ala Ala Thr Leu Lys Ser
            100                 105                 110

Arg Ile Met Leu Glu Glu Ile Met Lys Tyr Glu Ala Ser Ile Leu Thr
        115                 120                 125

His Asp Ser Ser Ile Arg Tyr Leu Gln Glu Ile Tyr Asn Ser Asn Asn
    130                 135                 140

Gln Lys Ile Val Asn Leu Lys Glu Lys Val Ala Gln Leu Glu Ala Gln
145                 150                 155                 160

Cys Gln Glu Pro Cys Lys Asp Thr Val Gln Ile His Asp Ile Thr Gly
                165                 170                 175

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
        195                 200                 205

Glu Ile Asp Gly Ser Gly Asn Gly Trp Thr Val Phe Gln Lys Arg Leu
    210                 215                 220

Asp Gly Ser Val Asp Phe Lys Lys Asn Trp Ile Gln Tyr Lys Glu Gly
225                 230                 235                 240

Phe Gly His Leu Ser Pro Thr Gly Thr Thr Glu Phe Trp Leu Gly Asn
                245                 250                 255

Glu Lys Ile His Leu Ile Ser Thr Gln Ser Ala Ile Pro Tyr Ala Leu
            260                 265                 270

Arg Val Glu Leu Glu Asp Trp Asn Gly Arg Thr Ser Thr Ala Asp Tyr
        275                 280                 285

Ala Met Phe Lys Val Gly Pro Glu Ala Asp Lys Tyr Arg Leu Thr Tyr
    290                 295                 300

Ala Tyr Phe Ala Gly Gly Asp Ala Gly Asp Ala Phe Asp Gly Phe Asp
305                 310                 315                 320

Phe Gly Asp Asp Pro Ser Asp Lys Phe Phe Thr Ser His Asn Gly Met
                325                 330                 335
```

```
Gln Phe Ser Thr Trp Asp Asn Asp Asn Asp Lys Phe Glu Gly Asn Cys
            340                 345                 350

Ala Glu Gln Asp Gly Ser Gly Trp Trp Met Asn Lys Cys His Ala Gly
        355                 360                 365

His Leu Asn Gly Val Tyr Tyr Gln Gly Gly Thr Tyr Ser Lys Ala Ser
    370                 375                 380

Thr Pro Asn Gly Tyr Asp Asn Gly Ile Ile Trp Ala Thr Trp Lys Thr
385                 390                 395                 400

Arg Trp Tyr Ser Met Lys Lys Thr Thr Met Lys Ile Ile Pro Phe Asn
                405                 410                 415

Arg Leu Thr Ile Gly Glu Gly Gln Gln His His Leu Gly Gly Ala Lys
            420                 425                 430

Gln Val Arg Pro Glu His Pro Ala Glu Thr Glu Tyr Asp Ser Leu Tyr
        435                 440                 445

Pro Glu Asp Asp Leu
    450


(2) INFORMATION FOR SEQ ID NO: 7:

     (i) SEQUENCE CHARACTERISTICS:
          (A) LENGTH: 10807 base pairs
          (B) TYPE: nucleic acid
          (C) STRANDEDNESS: double
          (D) TOPOLOGY: linear

   (vii) IMMEDIATE SOURCE:
          (B) CLONE: ovine beta-lactoglobulin

    (xi) SEQUENCE DESCRIPTION: SEQ ID NO: 7:

ACGCGTGTCG ACCTGCAGGT CAACGGATCT CTGTGTCTGT TTTCATGTTA GTACCACACT     60

GTTTTGGTGG CTGTAGCTTT CAGCTACAGT CTGAAGTCAT AAAGCCTGGT ACCTCCAGCT    120

CTGTTCTCTC TCAAGATTGT GTTCTGCTGT TTGGGTCTTT AGTGTCTCCA CACAATTTTT    180

AGAATTGTTT GTTCTAGTTC TGTGAAAAAT GATGCTGGTA TTTTGATAAG GATTGCATTG    240

AATCTGTAAA GCTACAGATA TAGTCATTGG GTAGTACAGT CACTTTAACA ATATTAACTC    300

TTCACATCTG TGAGCATGAT ATATTTTCCC CCTCTATATC ATCTTCAATT CCTCCTATCA    360

GTTTCTTTCA TTGCAGTTTT CTGAGTACAG GTCTTACACC TCCTTGGTTA GAGTCATTCC    420

TCAGTATTTT ATTCCTTTGA TACAATTGTG AATGAGGTAA TTTTCTTAGT TTCTCTTTCT    480

GATAGCTCAT TGTTAGTGTA TATATAGAAA AGCAACAGAT TTCTATGTAT TAATTTTGTA    540

TCCTGCAACA GATTTCTATG TATTAATTTT GTATCCTGCT ACTTTACGGA ATTCACTTAT    600

TAGCTTTTTG GTGACATCTT GAGGATTTTC TGAAGAAAAT GGCATGGTAT GGTAGGACAA    660

GGTGTCATGT CATCTGCAAA CAGTGGCAGT TTTCCTTCTT CCCTTCCAAC CTGGATTTCT    720

TTGATTTCTT TCTGTCTGAG TACGACTAGG ATTCCCAATA CTATACCGAA TAAAAGTGGC    780

AAGAGTGGAC ATCCTTGTCT TATTTTTCTG ACCTTAGAGG AAATGCTTTC AGTTTTTCAC    840

CATTAATTAT AATGTTTACT GTGGGCTTGT CATATGTGGC CTTCATTATA TGGAGGTCTA    900

TTCCCTCTAT ACCCACCTTG TTGAGAGTTT TTATCATAAA AGTATGTTGA ATTTTGTCAA    960

AAGTTTTTCC TGCATCTATT GAGATGATTT TTACTCTTCA ATTCATTAAT GATTTTTATT   1020

CTTCATTTTG TTAATGATTT CCATTCTTCA ATTTGTTAAC GTGGTATATC ACATTGATTG   1080

ATTTGTGGAT ACCTTTGTAT CCCTGGGATA AACCTCACTT GATCATGAGC TTTCAATGTA   1140

TTTTTGAATT CACTTTGCTA ATATTCTGTT GGGTATTTTT GCATCTCTAT TCATCAATGA   1200

TATTGGCCTA AGAAAGGTTT TGTCTGGTTT TAGTATCAGG GTGATGCTGG CCTCATAGAG   1260
```

-continued

```
AGAGTTTAGA AGCATTTCCT CCTCTTTGAT TTTTCGGAAT AGTTTGAGTA GGATAGGTAT   1320
TAACTCTTCT TTAAATGTTT GGGGACTTCC CTGGTGAGCC GGTGGTTGAG AATCCGCCTC   1380
AGGGATGTGG GTTTGATCCC TGGTCAGGGA ACCATTAATA AGATCCCACA TGCTGCAGGC   1440
AACAAGCCCC CAAGCTGCAA CCACTGAGCT GCAACCGCTG CAGTGCCCAC AGGCCACGAC   1500
CAGAGAAAGC CCACATACAG CAGGGAAGAC CCAGCACAAC CGGAAAAAGG AGTTTGGTGG   1560
AATACAGCTG TGAAGCCGTC TGGTCCTGGA CTCCTGCTTG AGGGAATTTT TTAAAAATTA   1620
TTGATTCAAT TTCATTACTG GTAACTGGTC TGTTCATATT TTCTATTTCT TCCGGGTTCA   1680
GTCTTGGGAG ATTGTACATG CCTAGGAATG TGTCCGTTTC TTCTAGGTTG TCCATTTTAT   1740
TGGACATGCA TGGGAGCACA CAGCACCGAC CAGCGAGACT CATGCTGGCT TCCTGGGGCC   1800
AGGCTGGGGC CCCAAGCAGC ATGGCATCCT AGAGTGTGTG AAAGCCCACT GACCCTGCCC   1860
AGCCCCACAA TTTCATTCTG AGAAGTGATT CCTTGCTTCT GCACTTACAG GCCCAGGATC   1920
TGACCTGCTT CTGAGGAGCA GGGGTTTTGG CAGGACGGGG AGATGCTGAG AGCCGACGGG   1980
GGTCCAGGTC CCCTCCCAGG CCCCCCTGTC TGGGGCAGCC CTTGGGAAAG ATTGCCCCAG   2040
TCTCCCTCCT ACAGTGGTCA GTCCCAGCTG CCCCAGGCCA GAGCTGCTTT ATTTCCGTCT   2100
CTCTCTCTGG ATGGTATTCT CTGGAAGCTG AAGGTTCCTG AAGTTATGAA TAGCTTTGCC   2160
CTGAAGGGCA TGGTTTGTGG TCACGGTTCA CAGGAACTTG GGAGACCCTG CAGCTCAGAC   2220
GTCCCGAGAT TGGTGGCACC CAGATTTCCT AAGCTCGCTG GGGAACAGGG CGCTTGTTTC   2280
TCCCTGGCTG ACCTCCCTCC TCCCTGCATC ACCCAGTTCT GAAAGCAGAG CGGTGCTGGG   2340
GTCACAGCCT CTCGCATCTA ACGCCGGTGT CCAAACCACC CGTGCTGGTG TTCGGGGGGC   2400
TACCTATGGG GAAGGGCTTC TCACTGCAGT GGTGCCCCCC GTCCCCTCTG AGATCAGAAG   2460
TCCCAGTCCG GACGTCAAAC AGGCCGAGCT CCCTCCAGAG GCTCCAGGGA GGGATCCTTG   2520
CCCCCCCGCT GCTGCCTCCA GCTCCTGGTG CCGCACCCTT GAGCCTGATC TTGTAGACGC   2580
CTCAGTCTAG TCTCTGCCTC CGTGTTCACA CGCCTTCTCC CCATGTCCCC TCCGTGTCCC   2640
CGTTTTCTCT CACAAGGACA CCGGACATTA GATTAGCCCC TGTTCCAGCC TCACCTGAAC   2700
AGCTCACATC TGTAAAGACC TAGATTCCAA ACAAGATTCC AACCTGAAGT TCCCGGTGGA   2760
TGTGAGTTCT GGGGCGACAT CCTTCAACCC CATCACAGCT TGCAGTTCAT CGCAAAACAT   2820
GGAACCTGGG GTTTATCGTA AAACCCAGGT TCTTCATGAA ACACTGAGCT TCGAGGCTTG   2880
TTGCAAGAAT TAAAGGTGCT AATACAGATC AGGGCAAGGA CTGAAGCTGG CTAAGCCTCC   2940
TCTTTCCATC ACAGGAAAGG GGGGCCTGGG GGCGGCTGGA GGTCTGCTCC CGTGAGTGAG   3000
CTCTTTCCTG CTACAGTCAC CAACAGTCTC TCTGGGAAGG AAACCAGAGG CCAGAGAGCA   3060
AGCCGGAGCT AGTTTAGGAG ACCCCTGAAC CTCCACCCAA GATGCTGACC AGCCAGCGGG   3120
CCCCCTGGAA AGACCCTACA GTTCAGGGGG GAAGAGGGGC TGACCCGCCA GGTCCCTGCT   3180
ATCAGGAGAC ATCCCCGCTA TCAGGAGATT CCCCCACCTT GCTCCCGTTC CCCTATCCCA   3240
ATACGCCCAC CCCACCCCTG TGATGAGCAG TTTAGTCACT TAGAATGTCA ACTGAAGGCT   3300
TTTGCATCCC CTTTGCCAGA GGCACAAGGC ACCCACAGCC TGCTGGGTAC CGACGCCCAT   3360
GTGGATTCAG CCAGGAGGCC TGTCCTGCAC CCTCCCTGCT CGGGCCCCCT CTGTGCTCAG   3420
CAACACACCC AGCACCAGCA TTCCCGCTGC TCCTGAGGTC TGCAGGCAGC TCGCTGTAGC   3480
CTGAGCGGTG TGGAGGGAAG TGTCCTGGGA GATTTAAAAT GTGAGAGGCG GGAGGTGGGA   3540
GGTTGGGCCC TGTGGGCCTG CCCATCCCAC GTGCCTGCAT TAGCCCCAGT GCTGCTCAGC   3600
CGTGCCCCCG CCGCAGGGGT CAGGTCACTT TCCCGTCCTG GGGTTATTAT GACTCTTGTC   3660
```

-continued

```
ATTGCCATTG CCATTTTTGC TACCCTAACT GGGCAGCAGG TGCTTGCAGA GCCCTCGATA   3720
CCGACCAGGT CCTCCCTCGG AGCTCGACCT GAACCCCATG TCACCCTTGC CCCAGCCTGC   3780
AGAGGGTGGG TGACTGCAGA GATCCCTTCA CCCAAGGCCA CGGTCACATG GTTTGGAGGA   3840
GCTGGTGCCC AAGGCAGAGG CCACCCTCCA GGACACACCT GTCCCCAGTG CTGGCTCTGA   3900
CCTGTCCTTG TCTAAGAGGC TGACCCCGGA AGTGTTCCTG GCACTGGCAG CCAGCCTGGA   3960
CCCAGAGTCC AGACACCCAC CTGTGCCCCC GCTTCTGGGG TCTACCAGGA ACCGTCTAGG   4020
CCCAGAGGGG ACTTCCTGCT TGGCCTTGGA TGGAAGAAGG CCTCCTATTG TCCTCGTAGA   4080
GGAAGCCACC CCGGGGCCTG AGGATGAGCC AAGTGGGATT CCGGGAACCG CGTGGCTGGG   4140
GGCCCAGCCC GGGCTGGCTG GCCTGCATGC CTCCTGTATA AGGCCCCAAG CCTGCTGTCT   4200
CAGCCCTCCA CTCCCTGCAG AGCTCAGAAG CACGACCCCA GGGATATCCC TGCAGCCATG   4260
AAGTGCCTCC TGCTTGCCCT GGGCCTGGCC CTCGCCTGTG GCGTCCAGGC CATCATCGTC   4320
ACCCAGACCA TGAAAGGCCT GGACATCCAG AAGGTTCGAG GGTTGGCCGG GTGGGTGAGT   4380
TGCAGGGCGG GCAGGGGAGC TGGGCCTCAG AGAGCCAAGA GAGGCTGTGA CGTTGGGTTC   4440
CCATCAGTCA GCTAGGGCCA CCTGACAAAT CCCCGCTGGG GCAGCTTCAA CCAGGCGTTC   4500
ACTGTCTTGC ATTCTGGAGG CTGGAAGCCC AAGATCCAGG TGTTGGCAGG GCTGGCTTCT   4560
CCTGCGGCCG CTCTCTGGGG AGCAGACGGC CGTCTTCTCC AGTCCTCTGC GCGCCCTGAT   4620
TTCCTCTTCC TGTGAGGCCA CCAGGCCTGC TGGAAACACG CCTGCCTGCG CAGCTTCACA   4680
CGACCTTTGT CATCTCTTTA AAGGCCATGT CTCCAGAGTC ATGTGTTGAA GTTCTGGGGG   4740
TTAGTGGGAC ACAGTTCAGC CCCTAAAAGA GTCTCTCTGC CCCTCAAATT TTCCCCACCT   4800
CCAGCCATGT CTCCCCAAGA TCCAAATGTT GCTACATGTG GGGGGGCTCA TCTGGGTCCC   4860
TCTTTGGGTT CAGTGTGAGT CTGGGGAGAG CATTCCCCAG GGTGCAGAGT TGGGGGGAGT   4920
ATCTCAGGGC TGCCCAGGCC GGGGTGGGAC AGAGAGCCCA CTGTGGGGCT GGGGGCCCCT   4980
TCCCACCCCC AGAGTGCAAC TCAAGGTCCC TCTCCAGGTG GCGGGGACTT GGCACTCCTT   5040
GGCTATGGCG GCCAGCGACA TCTCCCTGCT GGATGCCCAG AGTGCCCCCC TGAGAGTGTA   5100
CGTGGAGGAG CTGAAGCCCA CCCCCGAGGG CAACCTGGAG ATCCTGCTGC AGAAATGGTG   5160
GGCGTCTCTC CCCAACATGG AACCCCCACT CCCCAGGGCT GTGGACCCCC CGGGGGGTGG   5220
GGTGCAGGAG GGACCAGGGC CCCAGGGCTG GGGAAGAGGG CTCAGAGTTT ACTGGTACCC   5280
GGCGCTCCAC CCAAGGCTGC CCACCCAGGG CTTTTTTTTT TTTTAAACTT TTATTAATTT   5340
GATGCTTCAG AACATCATCA AACAAATGAA CATAAAACAT TCATTTTTGT TTACTTGGAA   5400
GGGGAGATAA AATCCTCTGA AGTGGAAATG CATAGCAAAG ATACATACAA TGAGGCAGGT   5460
ATTCTGAATT CCCTGTTAGT CTGAGGATTA CAAGTGTATT TGAGCAACAG AGAGACATTT   5520
TCATCATTTC TAGTCTGAAC ACCTCAGTAT CTAAAATGAA CAAGAAGTCC TGGAAACGAA   5580
GCAGTGTGGG GATAGGCCCG TGTGAAGGCT GCTGGGAGGC AGCAGACCTG GGTCTTCGGG   5640
CTCAAGCAGT TCCCGCTACC AGCCCTGTCC ACCTCAGACG GGGGTCAGGG TGCAGGAGAG   5700
AGCTGGATGG GTGTGGGGGC AGAGATGGGG ACCTGAACCC CAGGGCTGCC TTTTGGGGGT   5760
GCCTGTGGTC AAGGCTCTCC CTGACCTTTT CTCTCTGGCT TCATCTGACT TCTCCTGGCC   5820
CATCCACCCG GTCCCCTGTG GCCTGAGGTG ACAGTGAGTG CGCCGAGGCT AGTTGGCCAG   5880
CTGGCTCCTA TGCCCATGCC ACCCCCCTCC AGCCCTCCTG GGCCAGCTTC TGCCCCTGGC   5940
CCTCAGTTCA TCCTGATGAA AATGGTCCAT GCCAATGGCT CAGAAAGCAG CTGTCTTTCA   6000
GGGAGAACGG CGAGTGTGCT CAGAAGAAGA TTATTGCAGA AAAAACCAAG ATCCCTGCGG   6060
```

-continued

```
TGTTCAAGAT CGATGGTGAG TCCGGGTCCC TGGGGGACAC CCACCACCCC CGCCCCCGGG   6120
GACTGTGGAC AGGTTCAGGG GGCTGGCGTC GGGCCCTGGG ATGCTAAGGG ACTGGTGGTG   6180
ATGAAGACAC TGCCTTGACA CCTGCTTCAC TTGCCTCCCC TGCCACCTGC CCGGGGCCTT   6240
GGGGCGGTGG CCATGGGCAG GTCCCGGCTG GCGGGCTAAC CCACCAGGGT GACACCCGAG   6300
CTCTCTTTGC TGGGGGGCGG GCGGTGCTCT GGGCCCTCAG GCTGAGCTCA GGAGGTACCT   6360
GTGCCCTCCC AGGGGTAACC GAGAGCCGTT GCCCACTCCA GGGGCCCAGG TGCCCCACGA   6420
CCCCAGCCCG CTCCACAGCT CCTTCATCTC CTGGAGACAA ACTCTGTCCG CCCTCGCTCA   6480
TTCACTTGTT CGTCCTAAAT CCGAGATGAT AAAGCTTCGA GGGGGGGTTG GGGTTCCATC   6540
AGGGCTGCCC TTCCGCCGGG CAGCCTGGGC CACATCTGCC CTTGGCCCCC TCAGGACTCA   6600
CTCTGACTGG AGGCCCTGCA CTGACTGACG CCAGGGTGCC CAGCCCAGGG TCTCTGGCGC   6660
CATCCAGCTG CACTGGGTTT GGGTGCTGGT CCTGCCCCCA AGCTGCCCGG ACACCACAGG   6720
CAGCCGGGGC TGCCCACTGG CCTCGGTCAG GGTGAGCCCC AGCTGCCCCC GCTCAGGGCT   6780
TGCCCCGACA ATGACCCCAT CCTCAGGACG CACCCCCCTT CCCTTGCTGG GCAGTGTCCA   6840
GCCCCACCCG AGATCGGGGG AAGCCCTATT TCTTGACAAC TCCAGTCCCT GGGGGAGGGG   6900
GCCTCAGACT GAGTGGTGAG TGTTCCCAAG TCCAGGAGGT GGTGGAGGGT CCTGGCGGAT   6960
CCAGAGTTGA CAGTGAGGGC TTCCTGGGCC CCATGCGCCT GGCAGTGGCA GCAGGGAAGA   7020
GGAAGCACCA TTTCAGGGGT GGGGGATGCC AGAGGCGCTC CCCACCCCGT CTTCGCCGGG   7080
TGGTGACCCC GGGGGAGCCC CGCTGGTCGT GGAGGGTGCT GGGGGCTGAC TAGCAACCCC   7140
TCCCCCCCCG TTGGAACTCA CTTTTCTCCC GTCTTGACCG CGTCCAGCCT TGAATGAGAA   7200
CAAAGTCCTT GTGCTGGACA CCGACTACAA AAAGTACCTG CTCTTCTGCA TGGAAAACAG   7260
TGCTGAGCCC GAGCAAAGCC TGGCCTGCCA GTGCCTGGGT GGGTGCCAAC CCTGGCTGCC   7320
CAGGGAGACC AGCTGCGTGG TCCTTGCTGC AACAGGGGGT GGGGGGTGGG AGCTTGATCC   7380
CCAGGAGGAG GAGGGGTGGG GGGTCCCTGA GTCCCGCCAG GAGAGAGTGG TCGCATACCG   7440
GGAGCCAGTC TGCTGTGGGC CTGTGGGTGG CTGGGGACGG GGGCCAGACA CACAGGCCGG   7500
GAGACGGGTG GGCTGCAGAA CTGTGACTGG TGTGACCGTC GCGATGGGGC CGGTGGTCAC   7560
TGAATCTAAC AGCCTTTGTT ACCGGGGAGT TTCAATTATT TCCCAAAATA AGAACTCAGG   7620
TACAAAGCCA TCTTTCAACT ATCACATCCT GAAAACAAAT GGCAGGTGAC ATTTTCTGTG   7680
CCGTAGCAGT CCCACTGGGC ATTTTCAGGG CCCCTGTGCC AGGGGGGCGC GGGCATCGGC   7740
GAGTGGAGGC TCCTGGCTGT GTCAGCCGGC CCAGGGGGAG GAAGGGACCC GGACAGCCAG   7800
AGGTGGGGGG CAGGCTTTCC CCCTGTGACC TGCAGACCCA CTGCACTGCC CTGGGAGGAA   7860
GGGAGGGGAA CTAGGCCAAG GGGGAAGGGC AGGTGCTCTG GAGGGCAAGG GCAGACCTGC   7920
AGACCACCCT GGGGAGCAGG GACTGACCCC CGTCCCTGCC CCATAGTCAG GACCCCGGAG   7980
GTGGACAACG AGGCCCTGGA GAAATTCGAC AAAGCCCTCA AGGCCCTGCC CATGCACATC   8040
CGGCTTGCCT TCAACCCGAC CCAGCTGGAG GGTGAGCACC CAGGCCCCGC CCTTCCCCAG   8100
GGCAGGAGCC ACCCGGCCCC GGGACGACCT CCTCCCATGG TGACCCCCAG CTCCCCAGGC   8160
CTCCCAGGAG GAAGGGGTGG GGTGCAGCAC CCCGTGGGGG CCCCCTCCCC ACCCCCTGCC   8220
AGGCCTCTCT TCCCGAGGTG TCCAGTCCCA TCCTGACCCC CCCATGACTC TCCCTCCCCC   8280
ACAGGGCAGT GCCACGTCTA GGTGAGCCCC TGCCGGTGCC TCTGGGGTAA GCTGCCTGCC   8340
CTGCCCCACG TCCTGGGCAC ACACATGGGG TAGGGGGTCT TGGTGGGGCC TGGGACCCCA   8400
CATCAGGCCC TGGGGTCCCC CCTGTGAGAA TGGCTGGAAG CTGGGGTCCC TCCTGGCGAC   8460
```

-continued

```
TGCAGAGCTG GCTGGCCGCG TGCCACTCTT GTGGGTGACC TGTGTCCTGG CCTCACACAC   8520
TGACCTCCTC CAGCTCCTTC CAGCAGAGCT AAGGCTAAGT GAGCCAGAAT GGTACCTAAG   8580
GGGAGGCTAG CGGTCCTTCT CCCGAGGAGG GGCTGTCCTG GAACCACCAG CCATGGAGAG   8640
GCTGGCAAGG GTCTGGCAGG TGCCCCAGGA ATCACAGGGG GGCCCCATGT CCATTTCAGG   8700
GCCCGGGAGC CTTGGACTCC TCTGGGGACA GACGACGTCA CCACCGCCCC CCCCCCATCA   8760
GGGGGACTAG AAGGGACCAG GACTGCAGTC ACCCTTCCTG GGACCCAGGC CCCTCCAGGC   8820
CCCTCCTGGG GCTCCTGCTC TGGGCAGCTT CTCCTTCACC AATAAAGGCA TAAACCTGTG   8880
CTCTCCCTTC TGAGTCTTTG CTGGACGACG GGCAGGGGGT GGAGAAGTGG TGGGGAGGGA   8940
GTCTGGCTCA GAGGATGACA GCGGGGCTGG GATCCAGGGC GTCTGCATCA CAGTCTTGTG   9000
ACAACTGGGG GCCCACACAC ATCACTGCGG CTCTTTGAAA CTTTCAGGAA CCAGGGAGGG   9060
ACTCGGCAGA GACATCTGCC AGTTCACTTG GAGTGTTCAG TCAACACCCA AACTCGACAA   9120
AGGACAGAAA GTGGAAAATG GCTGTCTCTT AGTCTAATAA ATATTGATAT GAAACTCAAG   9180
TTGCTCATGG ATCAATATGC CTTTATGATC CAGCCAGCCA CTACTGTCGT ATCAACTCAT   9240
GTACCCAAAC GCACTGATCT GTCTGGCTAA TGATGAGAGA TTCCCAGTAG AGAGCTGGCA   9300
AGAGGTCACA GTGAGAACTG TCTGCACACA CAGCAGAGTC CACCAGTCAT CCTAAGGAGA   9360
TCAGTCCTGG TGTTCATTGG AGGACTGATG TTGAAGCTGA AACTCCAATG CTTTGGCCAC   9420
CTGATGTGAA GAGCTGACTC ATTTGAAAAG ACCCTGATGC TGGGAAAGAT TGAGGGCAGG   9480
AGGAGAAGGG GACGACAGAG GATGAGATGG TTGGATGGCA TCACCAACAC AATGGACATG   9540
GGTTTGGGTG GACTCCAGGA GTTGGTGATG GACAGGGAGG CCTGGCGTGC TACGGAAGCG   9600
GTTTATGGGG TCACAAAGAC TGAGTGACTG AACTGAGCTG AACTGAATGG AAATGAGGTA   9660
TACAGCAAAG TGGGGATTTT TTAGATAATA AGAATATACA CATAACATAG TGTATACTCA   9720
TATTTTTATG CATACCTGAA TGCTCAGTCA CTCAGTCGTA TCTGACTCTG TGACCTATGG   9780
ACCGTAGCCT TCCAGGTTTC TTCTGTCCAC AGAATTCTCC AAGGCAAGAA TACTGGAGTG   9840
GGTAGCCATT TCCTCCTCCA GGGGATCCTC CCGACCCAGG GATTGAACCG GCATCTCCTG   9900
TATTGGCAGG TGGATTCTTT ACCACTGTGC CACCAGGGAA GCCCGTGTTA CTCTCTATGT   9960
CCCACTTAAT TACCAAAGCT GCTCCAAGAA AAAGCCCCTG TGCCCTCTGA GCTTCCCGGC  10020
CTGCAGAGGG TGGTGGGGGT AGACTGTGAC CTGGGAACAC CCTCCCGCTT CAGGACTCCC  10080
GGGCCACGTG ACCCACAGTC CTGCAGACAG CCGGGTAGCT CTGCTCTTCA AGGCTCATTA  10140
TCTTTAAAAA AAACTGAGGT CTATTTTGTG ACTTCGCTGC CGTAACTTCT GAACATCCAG  10200
TGCGATGGAC AGGACCTCCT CCCCAGGCCT CAGGGGCTTC AGGGAGCCAG CCTTCACCTA  10260
TGAGTCACCA GACACTCGGG GGTGGCCCCG CCTTCAGGGT GCTCACAGTC TTCCCATCGT  10320
CCTGATCAAA GAGCAAGACC AATGACTTCT TAGGAGCAAG CAGACACCCA CAGGACACTG  10380
AGGTTCACCA GAGCTGAGCT GTCCTTTTGA ACCTAAAGAC ACACAGCTCT CGAAGGTTTT  10440
CTCTTTAATC TGGATTTAAG GCCTACTTGC CCCTCAAGAG GGAAGACAGT CCTGCATGTC  10500
CCCAGGACAG CCACTCGGTG GCATCCGAGG CCACTTAGTA TTATCTGACC GCACCCTGGA  10560
ATTAATCGGT CCAAACTGGA CAAAAACCTT GGTGGGAAGT TTCATCCCAG AGGCCTCAAC  10620
CATCCTGCTT TGACCACCCT GCATCTTTTT TTCTTTTATG TGTATGCATG TATATATATA  10680
TATATATTTT TTTTTTTTTC ATTTTTTGGC TGTGCTGGCT GTTCGTTGCA GTTCGGTGCG  10740
```

CAGGCTTCTC TCTAGTTTCT CTCTAGTCTT CTCTTATCAC AGAGCAGTCT CTAGACGATC 10800

GACGCGT 10807

(2) INFORMATION FOR SEQ ID NO: 8:

(i) SEQUENCE CHARACTERISTICS:
(A) LENGTH: 47 base pairs
(B) TYPE: nucleic acid
(C) STRANDEDNESS: single
(D) TOPOLOGY: linear (xi) SEQUENCE DESCRIPTION: SEQ ID NO: 8:

AATTCCGATC GACGCGTCGA CGATATACTC TAGACGATCG ACGCGTA 47

(2) INFORMATION FOR SEQ ID NO: 9:

(i) SEQUENCE CHARACTERISTICS:
(A) LENGTH: 24 base pairs
(B) TYPE: nucleic acid
(C) STRANDEDNESS: single
(D) TOPOLOGY: linear (vii) IMMEDIATE SOURCE:
(B) CLONE: BLGAMP3

(xi) SEQUENCE DESCRIPTION: SEQ ID NO: 9:

TGGATCCCCT GCCGGTGCCT CTGG 24

(2) INFORMATION FOR SEQ ID NO: 10:

(i) SEQUENCE CHARACTERISTICS:
(A) LENGTH: 24 base pairs
(B) TYPE: nucleic acid
(C) STRANDEDNESS: single
(D) TOPOLOGY: linear (vii) IMMEDIATE SOURCE:
(B) CLONE: BLGAMP4

(xi) SEQUENCE DESCRIPTION: SEQ ID NO: 10:

AACGCGTCAT CCTCTGTGAG CCAG 24

(2) INFORMATION FOR SEQ ID NO: 11:

(i) SEQUENCE CHARACTERISTICS:
(A) LENGTH: 10 base pairs
(B) TYPE: nucleic acid
(C) STRANDEDNESS: single
(D) TOPOLOGY: linear (vii) IMMEDIATE SOURCE:
(B) CLONE: ZC6839

(xi) SEQUENCE DESCRIPTION: SEQ ID NO: 11:

ACTACGTAGT 10

(2) INFORMATION FOR SEQ ID NO: 12:

(i) SEQUENCE CHARACTERISTICS:
(A) LENGTH: 42 base pairs
(B) TYPE: nucleic acid
(C) STRANDEDNESS: single
(D) TOPOLOGY: linear (vii) IMMEDIATE SOURCE:
(B) CLONE: ZC6632

(xi) SEQUENCE DESCRIPTION: SEQ ID NO: 12:

CGACGCGGAT CCTACGTACC TGCAGCCATG TTTTCCATGA GG 42

(2) INFORMATION FOR SEQ ID NO: 13:

(i) SEQUENCE CHARACTERISTICS:
(A) LENGTH: 21 base pairs
(B) TYPE: nucleic acid
(C) STRANDEDNESS: single
(D) TOPOLOGY: linear (vii) IMMEDIATE SOURCE:
(B) CLONE: ZC6627

(xi) SEQUENCE DESCRIPTION: SEQ ID NO: 13:

AGGGCTTCGG CAAGCTTCAG G 21

(2) INFORMATION FOR SEQ ID NO: 14:

(i) SEQUENCE CHARACTERISTICS:
(A) LENGTH: 24 base pairs
(B) TYPE: nucleic acid
(C) STRANDEDNESS: single
(D) TOPOLOGY: linear (vii) IMMEDIATE SOURCE:
(B) CLONE: ZC6521

(xi) SEQUENCE DESCRIPTION: SEQ ID NO: 14:

GCCAAAGACT TACTTCCCTC TAGA 24

(2) INFORMATION FOR SEQ ID NO: 15:

(i) SEQUENCE CHARACTERISTICS:
(A) LENGTH: 30 base pairs
(B) TYPE: nucleic acid
(C) STRANDEDNESS: single
(D) TOPOLOGY: linear (vii) IMMEDIATE SOURCE:
(B) CLONE: ZC6520

(xi) SEQUENCE DESCRIPTION: SEQ ID NO: 15:

GCATGAACGT CGCGTGGTGG TTGTGCTACC 30

(2) INFORMATION FOR SEQ ID NO: 16:

(i) SEQUENCE CHARACTERISTICS:
(A) LENGTH: 30 base pairs
(B) TYPE: nucleic acid
(C) STRANDEDNESS: single
(D) TOPOLOGY: linear (vii) IMMEDIATE SOURCE:
(B) CLONE: ZC6519

(xi) SEQUENCE DESCRIPTION: SEQ ID NO: 16:

ACCACGCGAC GTTCATGCTC TAAAACCGTT 30

(2) INFORMATION FOR SEQ ID NO: 17:

(i) SEQUENCE CHARACTERISTICS:
(A) LENGTH: 36 base pairs
(B) TYPE: nucleic acid
(C) STRANDEDNESS: single
(D) TOPOLOGY: linear (vii) IMMEDIATE SOURCE:
(B) CLONE: ZC6518

(xi) SEQUENCE DESCRIPTION: SEQ ID NO: 17:

GCTGCGGGAT CCTACGTACT AGGGGGACAG GGAAGG 36

(2) INFORMATION FOR SEQ ID NO: 18:

(i) SEQUENCE CHARACTERISTICS:
(A) LENGTH: 45 base pairs
(B) TYPE: nucleic acid
(C) STRANDEDNESS: single
(D) TOPOLOGY: linear (vii) IMMEDIATE SOURCE:
(B) CLONE: ZC6629

(xi) SEQUENCE DESCRIPTION: SEQ ID NO: 18:

CGACGCGAAT TCTACGTACC TGCAGCCATG AAAAGGATGG TTTCT 45

(2) INFORMATION FOR SEQ ID NO: 19:

(i) SEQUENCE CHARACTERISTICS:
(A) LENGTH: 45 base pairs
(B) TYPE: nucleic acid
(C) STRANDEDNESS: single
(D) TOPOLOGY: linear (vii) IMMEDIATE SOURCE:
(B) CLONE: ZC6630

(xi) SEQUENCE DESCRIPTION: SEQ ID NO: 19:

CGACGCGAAT TCTACGTACC TGCAGCCATG AAACATCTAT TATTG 45

(2) INFORMATION FOR SEQ ID NO: 20:

(i) SEQUENCE CHARACTERISTICS:
(A) LENGTH: 21 base pairs
(B) TYPE: nucleic acid
(C) STRANDEDNESS: single
(D) TOPOLOGY: linear (vii) IMMEDIATE SOURCE:
(B) CLONE: ZC6625

(xi) SEQUENCE DESCRIPTION: SEQ ID NO: 20:

GTGAGATTTT CAGATCTTGT C 21

(2) INFORMATION FOR SEQ ID NO: 21:

(i) SEQUENCE CHARACTERISTICS:
(A) LENGTH: 21 base pairs
(B) TYPE: nucleic acid
(C) STRANDEDNESS: single
(D) TOPOLOGY: linear (vii) IMMEDIATE SOURCE:
(B) CLONE: ZC6626

(xi) SEQUENCE DESCRIPTION: SEQ ID NO: 21:

AAGAATTACT GTGGCCTACC A 21

(2) INFORMATION FOR SEQ ID NO: 22:

(i) SEQUENCE CHARACTERISTICS:
(A) LENGTH: 33 base pairs
(B) TYPE: nucleic acid
(C) STRANDEDNESS: single
(D) TOPOLOGY: linear (vii) IMMEDIATE SOURCE:
(B) CLONE: ZC6624

(xi) SEQUENCE DESCRIPTION: SEQ ID NO: 22:

GCTGCGGAAT TCTACGTACT ATTGCTGTGG GAA 33

(2) INFORMATION FOR SEQ ID NO: 23:

(i) SEQUENCE CHARACTERISTICS:
(A) LENGTH: 45 base pairs
(B) TYPE: nucleic acid
(C) STRANDEDNESS: single
(D) TOPOLOGY: linear (vii) IMMEDIATE SOURCE:
(B) CLONE: ZC6514

(xi) SEQUENCE DESCRIPTION: SEQ ID NO: 23:

CGACGCGGAT CCTACGTACC TGCAGCCATG AGTTGGTCCT TGCAC 45

(2) INFORMATION FOR SEQ ID NO: 24:

(i) SEQUENCE CHARACTERISTICS:
(A) LENGTH: 21 base pairs
(B) TYPE: nucleic acid
(C) STRANDEDNESS: single
(D) TOPOLOGY: linear (vii) IMMEDIATE SOURCE:
(B) CLONE: zc6517

(xi) SEQUENCE DESCRIPTION: SEQ ID NO: 24:

GTCTCTGGTA GCAACATACT A 21

(2) INFORMATION FOR SEQ ID NO: 25:

(i) SEQUENCE CHARACTERISTICS:
(A) LENGTH: 22 base pairs
(B) TYPE: nucleic acid
(C) STRANDEDNESS: single
(D) TOPOLOGY: linear (vii) IMMEDIATE SOURCE:
(B) CLONE: zc6516

(xi) SEQUENCE DESCRIPTION: SEQ ID NO: 25:

GGGTTTCTAG CCCTACTAGT AG 22

(2) INFORMATION FOR SEQ ID NO: 26:

(i) SEQUENCE CHARACTERISTICS:
(A) LENGTH: 22 base pairs
(B) TYPE: nucleic acid
(C) STRANDEDNESS: single
(D) TOPOLOGY: linear (vii) IMMEDIATE SOURCE:
(B) CLONE: zc6515

(xi) SEQUENCE DESCRIPTION: SEQ ID NO: 26:

GGGTTTCTAG CCCTACTAGT AG 22

(2) INFORMATION FOR SEQ ID NO: 27:

(i) SEQUENCE CHARACTERISTICS:
(A) LENGTH: 47 base pairs
(B) TYPE: nucleic acid
(C) STRANDEDNESS: single
(D) TOPOLOGY: linear (xi) SEQUENCE DESCRIPTION: SEQ ID NO: 27:

AAGCTACGCG TCGATCGTCT AGAGTATATC GTCGACGCGT CGATCGG 47

We claim:

1. A method for producing biocompetent fibrinogen comprising:

providing a first DNA segment encoding a secretion signal operably linked to a heterologous fibrinogen Aα chain, *the DNA segment comprising genomic DNA encoding the Aα chain,* a second DNA segment encoding a secretion signal operably linked to a heterologous fibrinogen Bβ chain, *the DNA segment comprising genomic DNA encoding the Bβ chain,* and a third DNA segment encoding a secretion signal operably linked to a heterologous fibrinogen γ chain, *the DNA segment comprising genomic DNA encoding the γ chain,* wherein each chain is from the same species, and wherein each of said first, second and third segments is operably linked to additional DNA segments required for its expression in the mammary gland of a host female mammal *and the first, second, third segments are linked in a single vector*;

introducing said DNA segments into a fertilized egg of a non-human mammalian species heterologous to the species of origin of said fibrinogen chains;

inserting said egg into an oviduct or uterus of a female of said mammalian species to obtain offspring carrying said DNA segments;

breeding said offspring to produce female progeny that express said first, second and third DNA segments and produce milk containing biocompetent fibrinogen encoded by said segments;

collecting milk from said female progeny; and and recovering the biocompetent fibrinogen from the milk.

2. A method according to claim 1 wherein said species into which said DNA segments are introduced is selected from the group consisting of sheep, pigs, goats, and cattle.

[3. A method according to claim 1 wherein each of said first, second and third DNA segments comprises an intron.]

[4. A method according to claim 1 wherein the molar ratio of said first, second and third DNA segments is within the range of 0.5-1:0.5-1:0.5-1.]

5. A method according to claim 1 wherein each of said first, second and third DNA segments is operably linked to a transcription promoter selected from the group consisting of casein, β-lactoglobulin, α-lactalbumin and whey acidic protein gene promoters.

6. A method according to claim 1 wherein said first, second and third DNA segments are expressed under the control of a β-lactoglobulin promoter.

7. A method according to claim 1 wherein said introducing step comprises injecting said first, second and third DNA segments into a pronucleus of said fertilized egg.

8. A method according to claim 1 wherein said fibrinogen is human fibrinogen.

9. A method according to claim 1 wherein said second DNA segment comprises a sequence of nucleotides as shown in SEQ ID NO: 3 from nucleotide 470 to nucleotide 8100.

10. A method according to claim 1 wherein said second DNA segment comprises a sequence of nucleotides as shown in SEQ ID NO: 3 from nucleotide 512 to nucleotide 8100.

11. A method according to claim 1 wherein said species into which said DNA segments is introduced is sheep.

12. A method of producing biocompetent fibrinogen comprising:

incorporating *into operable linkage* a [first] DNA segment encoding a secretion signal [operably linked to], *a genomic DNA segment encoding* an Aα chain of fibrinogen [into a β-lactoglobulin gene] *and an additional segment required for expression of the Aα* chain in the mammary gland of a mammal to produce a first gene fusion[comprising a β-lactoglobulin promoter operably linked to the first DNA segment];

incorporating *into operable linkage* a [second] DNA segment encoding a secretion signal [operably linked to], *a genomic DNA segment encoding* a Bβ chain of fibrinogen [into a β-lactoglobulin gene] *and an additional segment required for expression of the Bβ chain* to produce a second gene fusion [comprising a β-lactoglobulin promoter operably linked to the second DNA segment];

incorporating *into operable linkage* a [third] DNA segment encoding a secretion signal [operably linked to], *a genomic DNA segment encoding* a γ chain of fibrinogen *and an additional segment required for expression of the* γ chain [into a β-lactoglobulin gene] to produce a third gene fusion, [comprising a β-lactoglobulin promoter operably linked to the third DNA segment] wherein each of said first, second and third segments are of the same species;

*linking the first, second and third gene fusions in a single vector;* introducing said first, second and third gene fusions into the germ line of a non-human mammal so that said DNA segments are expressed in a mammary gland of said mammal or its female progeny and biocompetent fibrinogen is secreted into milk of said mammal or its female progeny;

obtaining milk from said mammal or its female progeny; and recovering said fibrinogen from said milk.

13. A method according to claim 12 wherein said mammal is a sheep, pig, goat or cow.

[14. A method according to claim 12 wherein each of said first, second and third gene fusions comprises an intron.]

[15. A method according to claim 12 wherein the molar ratio of said first, second and third gene fusions introduced is within the range of 0.5-1:0.5-1:0.5-1.]

16. A method according to claim 12 wherein said introducing step comprises injecting said first, second and third gene fusions into a pronucleus of a fertilized egg and inserting said egg into an oviduct of a pseudopregnant female to produce female offspring carrying said gene fusions in the germ line, wherein said egg and said pseudopregnant female are of the same species.

17. A method according to claim 12 wherein said mammal is a sheep.

[18. A method for producing biocompetent fibrinogen comprising:

providing a transgenic female non-human mammal carrying in its germline heterologous DNA segments encoding Aα, Bβ and γ chains of flbrinogen, wherein said segments are expressed in a mammary gland of said mammal and biocompetent fibrinogen encoded by said segments is secreted into milk of said mammal;

collecting milk from said mammal; and recovering said biocompetent fibrinogen from said milk.]

[19. A method according to claim 18 wherein said mammal is a sheep, pig, goat or cow.]

[20. A method according to claim 18 wherein said mammal is a sheep.]

[21. A transgenic non-human female mammal that produces recoverable amounts of biocompetent human fibrinogen in its milk, wherein said mammal comprises:

a first DNA segment encoding a secretion signal operably linked to a heterologous fibrinogen Aα chain, a second DNA segment encoding a secretion signal operably linked to a heterologous fibrinogen Bβ chain, and a third DNA segment encoding a secretion signal operably linked to a heterologous fibrinogen γ chain, and further wherein each chain is derived from the same species and is operably linked to additional DNA segments required for its expression in the mammary gland of a host female mammal.]

[22. A mammal according to claim 21 wherein said mammal is a sheep.]

23. A process for producing a transgenic offspring of a mammal comprising:

providing a first DNA segment encoding a secretion signal operably linked to a heterologous fibrinogen Aα chain, *the DNA segment comprising genomic DNA encoding the Aα chain;* a second DNA segment encoding a secretion signal operably linked to a heterologous fibrinogen Bβ chain, *the DNA segment comprising genomic DNA encoding the Bβ chain;* and a third DNA segment encoding a secretion signal operably linked to a heterologous fibrinogen γ chain, *the DNA segment comprising genomic DNA encoding the γ chain;* wherein each chain is derived from the same species, and wherein each of said first, second and third segments is operably linked to additional DNA segments required for its expression in the mammary gland of a host female mammal;

*linking the first, second and third segments in a single vector;* introducing said DNA segments into a fertilized egg of a non-human mammalian species heterologous to the species of origin of said fibrinogen chains;

inserting said fertilized egg into an oviduct or uterus of a female of said mammalian species; and allowing said fertilized egg to develop thereby producing transgenic offspring carrying said first, second and third DNA segments, wherein female progeny of said mammal express said DNA segments in a mammary gland to produce biocompetent fibrinogen.

24. A process according to claim 23 wherein said offspring is female.

25. A process according to claim 23 wherein said offspring is male.

[26. A non-human mammal produced according to the process of claim 23.]

[27. A non-human mammal according to claim 26 wherein said mammal is female.]

[28. A non-human female mammal according to claim 27 that produces milk containing biocompetent fibrinogen encoded by said DNA segments.]

[29. A non-human mammal according to claim 26 wherein said mammal is male.]

[30. A non-human mammal carrying in its germline DNA segments encoding human Aα, Bβ and γ chains of fibrinogen, wherein female progeny of said mammal express said DNA segments in a mammary gland to produce biocompetent human fibrinogen.]

[31. A mammal non-human according to claim 30 wherein said mammal is female.]

[32. A mammal non-human according to claim 30 wherein said mammal is male.]

[33. A mammal according to claim 30, wherein said mammal is a sheep.]

*34. A set of DNA sequences comprising:*

*a first DNA segment encoding a secretion signal operably linked to a heterologous fibrinogen Aα chain, the DNA segment comprising genomic DNA encoding the Aα chain;*

*a second DNA segment encoding a secretion signal operably linked to a heterologous fibrinogen Bβ chain, the DNA segment comprising genomic DNA encoding the Bβ chain; and*

*a third DNA segment encoding a secretion signal operably linked to a heterologous fibrinogen γ chain, the DNA segment comprising genomic DNA encoding the γ chain, wherein each chain is from the same species, and wherein each of said first, second and third segments is operably linked to additional DNA segments required for its expression in the mammary gland of a host female mammal;*

*and the first, second, third segments are linked in a single vector.*

* * * * *